US008440837B2

(12) United States Patent
Hopper et al.

(10) Patent No.: US 8,440,837 B2
(45) Date of Patent: May 14, 2013

(54) 2-SUBSTITUTED-ETHYNYLTHIAZOLE DERIVATIVES AND USES OF SAME

(75) Inventors: Allen Hopper, Katonah, NY (US); Anette Graven Sams, Værlose (DK); Gitte Kobberoee Mikkelsen, Ballerup (DK); Mathivanan Packiarajan, Saddle Brook, NJ (US); Michel Grenon, Saddle Brook, NJ (US)

(73) Assignee: H. Lundbeck A/S, Valby (DK)

( * ) Notice: Subject to any disclaimer, the term of this patent is extended or adjusted under 35 U.S.C. 154(b) by 10 days.

(21) Appl. No.: 12/908,588

(22) Filed: Oct. 20, 2010

(65) Prior Publication Data

US 2011/0092475 A1    Apr. 21, 2011

Related U.S. Application Data

(60) Provisional application No. 61/253,452, filed on Oct. 20, 2009.

(51) Int. Cl.

| | | |
|---|---|---|
| *C07D 275/02* | (2006.01) | |
| *C07D 277/00* | (2006.01) | |
| *C07D 415/00* | (2006.01) | |
| *C07D 413/00* | (2006.01) | |
| *C07D 265/36* | (2006.01) | |
| *C07D 403/00* | (2006.01) | |
| *C07D 215/00* | (2006.01) | |
| *C07D 513/02* | (2006.01) | |
| *C07D 401/00* | (2006.01) | |
| *A61K 31/397* | (2006.01) | |
| *A61K 31/55* | (2006.01) | |
| *A61K 31/535* | (2006.01) | |
| *A61K 31/44* | (2006.01) | |
| *A61K 31/445* | (2006.01) | |
| *A61K 31/425* | (2006.01) | |

(52) U.S. Cl.
USPC ........... 548/206; 548/200; 544/133; 544/369; 544/105; 540/603; 546/118; 546/16; 546/209; 514/210.16; 514/326; 514/365; 514/236.8; 514/254.02; 514/217.1; 514/303; 514/278; 514/210.18; 514/230.5

(58) Field of Classification Search ....................... None
See application file for complete search history.

(56) References Cited

U.S. PATENT DOCUMENTS

| | | | |
|---|---|---|---|
| 4,990,520 A | 2/1991 | Trybulski et al. | |
| 2002/0193405 A1 | 12/2002 | Askew et al. | |
| 2003/0119811 A1 | 6/2003 | Liverton et al. | |
| 2010/0029690 A1 | 2/2010 | Atobe et al. | |
| 2011/0184027 A1* | 7/2011 | Khairatkar-Joshi et al. | 514/342 |

FOREIGN PATENT DOCUMENTS

| | | |
|---|---|---|
| EP | 1870412 A1 | 12/2007 |
| WO | 9633181 | 10/1996 |
| WO | 2006/074884 A1 | 7/2006 |
| WO | 2006091506 A2 | 8/2006 |
| WO | 2006091671 A1 | 8/2006 |
| WO | 2006121860 A2 | 11/2006 |
| WO | 2007/080050 A2 | 5/2007 |
| WO | 2008053913 A1 | 5/2008 |
| WO | 2008/074835 A1 | 6/2008 |
| WO | WO 2008074835 A1 * | 6/2008 |
| WO | 2010007482 A2 | 1/2010 |
| WO | 2010/025553 A1 | 3/2010 |
| WO | 2010035052 A1 | 4/2010 |

OTHER PUBLICATIONS

Aggleton J.P., et al., 1986. "The Effects of Hippocampal Lesions Upon Spatial and Non-Spatial Tests of Working Memory," Behavioral Brain Research, 19(2):133-146.
Bach, P., et al., 2007. "Metabotropic Glutamete Receptor 5 Modulators and Their Potential Therapeutic Applications," Expert Opinion on Therapeutic Patents, 17(4):371-384.
Barton, A., et al., 1982. "The Preparation of Thiazole-4- and -5-Carboxylates, and an Infrared Study of their Rotational Isomers," J. Chem. Soc. Perkin Trans 1: Org. and Bioorg. Chem., pp. 159-164.
Berge, S.M., et al., 1977. "Pharmaceutical Salts," Journal of Pharmaceutical Science, 66(1):2.
Birrell, J., et al., 2000. "Medial Frontal Cortex Mediates Perceptual Attentional Set Shifting in the Rat," The Journal of Neuroscience, 20(11):4320-4324.
Bontempi, B., et al., 1996. "Differential Temporal Evolution of Post-Training Changes in Regional Brain Glucose Metabolism Induced by Repeated Spatial Discrimination Training in Mice: Visualization of the Memory Consolidation Process?," European Journal of Neuroscience, 8:2348-2360.
Cheng, Y., et al., 1973. "Relationship Between the Inhibition Constant (KI) and the Concentration of Inhibitor which Causes 50 Per Cent Inhibition (I50) of an Enzymatic Reaction," Biochemical Pharmacology, 22:3099-3108.
Cui, Y., et al., 2005. "Identification of Potent Type I MetAP Inhibitors by Simple Bioisosteric Replacement. Part 1: Synthesis and Preliminary SAR Studies of Thiazole-4-Carboxylic Acid Thiazole-2-Ylamide Derivatives," Bioorganic Medical Chemistry Letters, 15:3732-3736.
Day, M., 2005. "Ovariectomy-Induced Disruption of Long-Term Synaptic Depression in the Hippocampal CA1 Region in Vivo is Attenuated with Chronic Estrogen Replacement," Neurobiology of Learning and Memory, 83:13-21.

(Continued)

Primary Examiner — Nyeemah A Grazier
(74) Attorney, Agent, or Firm — Stephen K. Kalinchak; Margaret M. Buck

(57) ABSTRACT

The present invention provides 2-substituted-ethynylthiazole derivatives of formula (I):

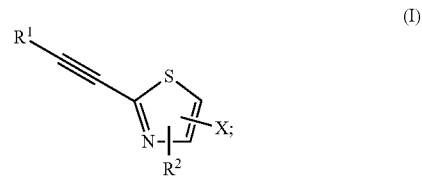

(I)

Figure 1:
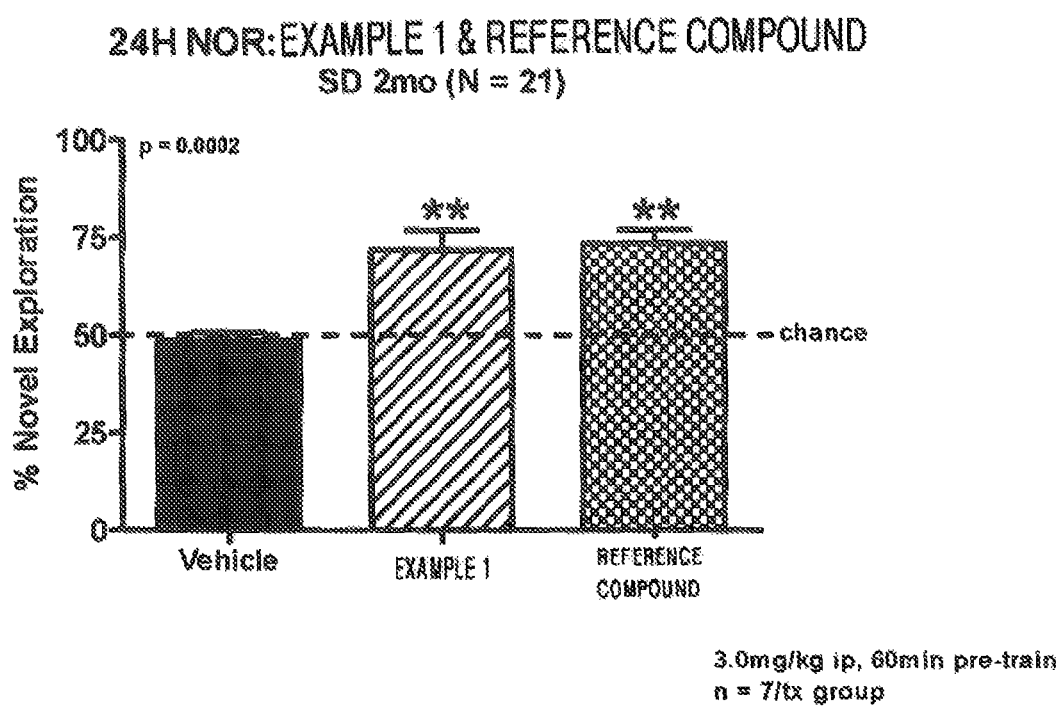

wherein $R^1$, $R^2$ and X are as defined herein, or a pharmaceutically acceptable salt thereof; and pharmaceutical compositions and methods of using same.

16 Claims, 2 Drawing Sheets

OTHER PUBLICATIONS

Depoortere, R., et al., 2003. "SSR181507, A Dopamine D2 Receptor Antagonist and 5-HT1A Receptor Agonist II: Behavioral Profile Predictive of an Atypical Antipsychotic Activity," Neuropsychopharmacology, 28:1889-1902.

Freed, W.J., et al., 1984. "Effects of Neuroleptics on Phencyclidine (PCP)-Induced Locomotor Stimulation in Mice," Neuropharmacology, 23(2A):175-181.

Fung, Y.K., et al., 1986. "Modulation of Apomorphine-Induced Climbing Behavior by Estradiol," Pharmacology Biochemistry and Behavior, 24(1):139-141.

Fung, Y.K., et al., 1987. "Inhibition by Bromoestrogens of the Effects of Estradiol on Apomorphine-Induced Climbing Behavior," Steroids, 49(4-5):287-294.

Gould, T.J., et al., 2002. "MK-801 Disrupts Acquisition of Contextual Fear Conditioning but Enhances Memory Consolidation of Cued Fear Conditioning," Behavioral Pharmacology, 13:287-294.

Grayson, B., et al., 2007. "Atypical Antipsychotics Attenuate a Subchronic PCP-Induced Cognitive Deficit in the Novel Object Recognition Task in the Rat," Behavioural Brain Research, 184:31-38.

Hamm, A.O., et al., 2003. "Affective Blindsight: Intact Fear conditioning to a Visual Cue in a Cortically Blind Patient," Brain, 126:267-275.

Jaeschke, G., et al., 2008. "mGlu5 Receptor Antagonists and their Therapeutic Potential,"Expert Opinion on Therapeutic Patents, 18(2):123-142.

May, L.T., 2007. "Allosteric Modulation of G Protein-Coupled Receptors," Annual Review of Pharmacology Toxicology, 47:1-51.

Morris, R., 1981. "Spatial Localization Does Not Require the Presence of Local Cues," Learning and Motivation 12:239-260.

Muir, J., et al., 1995. "Reversal of Visual Attentional Dysfunction Following Lesions of the Cholinergic Basal Forebrain by Physostigmine and Nicotine but not by the 5-HT3 Receptor Antagonist, Ondansetron," Psychopharmacology, 118:82-92.

O'Brien, J.A., et al. 2003. "A Family of Highly Selective Allosteric Modulators of the Metabotropic Glutamate Receptor Subtype 5," Mol. Pharmacology, 64:731-740.

Paulekuhn, G.S., et al., 2007. "Trends in Active Pharmaceutical Ingredient Salt Selection Based on Analysis of the Orange Book Database," Journal of Medicinal Chemistry, 50:6665-6672.

Robbins, T.W., et al., 1998. "Neural Systems Underlying Arousal and Attention," Annals NY Academy of Science, 846:222-237.

Rodefer, J.S., et al., 2005. "PDE10A Inhibition Reverses Subchronic PCP-Induced Deficits in Attentional Set-Shifting in Rats," European Journal of Neuroscience, 21:1070-1076.

Sams-Dodd, F., 1998. "Effects of Continuous D-Amphetamine and Phencyclidine Administration on Social Behaviour, Stereotyped Behaviour, and Locomotor Activity in Rats," Neuropharmacology, 19(1):18-25.

International Search Report for International Application No. PCT/US2010/053379, dated Dec. 9, 2010 (mailed Jan. 13, 2011).

Green, Mitchell D. et al, 2006. In vitro metabolic studies on the selective metabatropic glutamate receptor sub-type 5 (mGluR5) antagonist 3-[(2-methly-1,3-thiazol-4-yl)ethynyl]pyridine (MTEP), Neuroscience Letters, vol. 391(3). pp. 91-95.

Hodgetts, Kevin J. et al; 2002, Regiocontrolled Synthesis of Substituted Thiazoles, Organic Letters, vol. 4, No. 8, pp. 1363-1365.

Lu, Jin-Yong et al, 2007, Hetero Diels-Alder Synthesis of 3-Hydroxypyridines: Access to the Nosiheptide Core, Journal Of Organic Chemistry, vol. 72, pp. 4205-4212.

Simeon, Fabrice G. et al., 2007, Synthesis and Simple F-Labeling of 3-Fluoro-5-(2-(2-(fluoromethyl)thiazol-4-yl)ethynyl)benzonitrile as a High Affinity Radioligand for Imaging Monkey Brain Metabotropic Glumate Subtype-5 Receptors with Positron Emission Tomography, vol. 50, pp. 3256-3266.

Extended European Search Report issued Mar. 13, 2013 in EP Application No. 10825591.0.

* cited by examiner

2-SUBSTITUTED-ETHYNYLTHIAZOLE DERIVATIVES AND USES OF SAME

FIELD OF THE INVENTION

The present invention provides compounds that are 2-substituted-ethynylthiazole derivatives, such as 2-substituted-ethynylthiazole-4-carboxamides and 2-substituted-ethynylthiazole-5-carboxamides, as well as pharmaceutical compositions and methods of treatment using same.

BACKGROUND OF THE INVENTION

This invention concerns 2-substituted-ethynylthiazole derivatives, such as 2-substituted-ethynylthiazole-carboxamides, which act as allosteric modulators of the metabotropic glutamate receptor 5 (mGlu5 receptors or mGluR5), as well as pharmaceutical compositions and methods of treatment utilizing these compounds.

Glutamate is the major excitatory neurotransmitter in the mammalian central nervous system. One means of modulating glutamate neurotransmission is through metabotropic glutamate receptors (mGluRs); another means being ionotropic receptors. Presently, eight mGluRs have been cloned and classified into three groups based on sequence homology, preferred signal transduction pathway and pharmacology. Group I of mGluRs includes mGluR1 and mGluR5, while Group II comprises mGluR2 and mGluR3 and Group III comprises mGlu4, 6, 7 and 8 receptors.

mGlu receptors have an essential role in normal brain functions, as well as in neurological, psychiatric, and neuromuscular disorders. mGlu5 receptors are located primarily postsynaptically and highly expressed in the limbic brain regions. mGlu5 receptors also are expressed in the thalamus, spinal cord, and vagal nerve systems, as well as peripherally in the skin on nerve endings and C fibers.

Ligands to the mGlu5 receptors have been shown to have promise for peripheral and central nervous system disorders. See e.g., G. Jaeschke et al., "mGlu5 receptor antagonists and their therapeutic potential," *Expert Opin. Ther. Patents,* 2008, 18, 2: 123-142. Yet some proffer that glutamate analogs targeting the orthosteric binding site may be limited by low brain penetration and insufficient selectivity with respect to the different mGluRs subtypes. Synthetic agonists may lead to continuous stimulation of the receptor since they are often designed to be metabolically stable. This continuous stimulation is not necessarily desirable, due to potential receptor desensitization issues. Also, with respect to receptor occupancy, synthetic antagonists may lead to prolonged blockade of receptor function, which may not be compatible with the kinetics of the pathology of a central nervous system disorder.

However, a more selective and controlled "fine-tuning" action on the mGlu5 receptor is feasible through allosteric modulation. See e.g., P. Bach et al., "Metabotropic glutamate receptor 5 modulators and their potential therapeutic applications," *Expert Opin. Ther. Patents,* 2007, 17, 4: 371-381. Allosteric modulation refers to binding by a modulator ligand to a site on a receptor that is different from the orthosteric primary substrate or ligand binding site. This ligand binding process results in conformational changes, which may profoundly influence the function of the protein (e.g., G protein-coupled receptors such as mGluRs, including mGluR5). Novel mGluR5 ligands that allosterically modulate the mGlu5 receptor may improve the therapeutic window of traditional central nervous system agents and/or the treatment of central nervous system disorders. The present invention is directed these, and other important, ends.

SUMMARY OF THE INVENTION

The present invention provides 2-substituted-ethynylthiazole derivatives of formula (I):

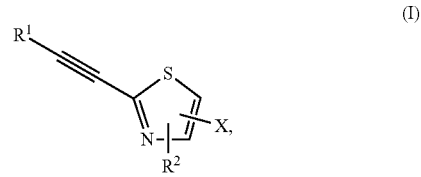

wherein:
X is —CONR$^3$R$^4$, —CH$_2$NR$^3$R$^4$, —CH(OH)R$^5$, —CO$_2$R$^3$, —COR$^5$, or —C(OH)R$^5$R$^6$, wherein:
R$^3$ is hydrogen or C$_1$-C$_6$alkyl;
R$^4$ is C$_1$-C$_6$alkyl, cycloalkyl, cycloalkylalkyl, heterocyclyl, heteroaryl, arylalkyl, or aryl, each of which is optionally mono-, di-, or tri-substituted independently with C$_1$-C$_6$alkyl, halogen, cycloalkyl, and aryl; or
R$^3$ and R$^4$ taken together with the N to which they are attached to form a 4 to 10 membered heterocyclyl, which optionally contains at least one additional heteroatom and optionally is mono-, di-, or tri-substituted independently with C$_1$-C$_6$alkyl, hydroxy, C$_1$-C$_6$alkoxy, C$_1$-C$_6$alkoxyalkyl, C$_1$-C$_6$cycloalkyl, CO$_2$C$_1$-C$_6$alkyl, hydroxyalkyl, —CN, —NH$_2$, —NH(C$_1$-C$_3$alkyl), —N(C$_1$-C$_3$alkyl)$_2$, —NHCOC$_1$-C$_{1-6}$alkyl, acyl, aryl, heteroaryl, heterocyclyl, heterocyclyl-C$_1$-C$_6$alkyl, =O, and halogen;
R$^5$ is C$_1$-C$_3$alkyl, CF$_3$, CHF$_2$, cycloalkyl, cycloalkylalkyl, aryl, heteroaryl, or heterocyclyl that is attached via a carbon having from 1 to 3 substitutions, which are selected from a group consisting of C$_1$-C$_6$alkyl, halogen, cycloalkyl, aryl, hydroxy, C$_1$-C$_6$alkoxy, hydroxyalkyl, —CN, —NH$_2$, —NH(C$_1$-C$_3$alkyl), —N(C$_1$-C$_3$alkyl)$_2$, acyl, heteroaryl, heterocyclyl, and carbonyl; and
R$^6$ is hydrogen, C$_1$-C$_3$alkyl, CF$_3$, CHF$_2$, or C$_3$-C$_6$cycloalkyl;
R$^1$ is hydrogen, C$_1$-C$_6$alkyl, C$_3$-C$_6$cycloalkyl, aryl or heteroaryl, which is optionally mono-, or di-substituted independently with C$_1$-C$_3$alkyl, C$_1$-C$_3$alkoxy, hydroxyl, CF$_3$, CHF$_2$, CN and halogen;
R$^2$ is hydrogen, C$_1$-C$_3$alkyl, CF$_3$, CHF$_2$, or halogen;
with the proviso that:
X and R$^2$ are attached either to the fourth or fifth carbon of the thiazole ring and when X is attached to the fourth carbon, R$^2$ is attached to the fifth carbon and vice versa; or
a pharmaceutically-acceptable salt thereof.

The present invention also provides a pharmaceutical composition comprising at least one compound of the invention or a pharmaceutically acceptable salt thereof, and at least one pharmaceutically acceptable carrier.

The present invention also provides a method of treating a disease or disorder, the method comprises administering an effective amount of at least one compound of the present invention or a pharmaceutically acceptable salt thereof to a mammal in need thereof, wherein the disease or disorder is psychosis, schizophrenia, cognitive impairment associated with schizophrenia (CIAS), a disease involving a psychotic symptom, schizophreniform disorder, schizoaffective disorder, delusional disorder, brief psychotic disorder, shared psychotic disorder, substance-induced psychotic disorder, an affective disorder, depression, mania, bipolar disorder, or a combination thereof.

The present invention further provides a method of improving cognitive functioning, comprising administering an effective amount of a compound of claim 1 to a human in need thereof. In some such embodiments, the human suffers from cognitive dysfunction, which presents because of a disease or disorder, such as, and without limitation, psychosis, schizophrenia, a disease involving a psychotic symptom, schizophreniform disorder, schizoaffective disorder, delusional disorder, brief psychotic disorder, shared psychotic disorder, substance-induced psychotic disorder, an affective disorder, or a combination.

In some embodiments, the method of improving cognitive function is with respect to cognition related to attention deficit hyperactivity disorder (ADHD).

In some embodiments of the methods herein, a symptom of the disease or disorder is treated.

FIGURES

FIG. 1: Effect of a compound of formula (I) on working memory processes in a rodent model of cognition in accordance with an embodiment of the invention.

Figure 2:
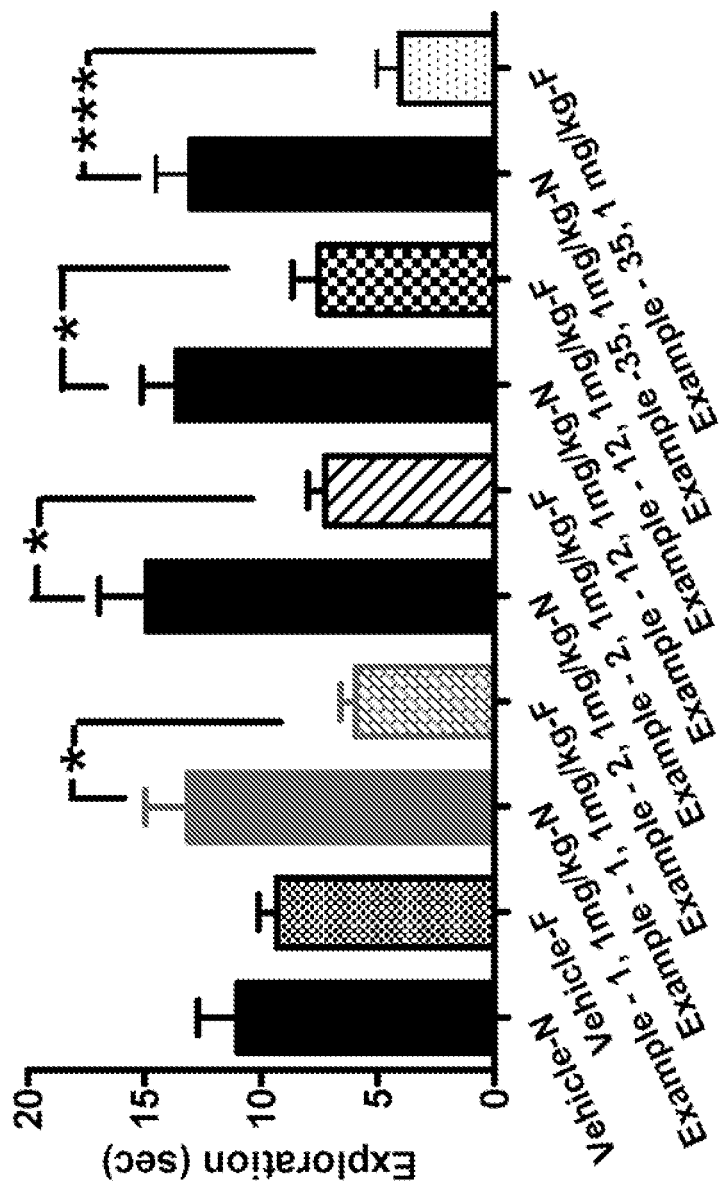

FIG. 2: Effect of compounds of formula (I) on working memory processes in a rodent model of cognition in accordance with an embodiment of the invention.

DETAILED DESCRIPTION OF THE INVENTION

In one aspect, the present invention provides 2-substituted-ethynylthiazole derivatives of formula (I):

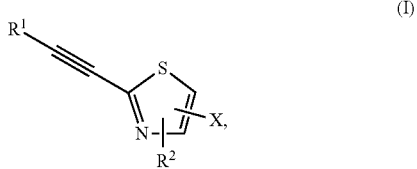

(I)

wherein:
X is —$CONR^3R^4$, —$CH_2NR^3R^4$, —$CH(OH)R^5$, —$CO_2R^3$, —$COR^5$, or —$C(OH)R^5R^6$, wherein:
  $R^3$ is hydrogen or $C_1$-$C_6$alkyl;
  $R^4$ is $C_1$-$C_6$alkyl, cycloalkyl, cycloalkylalkyl, heterocyclyl, heteroaryl, arylalkyl, or aryl, each of which is optionally mono-, di-, or tri-substituted independently with $C_1$-$C_6$alkyl, halogen, cycloalkyl, and aryl; or
  $R^3$ and $R^4$ taken together with the N to which they are attached to form a 4 to 10 membered heterocyclyl, which optionally contains at least one additional heteroatom and optionally is mono-, di-, or tri-substituted independently with $C_1$-$C_6$alkyl, hydroxy, $C_1$-$C_6$alkoxy, $C_1$-$C_6$alkoxyalkyl, $C_1$-$C_6$cycloalkyl, $CO_2C_1$-$C_6$alkyl, hydroxyalkyl, —CN, —$NH_2$, —NH($C_1$-$C_3$alkyl), —N($C_1$-$C_3$alkyl)$_2$, —NHCOC$_1$-$C_6$alkyl, acyl, aryl, heteroaryl, heterocyclyl, heterocyclyl-$C_1$-$C_6$alkyl, =O, and halogen;
  $R^5$ is $C_1$-$C_3$alkyl, $CF_3$, $CHF_2$, cycloalkyl, cycloalkylalkyl, aryl, heteroaryl, or heterocyclyl that is attached via a carbon having from 1 to 3 substitutions, which are selected from a group consisting of $C_1$-$C_6$alkyl, halogen, cycloalkyl, aryl, hydroxy, $C_1$-$C_6$alkoxy, hydroxyalkyl, —CN, —$NH_2$, —NH($C_1$-$C_3$alkyl), —N($C_1$-$C_3$alkyl)$_2$, acyl, heteroaryl, heterocyclyl, and carbonyl; and
  $R^6$ is hydrogen, $C_1$-$C_3$alkyl, $CF_3$, $CHF_2$, or $C_3$-$C_6$cycloalkyl;
  $R^1$ is hydrogen, $C_1$-$C_6$alkyl, $C_3$-$C_6$cycloalkyl, aryl or heteroaryl, which is optionally mono-, or di-substituted independently with $C_1$-$C_3$alkyl, $C_1$-$C_3$alkoxy, hydroxyl, $CF_3$, $CHF_2$, CN and halogen;
  $R^2$ is hydrogen, $C_1$-$C_3$alkyl, $CF_3$, $CHF_2$, or halogen;
  with the proviso that:
    X and $R^2$ are attached either to the fourth or fifth carbon of the thiazole ring and when X is attached to the fourth carbon, $R^2$ is attached to the fifth carbon and vice versa; or
    a pharmaceutically-acceptable salt thereof.

The term "alkyl", employed alone or as part of a group, is defined herein, unless otherwise stated, as either a straight-chain or branched saturated hydrocarbon. In some embodiments, the alkyl moiety contains 6, 5, 4, 3, 2 or 1 carbon atoms. Where the term "alkyl" appears herein without a carbon atom range, it means a range of $C_1$-$C_6$. Where the term "alkyl" appears herein with a carbon range, it means an alkyl of any number within in the carbon range identified, such as a $C_1$-$C_3$alkyl means either methyl, ethyl or propyl. Examples of saturated hydrocarbon alkyl moieties include, but are not limited to, chemical groups such as methyl, ethyl, n-propyl, isopropyl, n-butyl, tert-butyl, iso-butyl, sec-butyl, n-pentyl, n-hexyl, and the like. Alkyl also refers to alkyl moieties where the alkyl group is substituted by hydroxy, cyano, alkoxy, alkylamino, dialkylamino, alkylamide, dialkylamide, and the like, including without limitation, —$C_1$-$C_4$alkyl-OH, —$C_1$-$C_4$alkyl-OCH$_3$, —$C_1$-$C_4$alkyl-NHCH$_3$, —$C_1$-$C_4$alkyl-N(CH$_3$)$_2$, —$C_1$-$C_4$alkyl-CONHCH$_3$, —$C_1$-$C_4$alkyl-CON(CH$_3$)$_2$, —$C_1$-$C_4$alkyl-NHCOCH$_3$, and —$C_1$-$C_4$alkyl-N(CH$_3$)COCH$_3$.

The term "alkoxy", employed alone or in combination with other terms, is defined herein, unless otherwise stated, as —O-alkyl, where "alkyl" is as previously defined herein. Examples of alkoxy moieties include, but are not limited to, chemical groups such as methoxy, ethoxy, iso-propoxy, sec-butoxy, tert-butoxy, and homologs, isomers, and the like. Alkoxy also refers to —O-alkyl moieties where the alkyl group is substituted by hydroxy, cyano, alkoxy, alkylamino, dialkylamino, alkylamide, dialkylamide, and the like, including without limitation, —O$C_1$-$C_4$alkyl-OH, —O$C_1$-$C_4$alkyl-OCH$_3$, —O$C_1$-$C_4$alkyl-NHCH$_3$, —O$C_1$-$C_4$alkyl-N(CH$_3$)$_2$, —O$C_1$-$C_4$alkyl-CONHCH$_3$, —O$C_1$-$C_4$alkyl-CON(CH$_3$)$_2$, —O$C_1$-$C_4$alkyl-NHCOCH$_3$, and —O$C_1$-$C_4$alkyl-N(CH$_3$)COCH$_3$.

The term "hydroxyalkyl", employed alone or in combination with other terms, is defined herein, unless otherwise stated, as -alkyl-OH, where "alkyl" is as previously defined herein. Non-limiting examples include methyl-OH, ethyl-OH, n-propyl-OH, and the like.

As used herein, the term "cycloalkyl", employed alone or in combination with other terms, is defined, unless otherwise stated, as a cyclized alkyl group having from 3 to 8 ring carbon atoms, where "alkyl" is as defined herein. Examples of cycloalkyl moieties include, but are not limited to, chemical groups such as cyclopropyl, cyclobutyl, cyclopentyl, and cyclohexyl.

The terms "halo" or "halogen", employed alone or in combination with other terms, is defined herein, unless otherwise stated, as fluoro, chloro, bromo, or iodo.

The term "aryl", employed alone or in combination with other terms, is defined herein, unless otherwise stated, as an aromatic hydrocarbon of up to 14 carbon atoms, which can be a single ring (monocyclic) or multiple rings (e.g., bicyclic, tricyclic, polycyclic) fused together or linked covalently. Any suitable ring position of the aryl moiety can be covalently linked to the defined chemical structure. Examples of aryl moieties include, but are not limited to, chemical groups such as phenyl, 1-naphthyl, 2-naphthyl, and the like. An aryl group can be unsubstituted or substituted as described herein.

The term "heteroaryl", employed alone or in combination with other terms, is defined herein, unless otherwise stated, as a monocyclic or polycyclic (fused together or linked covalently) aromatic hydrocarbon ring comprising one or more heteroatoms independently selected from nitrogen, oxygen, and sulfur. A heteroaryl group comprises up to 14 carbon atoms and 1 to 6 heteroatoms. Examples of heteroaryl groups include, but are not limited to, pyridinyl, pyridazinyl, triazinyl, pyrrolyl, pyrazolyl, imidazolyl, (1,2,3)- and (1,2,4)-triazolyl, pyrazinyl, pyrimidinyl, tetrazolyl, furyl, thienyl, isoxazolyl, thiazolyl, oxazolyl, 2-quinolinyl, 2-quinazolinyl, 3-phenyl-2-quinolinyl and the like. A heteroaryl group can be unsubstituted or substituted as described herein.

The term "heterocyclyl", employed alone or in combination with other terms, is defined herein, unless otherwise stated, as a univalent group formed by removing a hydrogen atom from any ring atom of a heterocycle, including, without limitation, bicyclo- and spirocyclo-moieties such as

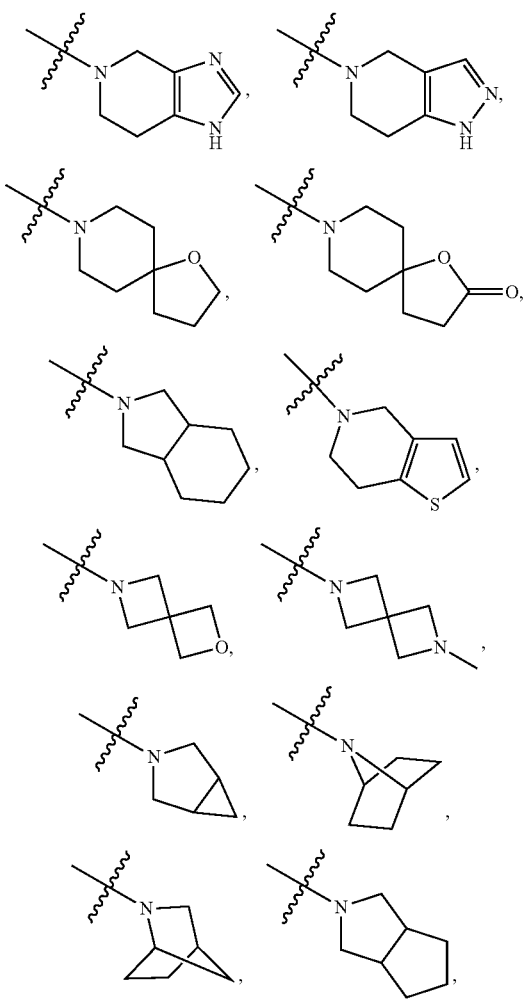

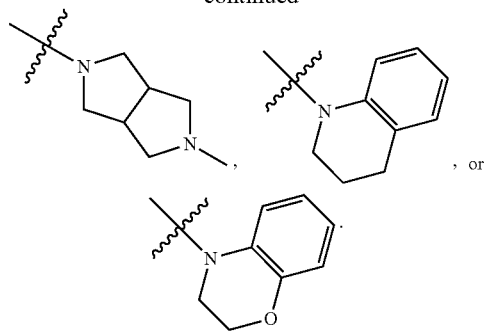

The term "acyl" employed alone or in combination with other terms, is defined herein, unless otherwise stated, as groups of formula —C(O)-alkyl, where alkyl is a previously described herein; i.e., an alkylcarbonyl, such as formyl, acetyl and the like.

The term "aminoalkyl", employed alone or in combination with other terms, is defined herein, unless otherwise stated, as alkyl-amino, where the term "alkyl" is as previously defined herein and the term "amino" is —$NH_2$, —NH—, or —N<. Non-limiting examples include —$CH_3NH$—, $CH_3CH_2NH$—, ($C_1$-$C_3$alkyl)NH—, ($C_1$-$C_3$alkyl)$_2$N—, and the like.

The term "alkylamino" employed alone or in combination with other terms, is defined herein, unless otherwise stated, as amino-alkyl, where the term "alkyl" is as previously defined herein and the term "amino" is —$NH_2$, —NH—, or —N<. Non-limiting examples include —$NHCH_3$, —$NHCH_2CH_3$, —NH($C_1$-$C_3$alkyl), —N($C_1$-$C_3$alkyl)$_2$, and the like.

As used herein, the term "arylalkyl", employed alone or in combination with other terms, is defined, unless otherwise stated, as an alkyl-aryl group where the terms "alkyl" and "aryl" are as previously defined herein.

The term "heteroarylalkyl", employed alone or in combination with other terms, is defined herein, unless otherwise stated, as an alkyl-heteroaryl group where the terms "alkyl" and "heteroaryl" are as previously defined herein.

The term "cycloalkylalkyl", employed alone or in combination with other terms, is defined herein, unless otherwise stated, as an alkyl-cycloalkyl group where the terms "alkyl" and "cycloalkyl" are as previously defined herein.

The term "heterocyclylalkyl", employed alone or in combination with other terms, is defined herein, unless otherwise stated, as an alkyl-heterocyclyl group where the terms "alkyl" and "heterocyclyl" are as previously defined herein.

In some embodiments, the compound of formula (I) is a 2-substituted-ethynylthiazole-carboxamide.

In some embodiments, the compound is of formula (Ia):

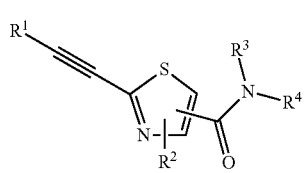

Ia

In some embodiments, the compound is of formula (Ia-i):

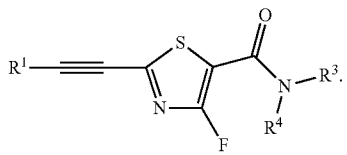

In some embodiments, the compound is of formula (Ib), (Ic), (Id) or (Ie):

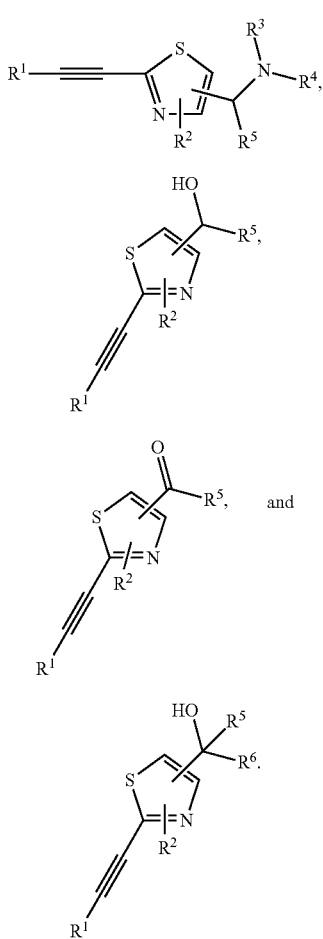

In some embodiments, at least one halogen is fluorine. In some embodiments, at least one halogen is chlorine. In some embodiments, two or more halogens are fluorine, chlorine or a combination thereof.

In some embodiments, at least one cycloalkyl is cyclopropyl, cyclopentyl or cyclohexyl. In some embodiments, two or more cycloalkyls are cyclopropyl, cyclopentyl, cyclohexyl, or a combination thereof.

In some embodiments, at least one alkyl is methyl, ethyl, or isopropyl. In some embodiments, at least two alkyls are methyl, ethyl, isopropyl, or a combination thereof. In some embodiments, at least three alkyls are ethyl, isopropyl, or a combination thereof.

In some embodiments, $R^1$ is hydrogen, $C_1$-$C_6$alkyl, $C_3$-$C_6$cycloalkyl, aryl or heteroaryl, which is optionally mono-, or di-substituted independently with $C_1$-$C_3$alkyl, $C_1$-$C_3$alkoxy, hydroxyl, $CF_3$, $CHF_2$, CN and halogen. In some embodiments, $R^1$ is an aryl, such as and without limitation, phenyl. In some embodiments, $R^1$ is an alkyl or cycloalkyl, such as and without limitation, cyclohexyl. In some embodiments, $R^1$ is a heteroaryl, such as and without limitation, thienyl, furyl, pyrazinyl, pyrimidyl, pyridyl, thiazolyl, or a moiety as shown below:

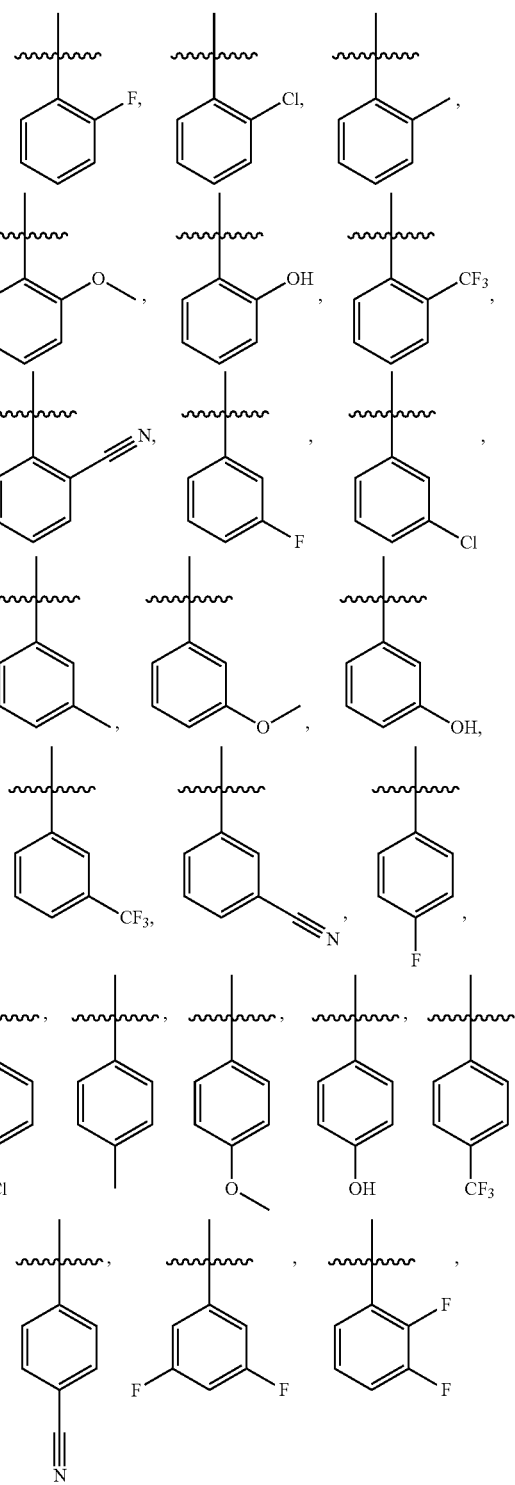

-continued

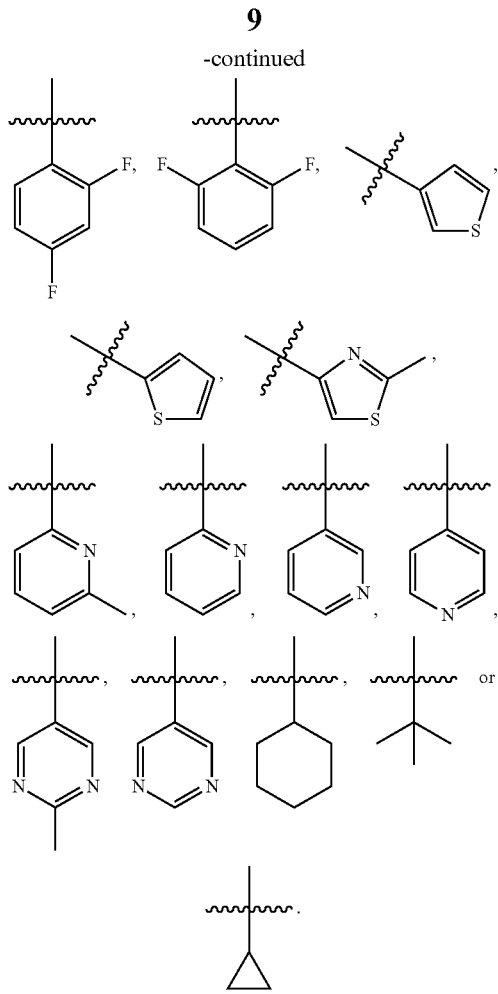

In some embodiments, $R^2$ is hydrogen. In some embodiments, $R^2$ is fluorine.

In some embodiments, the heterocyclyl formed by $R^3$ and $R^4$ together with the N to which they are attached is piperidinyl, pyrrolidinyl, morpholinyl, piperazinyl, or azepanyl; or a bicyclic or spiro moiety, such as:

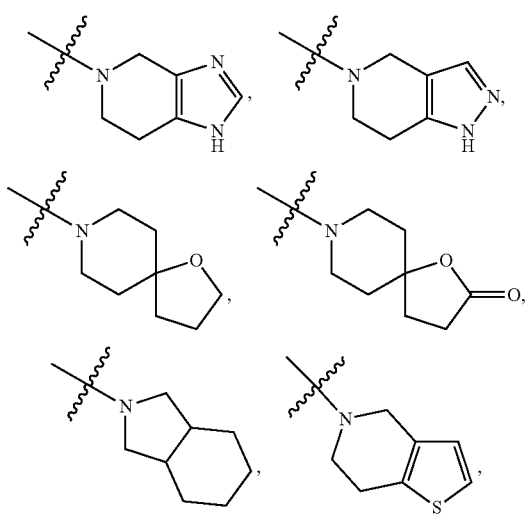

-continued

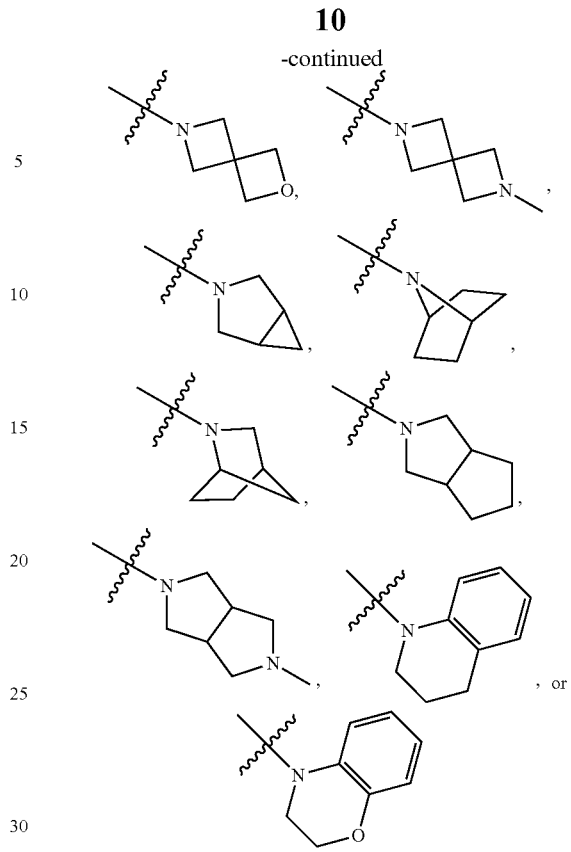

In some embodiments, $R^3$ and $R^4$ taken together with the N to which they are attached to form a 4 to 10 membered heterocyclyl, which optionally contains at least one additional heteroatom and optionally is mono-, di-, or tri-substituted independently with $C_1$-$C_6$alkyl, hydroxy, $C_1$-$C_6$alkoxy, $C_1$-$C_6$alkoxyalkyl, $C_1$-$C_6$cycloalkyl, $CO_2C_1$-$C_6$alkyl, hydroxyalkyl, —CN, —$NH_2$, —NH($C_1$-$C_3$alkyl), —N($C_1$-$C_3$alkyl)$_2$, —NHCO$C_1$-$C_6$alkyl, acyl, aryl, heteroaryl, heterocyclyl, heterocyclyl-$C_1$-$C_6$alkyl, =O, and halogen.

In some embodiments, $R^5$ is $C_1$-$C_3$alkyl, $CF_3$, $CHF_2$, cycloalkyl, cycloalkylalkyl, aryl, heteroaryl, or heterocyclyl that is attached via a carbon having from 1 to 3 substitutions, which are selected from a group consisting of $C_1$-$C_6$alkyl, halogen, cycloalkyl, and aryl.

In some embodiments, $R^6$ is hydrogen, $C_1$-$C_3$alkyl, $CF_3$, $CHF_2$, or $C_3$-$C_6$cycloalkyl.

In some embodiments, the compound of the present invention is a compound disclosed in the Experimental Section below. In some embodiments, the compound is the compound of Example 1-246.

Another aspect of the present invention is a composition that comprises an effective amount of at least one compound of formula (I), and a pharmaceutically acceptable carrier or excipient.

In some embodiments, the pharmaceutical composition comprising at least one compound of formula (I) improves cognitive functioning in a human. In some embodiments, the composition improves cognitive functioning in a human suffering from cognitive dysfunction. In some embodiments, the pharmaceutical composition is for use in a human who has been diagnosed with a cognitive impairment. In some embodiments, the composition is for use in a human who has first-episode schizophrenia.

The composition may be adapted to any mode of administration, such as orally (including sublingually), via implants, parentally (including intravenous, intraperitoneal, intraarticularly and subcutaneous injections), rectally, intranasally, topically, ocularly (via eye drops), vaginally, and transdermally.

A compound of formula (I) can be used either as a free base or in the form of a salt derived from pharmaceutically acceptable acids or bases. The salt includes without limitation the following: salts with inorganic acids, e.g., hydrochloric acid, hydrobromic acid, sulfuric acid, nitric acid, and phosphoric acid, and organic acids e.g., acetic acid, oxalic acid, citric acid, tartaric acid, succinic acid, maleic acid, benzoic acid, benzene sulfonic acid, fumaric acid, malic acid, methane sulfonic acid, pamoic acid, and para-toluene sulfonic acid. Other salts include salts with alkali metals or alkaline earth metals, e.g., sodium, potassium, calcium and magnesium, or with organic bases, including quaternary ammonium salts. Further non-limiting examples of pharmaceutically acceptable inorganic and organic acid addition salts include those listed in [S. M. Berge et al., *J. Pharm. Sci.* 1977, 66, 1: 2, and G. S. Paulekuhn, et al., *J. Med. Chem.* 2007, 50, 26: 6665-6672].

A compound of formula (I) can also be used in the form of an ester, carbamate and other conventional prodrug form, which generally will be a functional derivative of the compound that is readily converted to the active moiety in vivo. Also included are metabolites of a compound of the present invention defined as active species produced upon introduction of the compound into a biological system.

When compound of formula (I) is employed as described above, it may be combined with one or more pharmaceutically acceptable excipients or carriers, e.g., solvents, diluents and the like. Such pharmaceutical preparations may be administered orally in such forms as tablets, capsules (including, e.g., time release and sustained release formulations), pills, lozenges, aerosols, dispersible powders, granules, solutions, suspensions (containing, e.g., a suspending agent, at, e.g., from about 0.05 to about 5% of suspending agent), syrups (containing, e.g., sugar or a sugar substitute such as aspartame, at, e.g., about 10 to about 50% sugar or sugar substitute), elixirs and the like, or parenterally in the form of sterile injectable solutions, suspensions or emulsions containing, e.g., from about 0.05 to about 5% suspending agent in an isotonic medium. Such preparations may contain, e.g., from about 25 to about 90% of the active ingredient in combination with the carrier, more customarily from about 5% and about 60% by weight. The effective dosage of an active ingredient (e.g., a compound or salt of the present invention and a prodrug or metabolite thereof) employed may vary depending on the particular compound, salt, prodrug or metabolite used, the mode of administration, age, weight, sex and medical condition of the patient, and the severity of the disease, disorder, condition, and/or system being treated. The selection of the appropriate administration and dosage form for an individual mammal will be apparent to those skilled in the art. Such determinations are routine to a physician, veterinarian or clinician of ordinary skill in the art (see e.g., *Harrison's Principles of Internal Medicine*, Anthony Fauci et al. (eds.) 14$^{th}$ ed. New York: McGraw Hill (1998)). Further, the dosage regimen may be adjusted to provide the optimal therapeutic response. For example, several divided doses may be administered daily or the dose may be proportionally reduced as indicated by the needs of the therapeutic situation.

Solid carriers, e.g., starch, lactose, dicalcium phosphate, microcrystalline cellulose, sucrose and kaolin, liquid carriers, e.g., sterile water, polyethylene glycols, glycerol, non-ionic surfactants and edible oils such as corn, peanut and sesame oils, may be employed as are appropriate to the nature of the active ingredient and the particular form of administration desired. Adjuvants customarily employed in the preparation of pharmaceutical compositions may be advantageously included. Non-limiting examples of adjuvants include flavoring agents, coloring agents, preserving agents, and antioxidants, such as vitamin E, ascorbic acid, BHT and BHA.

An active compound also may be administered parenterally or intraperitoneally. Solutions or suspensions of the active compound as a free base, neutral compound or pharmacologically acceptable salt can be prepared in water suitably mixed with a surfactant such as hydroxypropylcellulose. Dispersions also can be prepared in glycerol, liquid polyethylene glycols and mixtures thereof in oils. These preparations may contain a preservative to prevent the growth of microorganisms under ordinary conditions of storage and use.

The pharmaceutical forms suitable for injectable or infusing use include sterile aqueous solutions, suspensions or dispersions, and sterile powders for the extemporaneous preparation of sterile injectable or infusing solutions, suspension or dispersions. In all cases, the form must be sterile and must be fluid to the extent that easy injectability and infusing exists. It must be stable under conditions of manufacture and storage and must be preserved against the contaminating action of microorganisms. The carrier can be a solvent or dispersion medium containing, for example, water, ethanol, and polyol (e.g., glycerol, propylene glycol, and liquid polyethylene glycol), suitable mixtures thereof, and vegetable oil.

Furthermore, active compounds of the present invention can be administered intranasally or transdermally using vehicles suitable for intranasal or transdermal delivery known to those ordinarily skilled in the art. Transdermal administration includes all administrations across the surface of the body and the inner linings of bodily passages including epithelial and mucosal tissues, using carrier systems such as lotions, creams, foams, pastes, patches, suspensions, solutions, and suppositories (rectal and vaginal). Creams and ointments may be viscous liquid or semisolid emulsions of either the oil-in-water or water-in-oil type. Pastes comprised of absorptive powders dispersed in petroleum or hydrophilic petroleum containing the active ingredient also may be suitable. A variety of occlusive devices may be used to release the active ingredient into the blood stream such as a semi-permeable membrane covering a reservoir containing the active ingredient with or without a carrier, or a matrix containing the active ingredient. Other occlusive devices are known in the literature. When using a transdermal delivery system, the dosage administration will be continuous rather than a single or divided daily dose.

A compound of formula (I) can also be administered in the form of a liposome delivery system where the liposomal lipid bilayer is formed from a variety of phospholipids. A compound of formula (I) also may be delivered by the use of a carrier such as monoclonal antibodies to which the compound is coupled. Other carriers to which a compound of the present invention also may be coupled are a soluble polymer or a biodegradable polymer useful in achieving controlled release of an active ingredient.

It is understood by those practicing the art that some of the compounds of the present invention may contain one or more asymmetric centers, and thus may give rise to enantiomers and diastereomers. The present invention includes all stereoisomers including individual diastereomers and resolved, enantiomerically pure stereoisomers, as well as racemates, and all other variations of stereoisomers, and mixtures and pharmaceutically acceptable salts thereof, which possess the indicated activity. Optical isomers may be obtained in pure form by customary procedures known to those skilled in the art, and include, but are not limited to, chiral chromatographic separations, diastereomeric salt formation, kinetic resolution, and asymmetric synthesis. It is also understood that this invention encompasses all possible regioisomers, endo-exo isomers, and mixtures thereof that possess the indicated activity. Such isomers can be obtained in pure form by customary procedures known to those skilled in the art, and include, but are not limited to, column chromatography, thin-layer chromatography, and high-performance liquid chromatography and super critical fluid chromatography (SFC). It is understood by those practicing the art that some of the compounds of the present invention may be chiral due to hindered rotation, and give rise to atropisomers, which can be resolved and obtained in pure form by customary procedures known to those skilled in the art. It is further understood by those practicing the art that some of the compounds of the present invention include structural isomers, including tautomers.

Included also in this invention are all polymorphs and hydrates of the compounds of the present invention.

Another aspect of the present invention is a method for using a compound of formula (I). The invention is to be understood as embracing all simultaneous, sequential or separate use of any combination of the compounds of the invention with any pharmaceutical composition useful in the methods described herein.

In some embodiments, the method includes administering an effective amount of a compound of formula (I), or salt thereof. In some embodiments, the method in includes administering a therapeutically effective amount of a compound described herein, or salt thereof.

As used herein, the phrase "effective amount" when applied to a compound of the invention, is intended to denote an amount sufficient to cause an intended biological effect. The phrase "therapeutically effective amount" when applied to a compound of the invention is intended to denote an amount of the compound that is sufficient to ameliorate, palliate, stabilize, reverse, slow or delay the progression of a disorder or disease state, or of a symptom of the disorder or disease. In some embodiments, the method of the present invention provides for administration of combinations of compounds. In such instances, the "effective amount" is the amount of the combination sufficient to cause the intended biological effect.

In some embodiments, the method includes administering an effective amount of a combination of two or more of the compounds described herein, or salts thereof. It is specifically intended that the phrases "combination of two or more of the compounds described herein, or salts thereof," or "at least one compound as described herein, or a pharmaceutically acceptable salt thereof," or similar language describing specific compounds, includes the administration of such compounds in any proportion and combination of salt, neutral or free base forms; i.e., includes the administration of such compounds each in the base form, each in the neutral form or each in the salt form, or one or more in the base form and one or more in the neutral form, or one or more in the base form and one or more in the salt form, or one or more in the neutral form and one or more in the salt form, in any proportion of the neutral and/or basic compounds and/or salts.

The term "treatment" or "treating" as used herein means ameliorating or reversing the progress of a disease or disorder, or ameliorating or reversing one or more symptoms or side effects of such disease or disorder. For example, "treatment" or "treating" can refer to slowing, interrupting, controlling, lessening, stopping, or regulating the progression or continuation of a disease or disorder. "Treatment" or "treating", as used herein, also means to, inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of (or reducing) the extent of a disorder or disease, stabilized (i.e., not worsening) disease or disorder state, delay or slowing of a disease or disorder state, amelioration or palliation of a disease or disorder state, and remission of a disease or disorder, whether partial or total, detectable or undetectable.

The term "prevent" or "preventing" as used herein means to keep from happening or existing. The term "administering" as used herein refers to either directly administering a compound of the present invention, or administering a prodrug, derivative, or analog of same, that will form an effective amount of the compound within a mammal.

The present invention also provides a method of treating a disease or disorder, the method comprises administering a therapeutically effective amount of at least one compound of formula (I) or a pharmaceutically acceptable salt thereof to a mammal in need thereof, wherein the disease or disorder is a central nervous system disease or disorder, such as psychosis, schizophrenia, cognition impairment, and the like.

A compound of formula (I) can allosterically modulate the mGlu5 receptor.

In some embodiments, the compound of formula (I) is a positive allosteric modulator of the mGlu5 receptor. An allosteric modulator that enhances or potentiates the affinity of an orthosteric ligand for the mGluR5 receptor and/or enhances or potentiates an orthosteric agonist's efficacy is an allosteric enhancer (or potentiator) or positive allosteric modulator (PAM). See e.g., May, L. T. *Annu. Rev. Pharmacol. Toxicol.* 2007, 47, 1-51.

In some embodiments, the compound of formula (I) is a negative allosteric modulator of the mGlu5 receptor. An allosteric modulator that reduces or diminishes the affinity of an orthosteric ligand for the mGluR5 receptor and/or reduces or diminishes an orthosteric agonist's efficacy is an allosteric antagonist (or inhibitor) or negative allosteric modulator (NAM). Id.

In some embodiments, the compound of formula (I) is a silent allosteric modulator of the mGlu5 receptor. A ligand that binds to an allosteric site of the receptor but has no measurable intrinsic efficacy, but which may indirectly demonstrate efficacy by preventing an allosteric binding compound from displaying its own positive (PAM) or negative (NAM) efficacy, is a "silent allosteric modulator" (SAM).

In some embodiments, the method is a method of improving cognitive functioning, comprising administering an effective amount of a compound of formula (I) to a human in need thereof.

Diminished cognitive processes (i.e., cognitive impairment, cognitive deficit, cognitive dysfunction, decline in cognitive functioning, and the like) can be experienced in several human patient groups, e.g., in schizophrenic, depressive or psychotic patients, ADHD patients, and in patients with Parkinson's disease.

Cognitive impairment includes a decline in cognitive functions or cognitive domains, such as, e.g., difficulties with attention, learning, memory and executive function (relevant reactions to external stimuli). Cognitive impairment also may include: deficits in attention, disorganized thinking, slow thinking, difficulty in understanding, poor concentration, impairment of problem solving, poor memory, difficulty in expressing thoughts and/or integrating thoughts, feelings and behavior, and/or extinction of irrelevant thoughts, and difficulty in attention and vigilance, verbal learning and memory, visual learning and memory, speed of processing, social cognition, reasoning and problem solving, e.g., executive functioning. There are presently no effective drugs for the treatment of cognitive disorders on the market and there is a great need and demand for drugs effective in the treatment of such disorders.

Cognitive deficits, including impairments in areas such as memory, attention, and executive function, are a major determinant and predictor of long-term disability in schizophrenia. Unfortunately, presently available antipsychotic medications are relatively ineffective in improving cognition.

Schizophrenia is characterized by three broad types of symptom groups, namely, positive symptoms (e.g., hallucinations), negative symptoms (e.g., affective blunting and social withdrawal), and impairments in information processing and cognitive functions (such as, e.g., executive functioning, attention and memory). Executive functioning incorporates processes such as planning, organization, mental flexibility and task coordination and is considered to be the domain in which schizophrenia patients have the most difficulties. Cognitive deficits in schizophrenia are also termed "cognitive impairment associated with schizophrenia" (CIAS). Yet cognitive impairment is observed in many patients prior to onset of psychotic symptoms and/or other clinical features. Furthermore, there is a close link between cognitive impairment and community functioning and unfavorable outcome in patients, and no efficacious treatment of these symptoms has been found yet.

The MATRICS (Measurement and Treatment Research to Improve Cognition in Schizophrenia) initiative in the USA between the National Institute of Mental Health, the University of California, Los Angeles, and the United States Food and Drug Administration, aiming at creating a consensus regarding the nature of cognitive impairments in schizophrenia and how they might be best assessed and treated, has identified seven critical domains of cognition including working memory, attention and vigilance, executive functioning (i.e., reasoning and problem solving), verbal learning, visual learning, speed of processing and social cognition. The current antipsychotics largely treat the positive symptoms of schizophrenia and have limited impact on the negative or cognitive symptoms. Furthermore, many antipsychotics currently on the market even provoke drug induced cognitive impairments. Therefore, there is a real need to develop better therapies to improve the cognitive dysfunction associated with psychosis and schizophrenia.

In some embodiments, the human suffers from cognitive dysfunction. In some embodiments, the human lacks suffering from cognitive dysfunction. In some embodiments, the cognitive dysfunction presents in connection with a disease or disorder selected from the group consisting of psychosis, schizophrenia, a disease involving a psychotic symptom, schizophreniform disorder, schizoaffective disorder, delusional disorder, brief psychotic disorder, shared psychotic disorder, substance-induced psychotic disorder, an affective disorder, ADHD, or a combination thereof. In some embodiments, the affective disorder is depression, mania, or bipolar disorder. In some embodiments, the disease or disorder is schizophrenia. In some embodiments, the disease or disorder is psychosis. In some embodiments, the disease or disorder is ADHD.

In some embodiments, the method further comprises reducing a cognitive symptom in a psychotic patient. In some embodiments, the method further comprises reducing a cognitive symptom in a schizophrenic patient. In some embodiments, the method further comprises reducing a cognitive symptom in an ADHD patient.

In some embodiments, the method is a method of treating cognitive impairment associated with schizophrenia (CIAS), comprising administering an effective amount of a compound of formula to a human in need thereof.

In some embodiments, the method is a method of treating a disease or disorder, comprising administering an effective amount of a compound of formula (I) to a human in need thereof, wherein the disease or disorder is selected from a group consisting of schizophrenia, cognition, cognitive impairment associated with schizophrenia (CIAS), psychosis, depression, mania, bipolar disorder, or a combination thereof.

In some embodiments, the method of improving cognitive function is with respect to cognition related to attention deficit hyperactivity disorder (ADHD).

As used herein, the phrase "affective disorder" refers to any of several psychological disorders characterized by abnormalities of emotional state, such as, without limitation, bipolar disorders, depressive disorders, cyclothymic disorders, dysthymic disorders, mood disorders due to a general medical condition, mood disorders not otherwise specified and substance-induced mood disorders; and as characterized by the *Diagnostic and Statistical Manual of Mental Disorders*, Fourth Edition (DSM-IV) (American Psychiatric Association: Arlington, Va., 1994).

In some such embodiments, the affective disorder is a depression (i.e., a depressive disorder). In some such embodiments, the depression is selected from the group consisting of atypical depression, bipolar depression, unipolar depression, major depression, endogenous depression (i.e., acute depression with no obvious cause), involutional depression (i.e., depression that occurs in mid-life or the elderly), reactive depression (i.e., depression caused by an obvious traumatic life episode), postpartum depression, primary depression (i.e., depression that has no obvious physical or psychological cause such as a medical illness or disorder), psychotic depression, and secondary depression (i.e., depression that seems to be caused by some other underlying condition such another medical illness or disorder).

In some embodiments, at least one symptom of the disease or disorder is treated.

In some such embodiments, the at least one symptom is a symptom of schizophrenia. In some embodiments, the at least one symptom of schizophrenia is a positive symptom selected from the group consisting of hallucination, delusion, paranoia, and a combination thereof. In some such embodiments, the symptom of schizophrenia is a negative symptom selected from the group consisting of social withdrawal, flat affect, anhedonia, decreased motivation, and a combination thereof. In some such embodiments, the symptom of schizophrenia is a cognitive symptom selected from the group consisting of severe deficit in attention, severe deficit in object naming, severe deficit in working memory, severe deficit in long-term memory storage, severe deficit in executive functioning, a slowing of information processing, a slowing of neural activity, long term depression, and a combination thereof. In some such embodiments, the at least one symptom is a symptom of ADHD. In some embodiments, the at least one symptom of ADHD is a symptom selected from the group consisting of inattention, hyperactivity and impulsivity.

Another aspect of invention is the use of a compound of formula (I) for use in the preparation of a medicament. In some embodiments, the compound of formula (I) is used in the preparation of a medicament for treatment of a disease or disorder as previously described herein. In some embodiments, the compound of formula (I) is used in the preparation of a medicament for improving cognitive functioning. In some embodiments, the cognitive dysfunction presents in connection with a disease or disorder selected from the group consisting of psychosis, schizophrenia, a disease involving a psychotic symptom, schizophreniform disorder, schizoaffective disorder, delusional disorder, brief psychotic disorder, shared psychotic disorder, substance-induced psychotic disorder, an affective disorder, ADHD, or a combination thereof. In some embodiments, the affective disorder is depression, mania, or bipolar disorder. In some embodiments, the disease or disorder is schizophrenia. In some embodiments, the disease or disorder is ADHD. In some embodiments, the medicament further comprises reducing a cognitive symptom in a schizophrenic patient or ADHD patient. In some embodiments, the compound of formula (I) is used in the preparation of a medicament for the treatment of schizophrenia, cognition, cognitive impairment associated with schizophrenia (CIAS), psychosis, depression, mania, bipolar disorder, ADHD, or a combination thereof.

In some embodiments, the compound of formula (I) is for use in treating a disease or disorder selected from the group consisting of psychosis, schizophrenia, a disease involving a psychotic symptom, schizophreniform disorder, schizoaffective disorder, delusional disorder, brief psychotic disorder, shared psychotic disorder, substance-induced psychotic disorder, an affective disorder, ADHD, or a combination thereof. In some embodiments, the compound of formula (I) is used in treating schizophrenia, cognition, cognitive impairment associated with schizophrenia (CIAS), psychosis, depression, mania, bipolar disorder, ADHD, or a combination thereof. In some embodiments, the compound of formula (I) is used in treating a cognitive symptom in a schizophrenic patient or ADHD patient.

Another aspect of the present invention is a process for producing the compounds of formula (I).

Preparation of the Compounds of the Present Invention

The compounds of the present invention may be prepared, without limitation, according to one of the general methods outlined below. For example, Schemes 1-9 that follow are intended as an illustration of some embodiments of the invention and no limitation of the present invention is implied because of them.

The following defines acronyms as used herein unless specified otherwise in a particular instance.
ACN=Acetonitrile, CAS No. 75-05-8
n-BuLi=n-Butyllithium
CDI=N,N'-Carbonyldiimidazole, CAS No. 530-62-1
CuI=Copper (I) Iodide
$dH_2O$=Deionized water
DCE=1,2-Dichloroethane
DCM=Dichloromethane or methylene chloride
DMF=Dimethyl formamide
DMSO=Dimethyl sulfoxide
EDC-HCl=N-Ethyl-N'-(3-dimethylaminopropyl)carbodiimide hydrochloride, CAS No. 25952-53-8
$Et_2NH$=Diethylamine
HATU=(2-(7-Aza-1H-benzotriazole-1-yl)-1,1,3,3-tetramethyluronium hexafluorophosphate), CAS No. 148893-10-1
HBTU=2-(1H-Benzotriazole-1-yl)-1,1,3,3-Tetramethyluronium hexafluorophosphate, CAS No. 94790-37-1
4M HCl=4 Molar Hydrochloric acid
HOBT=1-Hydroxybenzotriazole anhydrous, CAS No. 2592-95-2
$K_2CO_3$=Potassium carbonate
KF=Potassium fluoride
LiOH=Lithium hydroxide
MeMgBr=Methyl Magnesium bromide
$NaBH_4$=Sodium borohydride
NaH=Sodium hydride
$NaBH(OAc)_3$=Sodium triacetoxyborohydride
$Na_2SO_4$=Sodium sulfate
PDC=Pyridinium dichromate, CAS No. 26299-14-9.
$PdCl_2(PPh_3)_2$=Palladiun (II) dichlorobis(triphenyl phosphine)
PyBOP=Benzotriazol-1-yl-oxytripyrrolidinophosphonium hexafluorophosphate, CAS No. 128625-52-5
RT=room temperature or retention time, as the case may be.
rt=room temperature
TEA=triethylamine, CAS No. 554-68-7
TFA=trifluoroacetic acid, CAS No. 76-05-1
THF=tetrahydrofuran, CAS No. 109-99-9
$Ti(OiPr)_4$=Titanium (IV) tetraisopropoxide 2-substituted-ethynyl thiazole-4-(or 5-)carboxamides of formula (Ia) can be prepared via the process outlined in Scheme 1 using customary coupling procedures from starting compound 1, where $R^1$-$R^4$ are as previously defined herein.

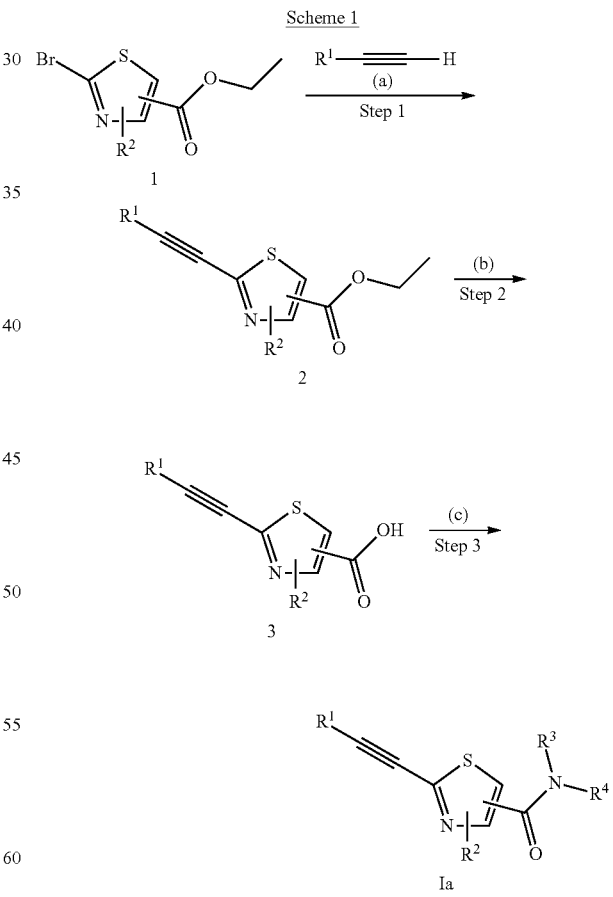

Reagents and Conditions: (a) $(Ph_3P)_2PdCl_2$, CuI, TEA, THF; (b) LiOH, THF, $H_2O$; (c) Amide Coupling: Method A: CDI, $R^3R^4NH$, TFA; Method B: CDI, $R^3R^4NH\cdot HCl$, TEA; Method C: PyBOP, $R^3R^4NH$; Method D: $R^3R^4NH\cdot HOBT$, EDC-HCl, TEA; Method E: $R^3R^4NH$, HBTU, DIEA.

2-substituted-ethynylthiazole-4-(or 5-)carboxamides of formula (Ia) also can be prepared via the process outlined in Scheme 2 using customary coupling procedures from compound 4, where $R^1$-$R^4$ are as previously defined herein.

be prepared via the process outlined in Scheme 3 using customary coupling and synthetic chemistry procedures from starting thiazolyl-carboxaldehydes 6, where $R^1$-$R^6$ are as previously defined herein.

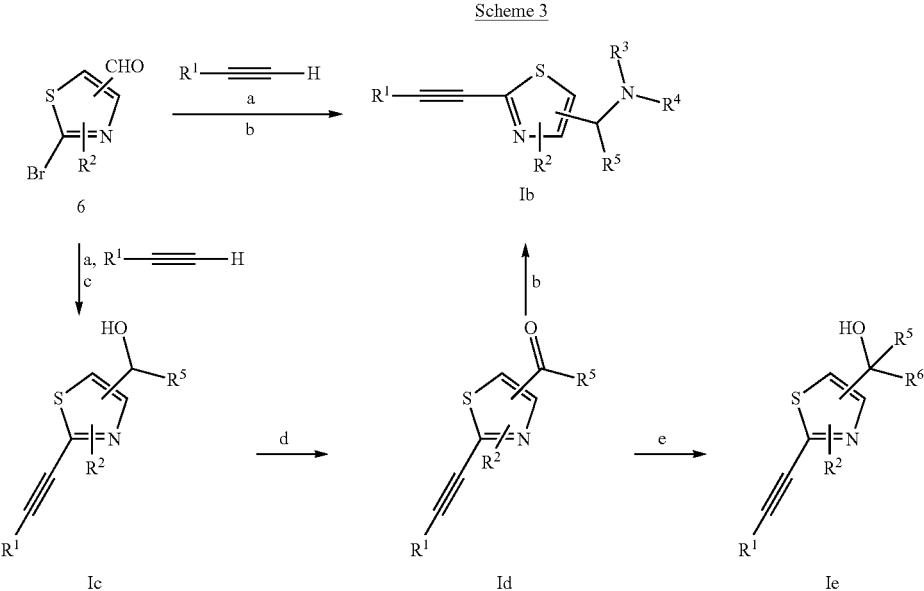

Scheme 3

Reagents and Conditions: (a) (Ph₃P)₂PdCl₂, CuI, TEA, THF; (b) HNR³R⁴, THF, 1 h, then NaBH(OAc)₃ or HNR³R⁴, Benzotriazole, EtOH then THF, R⁵MgBr or HNR³R⁴, Ti(OiPr)₄/NaBH₄; (c) R⁵MgBr, THF (d) PDC, DCM; (e) R⁶MgBr, THF

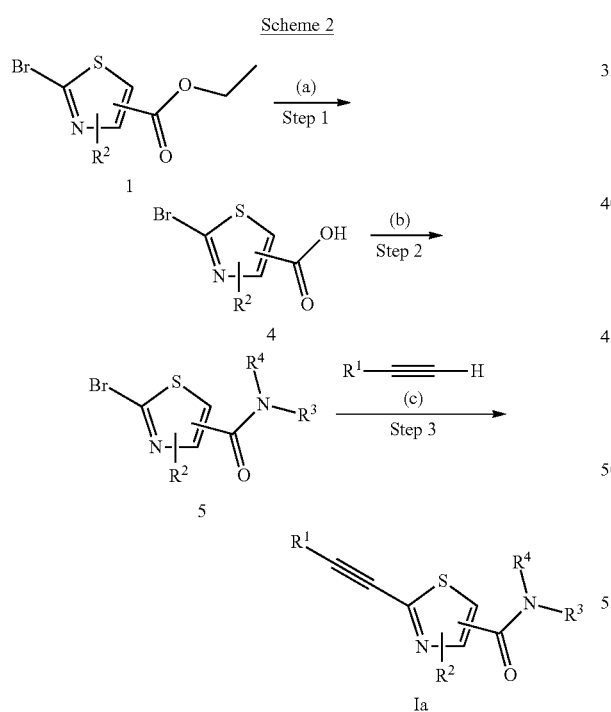

Scheme 2

Reagents and Conditions: (a) LiOH, THF/H₂O; (b) HBTU, DCM, R⁴R³NH, rt; and (c) (Ph₃P)₂PdCl₂, CuI, TEA, THF 2-substituted-ethynylthiazole-4-(or 5-)-aminomethyl compounds of formula (Ib), 2-substituted-ethynylthiazole-4-(or 5-)-alcohols of formula (Ic), 2-substituted-ethynylthiazole-4-(or 5-)-methanones of formula (Id), and 2-substituted-ethynylthiazole-4-(or 5-)-tertiary alcohols of formula (Ie) can Fluoro-substituted alkynyl-thiazole-5-carboxamides of formula (Ia-i) can be prepared via the process outlined in Scheme 4 using customary coupling procedures from starting compound 7, where $R^1$, $R^3$-$R^4$ are as previously defined herein.

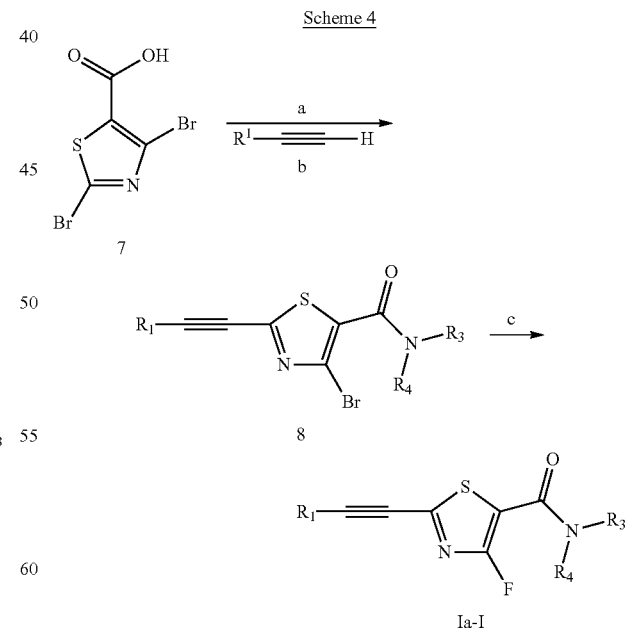

Scheme 4

Reagents and Conditions: (a) HNR³R⁴, CDI, THF or HNR³R⁴ HBTU, DCM, Et₃N; (b) (Ph₃P)₂PdCl₂, CuI, TEA, THF; (c) n-BuLi, 25° C. to -78° C.; (PhSO₂)₂NF or KF, Kryptofix, K₂CO₃, DMSO, heat

EXPERIMENTAL SECTION

1) General Methods

Unless specifically stated otherwise, the experimental procedures were performed under the following conditions. All operations were carried out at room temperature (about 18° C. to about 25° C.) under nitrogen atmosphere. Evaporation of solvent was carried out using a rotary evaporator under reduced pressure or in a high performance solvent evaporation system HT-4X (Genevac Inc., Gardiner, N.Y., USA). The course of the reaction was followed by thin layer chromatography (TLC) or liquid chromatography-mass spectrometry (LC-MS), and reaction times are given for illustration only. Silica gel chromatography was carried out on a CombiFlash® system (Teledyne Isco, Inc., Lincoln, Nebr., USA) with prepacked silica gel cartridge or performed on Merck silica gel 60 (230-400 mesh) (Merck KGaA, Darmstadt, Germany). The structure and purity of all final products was assured by at least one of the following analytical methods: nuclear magnetic resonance (NMR) and LC-MS.

a) NMR

NMR spectra was recorded on a Bruker Avance™ 300 spectrometer (Bruker BioSpin Corp., Billerica, Mass., USA) or a Varian UNITY INOVA® 400 (Varian, Inc., Palo Alto, Calif., USA) using the indicated solvent. Chemical shift ($\delta$) is given in parts per million (ppm) relative to tetramethylsilane (TMS) as an internal standard. Coupling constants (J) are expressed in hertz (Hz), and conventional abbreviations used for signal shape are: s=singlet; d=doublet; t=triplet; m=multiplet; br=broad; etc.

b) LC/MS

Unless specifically stated otherwise, the LC/MS procedures were performed under one of the following methods using electrospray ionization (ESI) operating in positive mode via a Micromass® Platform II system, a Quattro Micro™ system or Waters ZQ (Waters Corp.) mass spectrometer (all from Waters Corp., Milford, Mass., USA), an Agilent 1100 LC pump (Agilent Technologies, Inc., Santa Clara, Calif.), and Agilent 1100 autosampler, with a 200 µl/min split to the ESI source with inline Agilent 1100 diode array detector (DAD) and variable wavelength detector (VWD) at 254 nm, and an 800 ul/min split to a Waters evaporative light scattering detector (ELSD). From mass spectra obtained, $(M+H)^+$ are reported. From chromatographic spectra obtained, retention times in minutes (RT) are reported.

Method 1—Mobile phase: A) water/acetonitrile (99/1) and 0.2% ammonium formate; B) acetonitrile. Gradient: 20-85% B from 0 to 1.7 min, 85% B from 1.7 to 1.84 min, 85-100% B from 1.84 to 1.85 min, 100% B from 1.85-1.99 min, then 100-20% B from 1.99 to 2 min. Cycle time: 2 min. Flow rate: 5.0 mL/min. Column: Inertsil® ODS-3, 50×4.6 mm, 3 µm particle size (GL Sciences, Tokyo, Japan)).

Method 2—Mobile phase: A) water/acetonitrile (99/1) and 0.2% ammonium formate; B) acetonitrile. Gradient: 30-90% B from 0 to 1.7 min, 90% B from 1.7 to 1.84 min, 90-100% B from 1.84 to 1.85 min, 100% B from 1.85-1.99 min, 100-20% B from 1.99 to 2 min. Cycle time: 2 min. Flow rate: 5.0 mL/min. Column: Inertsil® C8, 50×4.6 mm, 3 µm particle size (GL Sciences).

Method 3—Mobile phase: A) water/acetonitrile (99/1) and 0.2% ammonium formate; B) acetonitrile. Gradient: 10-85% B from 0 to 1.7 min, 85% B from 1.7 to 1.84 min, 85-100% B from 1.84 to 1.85 min, 100% B from 1.85-1.99 min, 100-20% B from 1.99 to 2 min. Cycle time: 2 min. Flow rate: 5.0 mL/min. Column: Inertsil® C8, 50×4.6 mm, 3 µm particle size.

Method 4—Mobile phase: A) water/acetonitrile (99/1) and 0.2% acetic acid; B) acetonitrile Gradient: 0-30% B from 0 to 1.3 minutes, 30-85% B from 1.3 to 1.7 min, 85% B from 1.7-1.84 min, 85-100% B from 1.84 to 1.85 min, 100% B from 1.85 to 1.99 min, and 100-20% B from 1.99 to 2.00 min. Cycle time: 2 min. Flow rate: 5.0 mL/min. Column: Inertsil® ODS-3, 50×4.6 mm, 3 µm particle size.

The following LC/MS procedures were performed using atmospheric pressure photoionization (APPI) operated with positive polarity via an API150ex single quadrupole mass spectrometer (Applied Biosystems, Foster City, Calif., USA) with ion monitoring between 100 and 1000 amu and further settings of: OR/RNG 20/200 V; OR/RNG 5/100 V; temperature 450° C.; a Shimadzu LC10ADvp LC pumps (3×), Shimadzu SPD-M20A photodiode array detector at 254 nm, Shimadzu CBM-20A system controller (all from Shimadzu Corp., Kyoto, Japan), a Gilson 215 autosampler, a Gilson 864 degasser (both from Gibson, Inc., Middleton, Wis., USA) and SEDERE SEDEX 85 ELSD (Sedere Sas, Alfortville Cedex, France) with settings of: glass tube: 21° C., evaporation chamber: 50° C., and pressure: 4.4 bar. The system is controlled by Analyst® software (Applied Biosystems). From mass spectra obtained, $(M+H)^+$ are reported. From chromatographic spectra obtained, retention times in minutes (RT) are reported.

Method 5—Gradient: $ACN:H_2O$ (95:5) in water, 10-100% in 2.4 min., then to 10% in 0.4 min., in a cycle time of 2.8 min. Flow rate: 3.3 mL/min. Mobile phase additive: 0.05% TFA. Column: Symmetry C-18, 4.6×30 mm, 3.5 µm particle size (Waters Corp.), at 60° C.

Method 6—Gradient: $ACN:H_2O$ (95:5) in water, 10-100% in 2.4 min., then to 10% in 0.4 min., in a cycle time of 2.8 min. Flow rate: 3.3 mL/min. Mobile phase additive: 0.05% TFA. Column: Symmetry C-18, 4.6×30 mm, 3.5 µm particle size (Waters Corp.), at 60° C.

Method 7—Mobile phase: A) water/acetonitrile (90/10) and 0.05% TFA or 0.05% HCOOH or 10 molar $NH_4OAc$; B) acetonitrile; Gradient: 0-10% B in 0.01 min, 30-70% B from 0.01-1.5 min, 90% B from 1.5-3.0 min, 90% B from 3.00-4.00 min, 90-10% B from 4.00-5.00 min. Cycle time: 5 min or 8 min. Flow rate: 1.2 mL/min. Column: Phenomenex GEMINI 5 µm C18 110A (50×4.6 mm). Injection volume: 1.00 to 5.00 µl; UV wavelength: 220 and 260 nm.

2) Preparation of Intermediates of the Invention

Unless specified otherwise, the reagents used in the preparation of compounds, including intermediates, of the present invention were purchased from Sigma-Aldrich Corporation (St. Louis, Mo., USA) and/or its subsidiaries, such as Fluka Chemie AG (Buchs, Switzerland) and Aldrich Chemical Company, Inc. (Milwaukee, Wis., USA). Substituted 2-bromo and 2-chlorothiazoles are either commercially available, or can be prepared as described previously in, for example, [Barton, Anne, et. al., *J. Chem. Soc. Perkin Trans* 1: *Org. and Bioorg Chem* (1972-1999), 1, 159-164, 1982; Cui, Yong-Mei, et. al., *Bioorg and Med Chem. Lett.,* 2005, 15 (16), 3732-3736; Lumb, K. and Decarr, L., PCT Int. Appl., WO2006091506, 31 Aug., 2006; Barda, David Anthony, et. al., PCT Int. Appl., WO2006091671, 31 Aug. 2006; and Whelan, James, et. al., PCT Int. Appl., WO2006121860, 16 Nov. 2006.]

Intermediate 14:
2-Phenylethynyl-thiazole-5-carboxylic acid

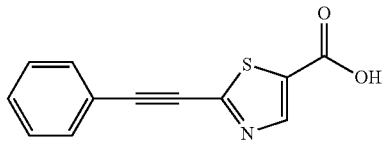 [SMILES: O=C(O)c1cnc(C#Cc2ccccc2)s1]

Intermediate—14 was prepared via the process of Scheme 1, supra, as follows:

Step 1: Intermediate—2:
2-Phenylethynyl-thiazole-5-carboxylic acid ethyl ester

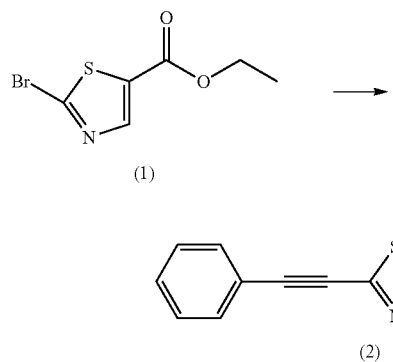

A solution of phenylacetylene (6.15 ml, 55.9 mmol), ethyl 2-bromothiazole-5-carboxylate (7.59 ml, 50.8 mmol), bis(triphenylphosphine)palladium(II) chloride (1.07 g, 1.52 mmol), copper (I) iodide (581 mg, 3.05 mmol), triethylamine (100 ml, 717 mmol) and tetrahydrofuran (225 mL) was stirred at 25° C. for 16 h. The reaction was worked up by concentrating to remove the THF and taken up in 400 mL of CHCl$_3$. The CHCl$_3$ was washed with 2×75 mL of 3.7% aq. HCl, 75 mL of brine, and dried (Na$_2$SO$_4$). The material was purified by silica gel chromatography using a gradient elution going from 4.5% to 8.5% EtOAc in hexanes over 30 minutes to give the titled compound, 2-phenylethynyl-thiazole-5-carboxylic acid ethyl ester (9.5 g, 73% yield), as a solid, which was used without further purification in the next step.

The following intermediates (3-13) were prepared in a similar fashion as described for 2-phenylethynyl-thiazole-5-carboxylic acid ethyl ester:

Intermediate—3: 4-Methyl-2-phenylethynyl-thiazole-5-carboxylic acid ethyl ester. LC/MS (Method 4), RT=1.39 min. Calculated [M+H]$^+$=271; Observed [M+H]$^+$=272

Intermediate—4: 2-(2-Fluorophenyl)ethynyl-thiazole-5-carboxylic acid ethyl ester. LC/MS (Method 3), RT=1.58 min. Calculated [M+H]$^+$=276; Observed [M+H]$^+$=276

Intermediate—5: 2-(3-Fluorophenyl)ethynyl-thiazole-5-carboxylic acid ethyl ester. LC/MS (Method 3), RT=1.60 min. Calculated [M+H]$^+$=276; Observed [M+H]$^+$=276

Intermediate—6: 2-(4-Fluorophenyl)ethynyl-thiazole-5-carboxylic acid ethyl ester. LC/MS (Method 1), RT=1.59 min. Calculated [M+H]$^+$=275.9; Observed [M+H]$^+$=275.9

Intermediate—7: 2-(2-Chlorophenyl)ethynyl-thiazole-5-carboxylic acid ethyl ester. LC/MS (Method 3), RT=1.66 min. Calculated [M+H]$^+$=291.9; Observed [M+H]$^+$=291.9

Intermediate—8: 2-(3-Chlorophenyl)ethynyl-thiazole-5-carboxylic acid ethyl ester. LC/MS (Method 3), RT=1.70 min. Calculated [M+H]$^+$=291.9; Observed [M+H]$^+$=291.9

Intermediate—9: 2-(4-Chlorophenyl)ethynyl-thiazole-5-carboxylic acid ethyl ester. LC/MS (Method 3), RT=1.65 min. Calculated [M+H]$^+$=291.9; Observed [M+H]$^+$=291.9

Intermediate—10: 2-(2-Methylphenyl)ethynyl-thiazole-5-carboxylic acid ethyl ester. LC/MS (Method 3), RT=1.67 min. Calculated [M+H]$^+$=272; Observed [M+H]$^+$=272.0

Intermediate—11: 2-(3-Methylphenyl)ethynyl-thiazole-5-carboxylic acid ethyl ester. LC/MS (Method 3), RT=1.69 min. Calculated [M+H]$^+$=272.0; Observed [M+H]$^+$=272.0

Intermediate—12: 2-(4-Methylphenyl)ethynyl-thiazole-5-carboxylic acid ethyl ester. LC/MS (Method 3), RT=1.67 min. Calculated [M+H]$^+$=272.0; Observed [M+H]$^+$=272.0

Intermediate—13: 2-Phenylethynyl-thiazole-4-carboxylic acid methyl ester. LC/MS (Method 2), RT=1.01 min. Calculated [M+H]$^+$=243; Observed [M+H]$^+$=243.9

Step 2: Intermediate—14:
2-Phenylethynyl-thiazole-5-carboxylic acid

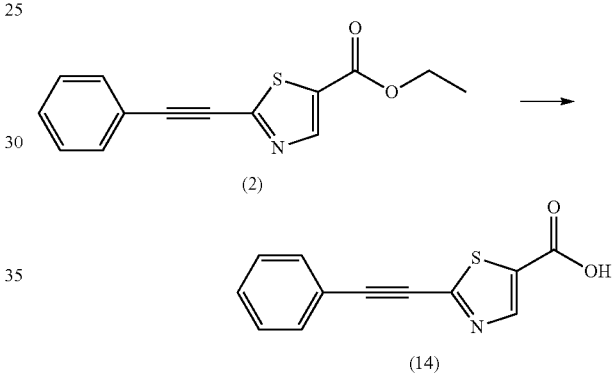

A solution of 2-phenylethynyl-thiazole-5-carboxylic acid ethyl ester (9.00 g, 35.0 mmol), lithium hydroxide (13.5 g, 563 mmol), tetrahydrofuran (190 mL) and water (143 mL) was stirred at 25° C. for 64 h. The material was concentrated to remove most of the THF, taken up in 350 mL of water and washed with EtOAc (3×50 mL); acidified with 3.7% HCl to pH<1 and the precipitate extracted with 3×100 mL of EtOAc. The combined EtOAc extracts were washed with 50 mL of water, 50 mL of brine, dried (Na$_2$SO$_4$) and concentrated to give the titled compound, 2-phenylethynyl-thiazole-5-carboxylic acid (7.79 g; 97%), as a yellow powder, which was used without further purification in the next step. $^1$H NMR (400 MHz, DMSO-d$_6$) δ 8.53 (s, 1H), 7.69-7.60 (m, 2H), 7.51-7.38 (m, 3H). LC/MS (Method 1), RT=0.57 min. Calculated [M+H]$^+$=230; Observed [M+H]$^+$=230.

The following intermediates (15-26) were prepared in a similar fashion as described for 2-phenylethynyl-thiazole-5-carboxylic acid (Intermediate—14):

Intermediate—15: 4-Methyl-2-phenylethynyl-thiazole-5-carboxylic acid. LC/MS (Method 1), RT=0.61 min. Calculated [M+H]$^+$=244; Observed [M+H]$^+$=244

Intermediate—16: 2-(2-Fluorophenyl)ethynyl-thiazole-5-carboxylic acid. LC/MS (Method 3), RT=0.80 min. Calculated [M+H]$^+$=247.9; Observed [M+H]$^+$=247.9

Intermediate—17: 2-(3-Fluorophenyl)ethynyl-thiazole-5-carboxylic acid. LC/MS (Method 3), RT=0.82 min. Calculated [M+H]$^+$=247.9; Observed [M+H]$^+$=247.9

Intermediate—18: 2-(4-Fluorophenyl)ethynyl-thiazole-5-carboxylic acid. LC/MS (Method 3), RT=0.81 min. Calculated [M+H]$^+$=247.9; Observed [M+H]$^+$=247.9

Intermediate—19: 2-(2-Chlorophenyl)ethynyl-thiazole-5-carboxylic acid. LC/MS (Method 3), RT=0.87 min. Calculated [M+H]$^+$=263.9; Observed [M+H]$^+$=263.9

Intermediate—20: 2-(3-Chlorophenyl)ethynyl-thiazole-5-carboxylic acid. LC/MS (Method 3), RT=0.92 min. Calculated [M+H]$^+$=263.9; Observed [M+H]$^+$=263.9

Intermediate—21: 2-(4-Chlorophenyl)ethynyl-thiazole-5-carboxylic acid. LC/MS (Method 3), RT=0.91 min. Calculated [M+H]$^+$=263.9; Observed [M+H]$^+$=263.9

Intermediate—22: 2-(2-Methylphenyl)ethynyl-thiazole-5-carboxylic acid. LC/MS (Method 3), RT=0.87 min. Calculated [M+H]$^+$=244.0; Observed [M+H]$^+$=244.0

Intermediate—23: 2-(3-Methylphenyl)ethynyl-thiazole-5-carboxylic acid. LC/MS (Method 3), RT=0.89 min. Calculated [M+H]$^+$=244.0; Observed [M+H]$^+$=244.0

Intermediate—24: 2-(4-Methylphenyl)ethynyl-thiazole-5-carboxylic acid. LC/MS (Method 3), RT=0.88 min. Calculated [M+H]$^+$=243.9; Observed [M+H]$^+$=243.9

Intermediate—25: 2-Phenylethynyl-thiazole-4-carboxylic acid. LC/MS (Method 2), RT=0.31 min. Calculated [M+H]$^+$=229; Observed [M+H]$^+$=229

Intermediate—26: 2-(3,5-Difluoro-phenylethynyl)-thiazole-5-carboxylic acid. LC/MS (Method 7, RT=2.60. Calculated [M+H]$^+$=266; Observed [M+H]$^+$=266

Synthesis of Intermediate—27:
(2-Bromo-thiazol-5-yl)-piperidin-1-yl-methanone

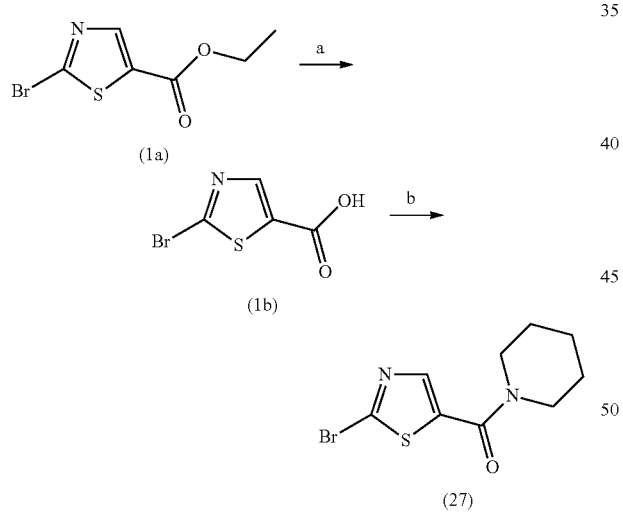

Reagents and Conditions: (a) 1N NaOH, rt and (b) HBTU, Piperidine, DCM, DIEA, rt Step 1: Preparation of intermediate—1b A solution of sodium hydroxide in water (1N, 150 mL) was added to ester (1a) (25 g, 106 mmol). The reaction mass was stirred at 23° C. for 1.5 h. The reaction mass was washed with diethyl ether. The aqueous phase was acidified with 2N HCl upto pH 2. The solid precipitated out was filtered and dried under vacuum to afford intermediate carboxylic acid (1b) (19 g, 86%).

Step 2: Preparation of Intermediate—27

To a stirred solution of acid 1b (10 g, 48 mmol) in DCM (150 mL) was added DIPEA (28 mL, 190 mmol) and HBTU (23 g, 60 mmol) at 0° C. The reaction mass was allowed to stir for 15 min. To it was added piperidine (5.7 mL, 50 mmol). The reaction mass was allowed to stir at 23° C. for 4 h. The reaction mass was diluted with DCM, washed with saturated sodium bicarbonate solution, ammonium chloride solution and brine. The organic phase was dried over anhydrous sodium sulfate and concentrated to dryness. The crude residue was purified by flash column chromatography to afford titled intermediate 27 (7 g, 53%). $^1$H NMR (400 MHz, CDCl$_3$) δ 7.94 (s, 1H), 3.56 (t, J=5.0 Hz, 4H), 1.62-1.54 (m, 6H). LCMS (Method 7), RT=3.14 min. Calculated [M+H]$^+$=274; Observed [M+H]$^+$=275.

The following intermediates (28-31) were prepared in a similar fashion as described for (2-Bromo-thiazol-5-yl)-piperidin-1-yl-methanone (Intermediate—27):

Intermediate—28: (2-Bromo-thiazol-5-yl)-(4-fluoro-piperidin-1-yl)-methanone. LCMS (Method 7), RT=5.17 min. Calculated [M+H]$^+$=293; Observed [M+H]$^+$=293. Yield=71%.

Intermediate—29: (2-Bromo-thiazol-5-yl)-(3-fluoro-piperidin-1-yl)-methanone. LCMS (Method 7), RT=3.18 min. Calculated [M+H]$^+$=293; Observed [M+H]$^+$=293. Yield=43%.

Intermediate—30: (2-Bromo-thiazol-5-yl)-morpholin-4-yl-methanone. LCMS (Method 7), RT=3.05 min. Calculated [M+H]$^+$=277; Observed [M+H]$^+$=277. Yield=38%.

Intermediate—31: (2-Bromo-thiazol-5-yl)-pyrrolidin-1-yl-methanone. LCMS (Method 7), RT=3.43 min. Calculated [M+H]$^+$=261; Observed [M+H]$^+$=261. Yield=41%.

Scheme 5: Synthesis of Intermediate (34a)

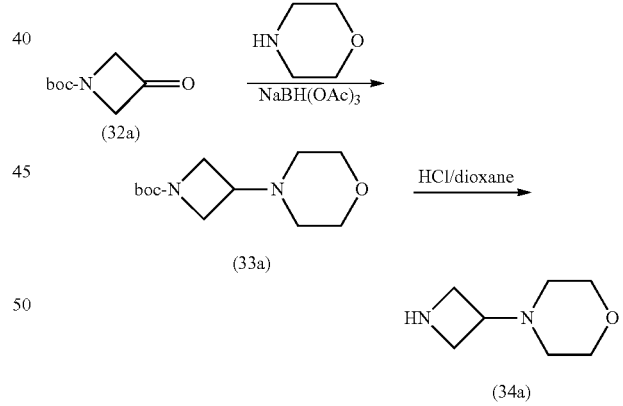

Step—1: Preparation of intermediate—33a

To a stirred solution of n-BOC azetidinone (32a) (500 mg, 2.92 mmol) in DCE (5 mL) was added morpholine (280 μL, 3.21 mmol) and catalytic acetic acid at 0° C. The reaction mass was stirred at 23° C. for 3 h. To it was added sodium triacetoxyborohydride (870 mg, 4.09 mmol) at 23° C. The reaction mass was stirred at 23° C. for 12 h. The reaction mass was partitioned between DCM and water. The organic phase was washed with saturated sodium bicarbonate solution, water and brine, dried over anhydrous sodium sulfate and concentrated to dryness. The crude residue was purified by flash column chromatography to afford intermediate 33a (400 mg, 57%)

Step—2: Preparation of intermediate—34a

To a stirred solution of intermediate 33a (400 mg, 1.65 mmol) in 1,4-dioxane (5 mL) was added 4M HCl in 1,4-dioxane (8 mL) at 0° C. The reaction mass was stirred for 2 h at 23° C. The organics were evaporated off under reduced pressured. The residue was washed with dry ether and dried under vacuum to afford intermediate 34a (230 mg, >99%) as its HCl salt.

Intermediates (34b-34y) were prepared in an analogous manner to intermediate 34a as described in Scheme 5 or were commercially available:

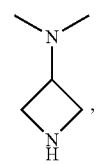
(34b)

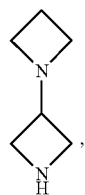
(34c)

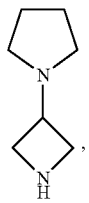
(34d)

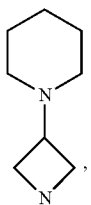
(34e)

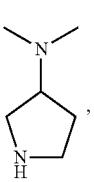
(34f)

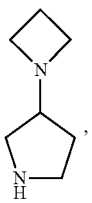
(34g)

-continued

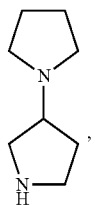
(34h)

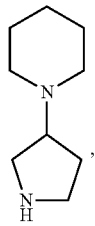
(34i)

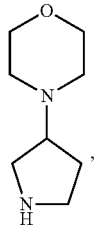
(34j)

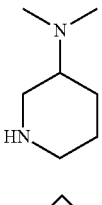
(34k)

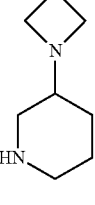
(34l)

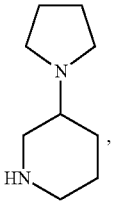
(34m)

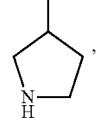
(34n)

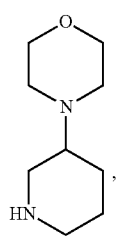 (34o)
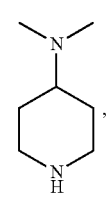 (34p)
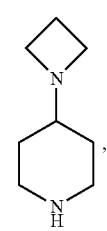 (34q)
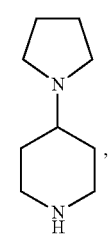 (34r)
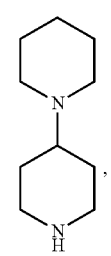 (34s)
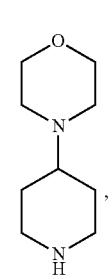 (34t)
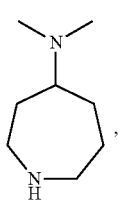 (34u)
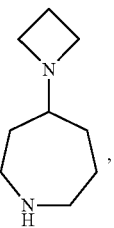 (34v)
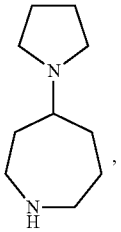 (34w)
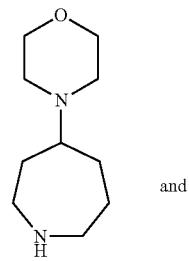 and (34x)
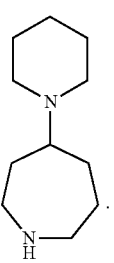 . (34y)
Scheme 6: Synthesis of Intermediate (38a)
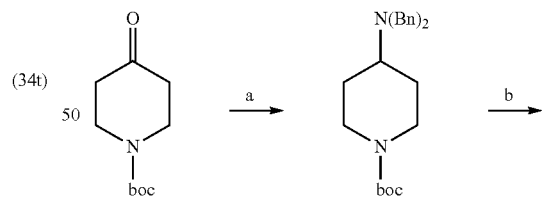
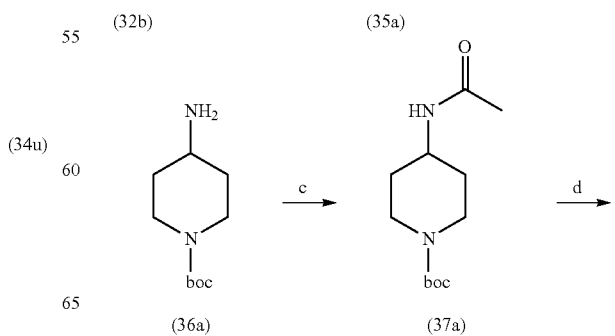

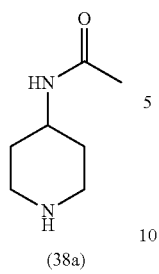

(38a)

Reagents and Conditions: (a) Bn₂NH, cat. AcOH, rt, then NaBH(OAc)₃, rt; (b) Pd(OH)₂, H₂, EtOH—THF, rt; (c) AcCl, rt and (d) 4M HCl in dioxane, rt

Step-1: Preparation of intermediate—35a

To a stirred solution of intermediate 32b (1 g, 5.03 mmol) in DCM (20 mL) was added dibenzylamine (1.09 g, 5.53 mmol) and catalytic acetic acid at 0° C. The reaction mass was stirred at 23° C. for 3 h. To it was added sodium triacetoxyborohydride (1.5 g, 7.04 mmol) at 23° C. The reaction mass was stirred at 23° C. for 12 h. The reaction mass was partitioned between DCM and water. The organic phase was washed with saturated sodium bicarbonate solution, water and brine, dried over anhydrous sodium sulfate and concentrated to dryness. The crude residue was purified by flash column chromatography to afford intermediate 35a (1.2 g, 63%).

Step-2: Preparation of intermediate—36a

To a deoxygenated solution of intermediate 35a (1 g, 2.63 mmol) in ethanol:THF (1:1, 20 mL) was added palladium hydroxide (500 mg) under argon atmosphere. The reaction mass was subjected to hydrogenation under atmospheric pressure and at 23° C. for 6 h. The reaction mass was filtered through a bed of celite and washed with ethanol. The filtrate was evaporated to dryness under reduced pressure to afford intermediate 36a (400 mg, 77%).

Step—3: Preparation of intermediate—37a

Acetyl chloride (150 μL, 2.1 mmol) was added to a solution of intermediate 36a (400 mg, 2 mmol) in DCM (10 mL) at 0° C. The reaction mass was stirred at 23° C. for 2 h. The reaction mass was partitioned between DCM and water. The organic phase was washed with brine, dried over anhydrous sodium sulfate and concentrated to dryness to afford intermediate 37a (350 mg, 73%)

Step—4: Preparation of intermediate—38a

To a stirred solution of intermediate 37a (350 mg, 1.4 mmol) in 1,4-dioxane (5 mL) was added 4M HCl in 1,4-dioxane (8 mL) at 0° C. The reaction mass was stirred for 2 h at 23° C. The organics were evaporated off under reduced pressured. The residue was washed with dry ether and dried under vacuum to afford intermediate 38a (200 mg, >99%) as its HCl salt.

Intermediates (38b-38e) were prepared in an analogous manner to intermediate (38a) as described in Scheme 6:

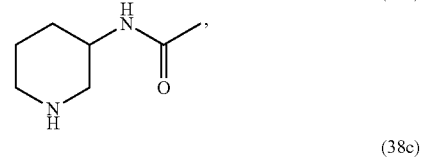
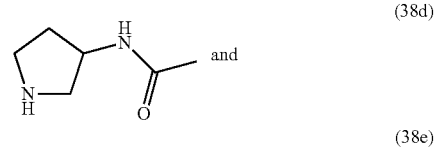

Scheme 7: Synthesis of Intermediate (41a)

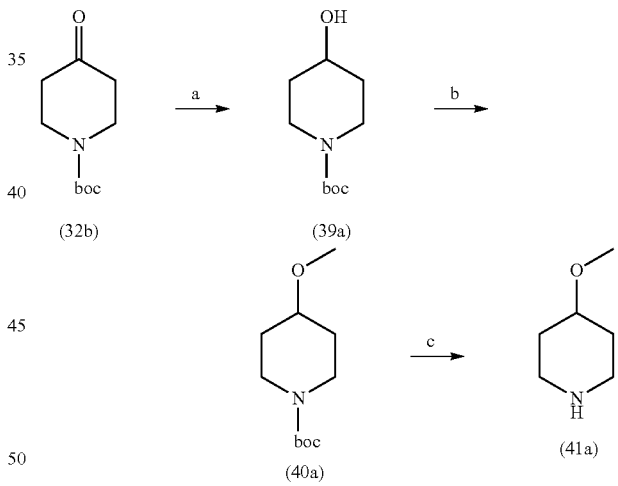

Reagents and Conditions: (a) NaBH₄, EtOH, rt; (b) NaH, DMF, MeI and (c) 4M HCl in dioxane, rt

Step—1: Preparation of intermediate—39a

To a stirred solution of intermediate 32b (1.5 g, 7.53 mmol) in ethanol (20 mL) was added sodium borohydride (427 mg, 11.3 mmol) at 0° C. The reaction mass was stirred at 23° C. for 30 min. The ethanol was evaporated off under reduced pressure. The residue was partitioned between ethyl acetate and water. The organic layer was washed with brine, dried over anhydrous sodium sulfate and concentrated to dryness. The crude residue was purified by flash column chromatography to afford intermediate 39a (1 g, 67%).

Step—2: Preparation of intermediate—40a

To a stirred solution of intermediate 39a (1 g, 4.97 mmol) in DMF (6 mL) was added sodium hydride (60% in mineral oil, 600 mg, 14.92 mmol) at 0° C. The reaction mass was stirred for 30 min. to the reaction mass was added methyl iodide (930 μL, 14.9 mmol) at 0° C. The reaction mass was stirred at 23° C. for 2 h. The reaction mass was diluted with water and extracted with ethyl acetate. The organic layer was washed with water and brine, dried over anhydrous sodium sulfate and concentrated to dryness. The residue was purified by flash column chromatography to afford intermediate 40a (810 mg, 81%).

Step—3: Preparation of intermediate—41a

To a stirred solution of intermediate 40a (810 mg, 3.76 mmol) in 1,4-dioxane (5 mL) was added 4M HCl in 1,4-dioxane (8 mL) at 0° C. The reaction mass was stirred for 2 h at 23° C. The organics were evaporated off under reduced pressured. The residue was washed with dry ether and dried under vacuum to afford intermediate 41a (430 mg, >99%) as its HCl salt.

Intermediates (41b-41e) were prepared in an analogous manner to intermediate 41a as described in Scheme 7:

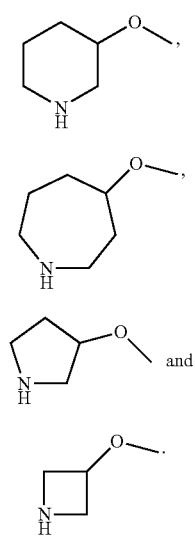

(41b)

(41c)

(41d) and (41e)

Scheme: 8 Preparation of Intermediate (45a)

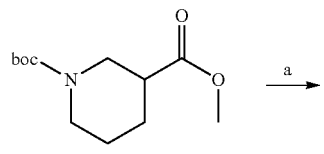

(42)

(43a)

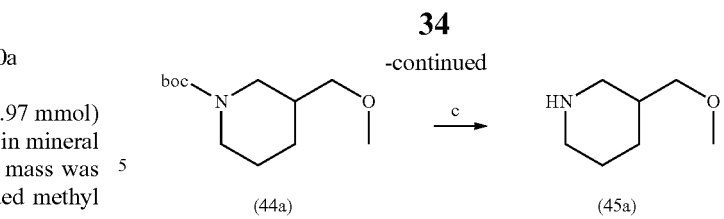

(44a)    (45a)

Reagents and Conditions: (a) LAH, THF, 0° C.; (b) NaH, DMF, MeI and (c) 4M HCl in dioxane

Step—1: Preparation of intermediate—43a

To a stirred solution of intermediate 42 (750 mg, 3.08 mmol) in THF (10 mL) was added a solution of lithium aluminum hydride in THF (1 M in THF, 2.16 mL) at 0° C. The reaction mass was stirred at 0° C. for 2 h. The reaction mass was quenched with sodium sulfate decahydrate. The reaction mass was filtered through a bed of celite and washed with ethyl acetate. The filtrate was evaporated to dryness. The residue was purified by flash column chromatography to afford intermediate 43a (660 mg, >99%).

Step—2: Preparation of intermediate—44a

To a stirred solution of intermediate 43a (500 mg, 2.33 mmol) in DMF (5 mL) was added sodium hydride (60% in mineral oil, 280 mg, 6.99 mmol) at 0° C. The reaction mass was stirred for 30 min. To the reaction mass was added methyl iodide (450 μL, 6.99 mmol) at 0° C. The reaction mass was stirred at 23° C. for 2 h. The reaction mass was diluted with water and extracted with ethyl acetate. The organic layer was washed with water and brine, dried over anhydrous sodium sulfate and concentrated to dryness. The residue was purified by flash column chromatography to afford intermediate 44a (370 mg, 70%)

Step—3: Preparation of intermediate—45a

To a stirred solution of intermediate 44a (370 mg, 1.62 mmol) in 1,4-dioxane (5 mL) was added 4M HCl in 1,4-dioxane (5 mL) at 0° C. The reaction mass was stirred for 2 h at 23° C. The organics were evaporated off under reduced pressured. The residue was washed with dry ether and dried under vacuum to afford intermediate 45a (200 mg, >99%) as its HCl salt.

Intermediates (45b-45 g) were prepared in an analogous manner to intermediate 45a as described in Scheme 8 or were commercially available:

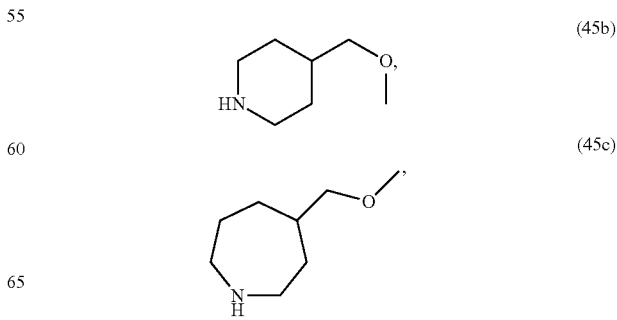

(45b)

(45c)

-continued

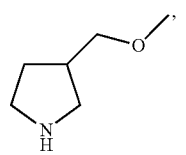
(45d)

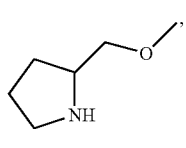
(45e)

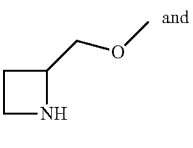 and
(45f)

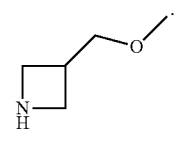
(45g)

Scheme 9: Preparation of Intermediate (47a)

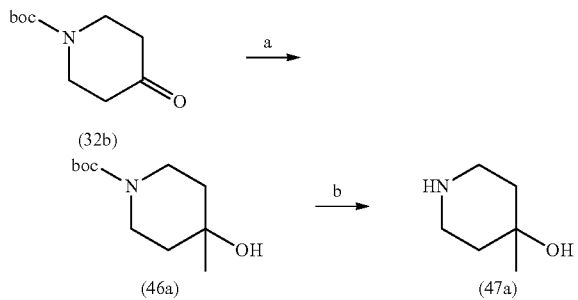

Reagents and Conditions: (a) MeMgBr, THF, -78° C.; and (b) 4M HCl in dioxane

Step—1: Preparation of intermediate—46a

To a stirred solution of intermediate 32b (500 mg, 2.70 mmol) in dry THF (15 mL) was added methyl magnesium bromide (3 M in diethyl ether, 0.90 mL, 2.70 mmol) at −78° C. The reaction mass was stirred at −78° C. for 4 h and then at 23° C. for 2 h. The reaction mass was quenched with saturated ammonium chloride solution and extracted with ethyl acetate. The organic layer was washed with brine, dried over anhydrous sodium sulfate and concentrated to dryness. The crude mass was purified by flash column chromatography to afford intermediate 46a (100 mg, 19%).

Step—2: Preparation of intermediate—47a

To a stirred solution of intermediate 46a (100 mg, 0.49 mmol) in 1,4-dioxane (5 mL) was added 4M HCl in 1,4-dioxane (5 mL) at 0° C. The reaction mass was stirred for 2 h at 23° C. The organics were evaporated off under reduced pressured. The residue was washed with dry ether and dried under vacuum to afford intermediate 47a (50 mg, >99%) as its HCl salt.

Intermediates (47b-47d) were prepared in an analogous manner to intermediate 47a as described in Scheme 9:

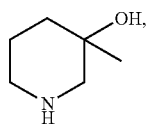
(47b)

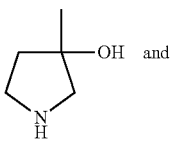 and
(47c)

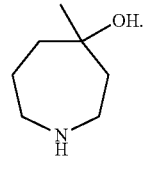
(47d)

3) Preparation of Compounds of the Invention

Unless specified otherwise, the reagents used in the preparation of compounds, including intermediates, of the present invention were purchased from Sigma-Aldrich Corporation (St. Louis, Mo., USA) and/or its subsidiaries, such as Fluka Chemie AG (Buchs, Switzerland) and Aldrich Chemical Company, Inc. (Milwaukee, Wis., USA).

Compounds of Invention Type Ia

Examples 1-203 of Table 1 were prepared via the process of Scheme 1, supra, using amide coupling such as CDI/TFA, CDI/TEA, PyBOP, HATU or EDC/HOBt:

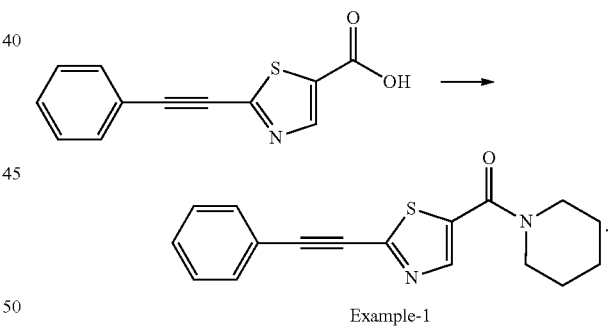

Example-1

Example 1

(2-Phenylethynyl-thiazol-5-yl)-piperidin-1-yl-methanone

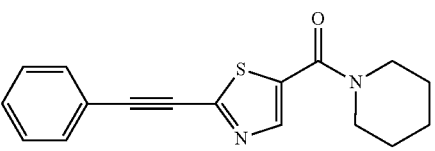 [SMILES: O=C(c1cnc(C#Cc2ccccc2)s1)N1CCCCC1]

Example 1 was prepared via the process of Scheme 1, step 3, Method—A, as follows:

N,N-Carbonyldiimidazole (790 mg, 4.87 mmol) (Fluka Chemie AG) was added to a solution of 2-phenylethynyl-thiazole-5-carboxylic acid (1.00 g, 4.36 mmol) [Intermediate 1] in tetrahydrofuran (17.4 mL) and stirred for 60 minutes. Piperidine (3.03 g, 35.6 mmol) and trifluoroacetic acid (295 µL, 3.83 mmol) were added and the mixture was stirred for 20 hours. The yellow solution was diluted with 150 mL of EtOAc and washed with 3.7 M HCl solution (5×30 mL), water (1×30 mL), 1.0 M $K_2CO_3$ (4×30 mL), water (2×30 mL), brine (1×30 mL), dried ($Na_2SO_4$) and concentrated to give a light tan solid (94% pure by LC/MS). The sample was further purified by silica gel chromatography over a 40 g $SiO_2$ column using a gradient elution from 25% EtOAc in hexanes to 30% EtOAc in hexanes over 30 minutes to give title compound (2-phenyl-ethynyl-thiazol-5-yl)-piperidin-1-yl-methanone (797 mg, 62%) as a light yellow powder. $^1$H NMR (300 MHz, $CDCl_3$) δ 7.94 (s, 1H), 7.63-7.59 (m, 2H), 7.46-7.36 (m, 3H), 3.69-3.67 (m, 4H), 1.78-1.62 (m, 6H). LCMS (Method 1), RT=1.41. Calculated $[M+H]^+$=297; Observed $[M+H]^+$=297.

Examples 2-74 were prepared in a similar fashion as Example 1, but with the appropriate intermediate.

Example 75

1-(2-Phenylethynyl-thiazole-5-carbonyl)-piperidin-4-one

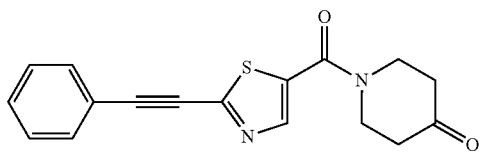 [SMILES: O=C1CCN(C(=O)c2cnc(C#Cc3ccccc3)s2)CC1]

Example 75 was prepared via the process of Scheme 1, step 3, Method—B, supra, as follows: 2-Phenylethynyl-thiazole-5-carboxylic acid (0.100 g, 0.436 mmol) in tetrahydrofuran (1.7 mL) [Intermediate 1] was stirred, and N,N'-carbonyldiimidazole (0.079 g, 0.49 mmol) (Fluka Chemie AG) was added in one portion at room temperature. The mixture was stirred for 60 minutes and then 4-piperidone monohydrochloride (0.241 g, 1.78 mmol) (3B Pharmachem (Wuhan) International Co., LTD (Libertyville, Ill., USA)) was added, followed by the addition of triethylamine (192 uL, 1.38 mmol). The mixture was stirred for about 2 hours and was worked up by diluting with 25 mL of EtOAc and washing with 2×10 mL of 1.7% aq. HCl, 1×10 mL of water, 3×10 mL of 1.0 M $K_2CO_3$, and 1×10 mL of brine; dried ($Na_2SO_4$), and concentrated to give the title compound, 1-(2-phenylethynyl-thiazole-5-carbonyl)-piperidin-4-one (55 mg; 41%), as an off-white solid. $^1$H NMR (300 MHz, $CDCl_3$) δ 8.04 (s, 1H), 7.63-7.59 (m, 2H), 7.47-7.32 (m, 3H), 4.03 (t, J=6.3 Hz, 4H), 2.59 (t, J=6.3 Hz, 4H). LC/MS (Method 1), RT=1.05 min. Calculated $[M+H]^+$=311; Observed $[M+H]^+$=311.

Examples 76-81 were prepared in a similar fashion as Example 75, but with the appropriate intermediate.

Example 82

(4,4-Difluoro-piperidin-1-yl)-(2-phenylethynyl-thiazol-5-yl)-methanone

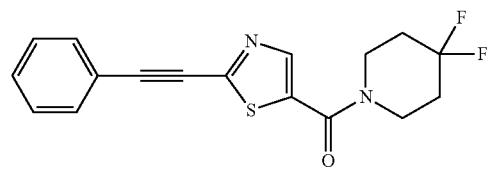 [SMILES: O=C(c1cnc(C#Cc2ccccc2)s1)N1CCC(F)(F)CC1]

Example 82 was prepared via the process of Scheme 1, step 3, Method—C, supra, as follows:

In a small culture tube, 2-phenylethynyl-thiazole-5-carboxylic acid (28 mg, 0.12 mmol) [Intermediate 1], 4,4-difluoropiperidine hydrochloride (23 mg, 0.14 mmol) (Oakwood Products, Inc. (West Columbia, S.C., USA) and dichloromethane (1.5 mL) were added. To the mixture, PyBOP® (76 mg, 0.14 mmol) was added, followed by N,N-diisopropylethylamine (63 µL, 0.36 mmol), and the reaction was stirred at room temperature for about 17 hours. Afterwards, the crude reaction mixture was directly purified by Preparative TLC, eluting with 40% EtOAc in hexanes to give 37 mg (92%) of the titled compound, (4,4-difluoro-piperidin-1-yl)-(2-phenylethynyl-thiazol-5-yl)-methanone, as a white solid. $^1$H NMR (300 MHz, $CDCl_3$) δ 7.99 (s, 1H), 7.66-7.59 (m, 2H), 7.49-7.37 (m, 3H), 3.92-3.82 (m, 4H), 2.18-2.01 (m, 4H). LC/MS (Method 3), RT=1.43 min. Calculated $[M+H]^+$=333; Observed $[M+H]^+$=333.

Examples 83-85 were prepared in a similar fashion as Example 82 but with the appropriate intermediate.

Example 86

2-Phenylethynyl-thiazole-4-carboxylic acid cyclopropylamide

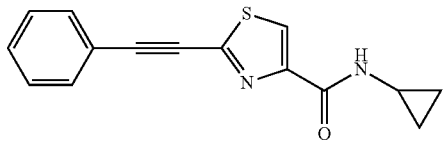 [SMILES: O=C(NC1CC1)c1csc(C#Cc2ccccc2)n1]

Example 86 was prepared via the process of Scheme 1, step 3, Method—D, as follows:

Cyclopropylamine (2.49 mg, 0.00436 mmol), 1-hydroxybenzotriazole (0.589 mg, 0.00436 mmol), triethylamine (1.82 µL, 0.0131 mmol), N-(3-dimethylaminopropyl-N'-ethylcarbodiimide hydrochloride (2.09 mg, 0.0109 mmol) and $CH_2Cl_2$ (2 mL) were combined, and then 2-phenylethynyl-thiazole-4-carboxylic acid (10 mg, 0.004 mmol) was added. The reaction was left standing for about 16 hours and then purified by preparative HPLC. LC/MS (Method 5), RT=1.33 min. Calculated $[M+H]^+$=269; Observed $[M+H]^+$=269.

Examples 87-111 were prepared in a similar fashion as Example 86, but with the appropriate intermediate.

Example 180

[2-(3,5-Difluoro-phenylethynyl)-thiazol-5-yl]-piperidin-1-yl-methanone

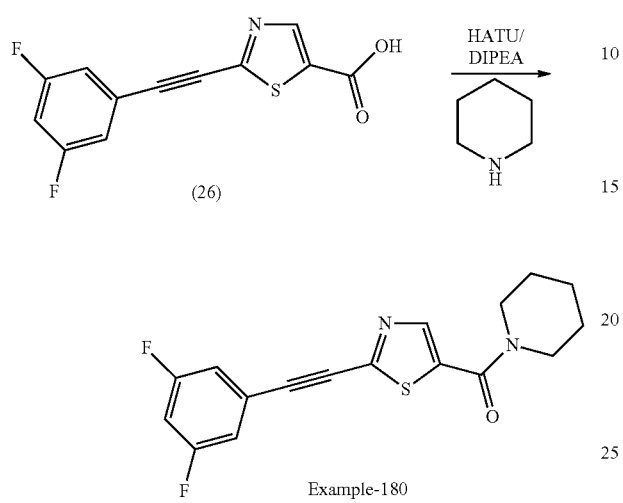

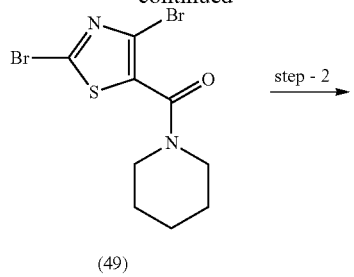

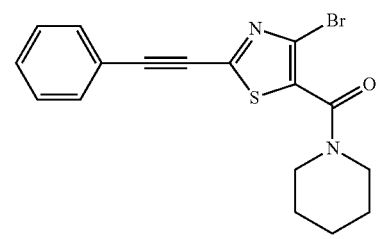

Example 180 was prepared via the process of Scheme 1, step 3, Method—E, as follows:

To a stirred solution of acid 26 (150 mg, 0.57 mmol) in DCM (10 mL) was added DIPEA (220 mg, 1.71 mmol) and HATU (260 mg, 0.68 mmol) at 0° C. The reaction mass was allowed to stir at the same temperature for 15 min. To the reaction was added piperidine (53 mg, 0.62 mmol) and the reaction mass was allowed to stir at 23° C. for 16 h. The reaction mass was diluted with DCM, washed with saturated sodium bicarbonate solution, saturated ammonium chloride solution and brine. The organic phase was dried over anhydrous sodium sulfate and concentrated to dryness. The crude residue was purified by flash column chromatography to afford the titled compound, [2-(3,5-Difluoro-phenylethynyl)-thiazol-5-yl]-piperidin-1-yl-methanone 180 (45 mg, 24%).

Examples 112-177 were prepared in a similar fashion as Example 180, but with the appropriate intermediate.

Example 178

(4-Bromo-2-phenylethynyl-thiazol-5-yl)-piperidin-1-yl-methanone

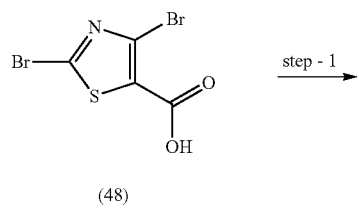

Example 178 was prepared via the process of Scheme 4, steps a and b, as follows:

Step—1: Preparation of intermediate—49

To a stirred solution of 2,4-dibromo-5-thiazole carboxylic acid (48, 400 mg, 1 mmol), O-(benzotriazol-1-yl)-N,N,N',N'-tetramethyluronium hexafluorophosphate (790 mg, 2.1 mmol) and piperidine (180 uL, 1.8 mmol) in methylene chloride (5.0 mL, 78 mmol) was added triethylamine (580 μL, 4.2 mmol) at room temperature. The resulting turbid mixture was allowed to stir at rt overnight and quenched with water. The product was extracted using dichloromethane and washed with water, citric acid solution, water and brine. Removal of solvent gave the intermediate (49) (2,4-Dibromo-thiazol-5-yl)-piperidin-1-yl-methanone (300 mg, 30%) which was used as such for the next step.

Step—2: Preparation of compound of invention (Example 178)

To a stirred solution of a mixture of intermediate 49 (2,4-Dibromo-thiazol-5-yl)-piperidin-1-yl-methanone (325 mg, 0.918 mmol), bis(triphenylphosphine)palladium(II) chloride (12.9 mg, 0.0184 mmol), copper(I) iodide (8.74 mg, 0.0459 mmol) and phenylacetylene (0.101 mL, 0.918 mmol) was added triethylamine (3.0 mL, 22 mmol) and the reaction was heated at 90° C. for 30 minutes in a microwave (150 watts). The solvent triethylamine was removed and the crude product was extracted with dichloromethane and washed the organic portion with aqueous citric acid solution, water and brine. Purification of the crude product afford the titled compound (4-Bromo-2-phenylethynyl-thiazol-5-yl)-piperidin-1-yl-methanone (60 mg, 20%) as a pale brown color solid Example—189

[2-(3-Methoxy-phenylethynyl)-thiazol-5-yl]-piperidin-1-yl-methanone

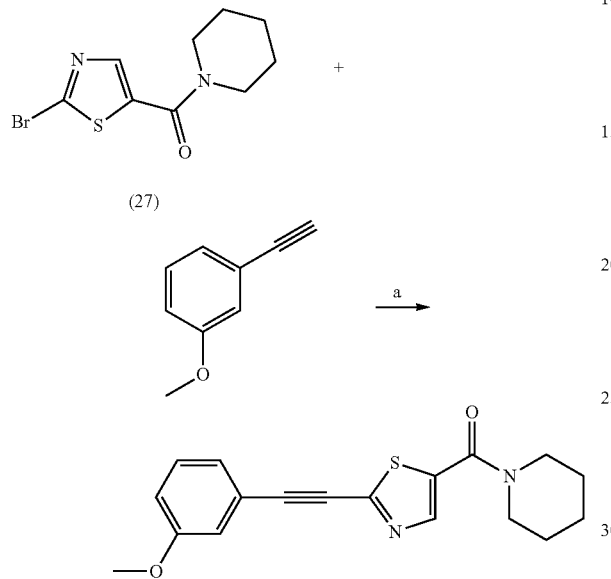

Example-189

Reagents and Conditions: (a) PdCl$_2$(PPh$_3$)$_2$, Et$_3$N or Et$_3$NH, Microwave, 140° C. or 70° C.

Example 189 was prepared via the process of Scheme 2, step 3, as follows:

To a deoxygenated solution of bromothiazole intermediate 27 (1 mmol) and 3-methoxyphenylacetylene (1.1 mmol) in triethylamine (1 mL) and DMF (1 mL) was added copper (I) iodide (5 mol %) and PdCl$_2$(PPh$_3$)$_2$ (10 mol %) under argon atmosphere. The reaction mass was heated at 100° C. for 20 min in a Biotage microwave reactor. The reaction mass was filtered through a bed of celite. The filtrate was evaporated to dryness and the residue was purified by flash column chromatography to afford the compounds invention 189.

Examples 179, 184-204 were prepared in a similar fashion as Example 189, but with the appropriate intermediate.

Example—183

[2-(3-Hydroxy-phenylethynyl)-thiazol-5-yl]-piperidin-1-yl-methanone

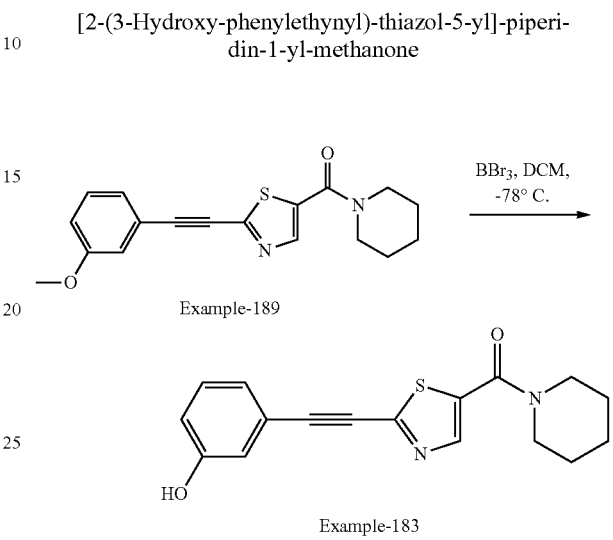

Example 183 was prepared from Example 189 followed by deprotection of the methoxy group, as follows:

To a solution of Example 189 (290 mg, 1 mmol) in dichloromethane (10 mL) was added boron tribromide (2 mmol). The reaction mass was stirred at 23° C. for 3 h. The reaction mass was diluted with DCM, washed with saturated sodium bicarbonate solution, saturated ammonium chloride solution and brine. The organic phase was dried over anhydrous sodium sulfate and concentrated to dryness. The crude residue was purified by flash column chromatography to afford the titled compound (Example 183, 130 mg, 47%).

Example 181 and Example 182 were prepared in an analogous manner as Example 183, but from Example 204 and Example 192, respectively.

TABLE 1

| Example | Compound | Compound Name | Characterization |
|---|---|---|---|
| 1 | | (2-Phenylethynyl-thiazol-5-yl)-piperidin-1-yl-methanone | $^1$H NMR (300 MHz, CDCl$_3$) δ 7.94 (s, 1H), 7.63-7.59 (m, 2H), 7.46-7.36 (m, 3H), 3.69-3.67 (m, 4H), 1.78-1.62 (m, 6H). LCMS (Method 1), RT = 1.41 min. Calculated [M + H]$^+$ = 297; Observed [M + H]$^+$ = 297. Yield 62% |
| 2 | | (4-Fluoro-piperidin-1-yl)-(2-phenylethynyl-thiazol-5-yl)-methanone | $^1$H NMR (400 MHz, CDCl$_3$) δ 7.95 (s, 1H), 7.63-7.57 (m, 2H), 7.46-7.34 (m, 3H), 4.95 (doublet of septet, J = 50.0 Hz, 4.0 Hz, 1H), 4.10-3.79 (br m, 2H), 3.78-3.55 (br m, 2H), 2.09-1.70 (m, 5H). LCMS (Method 1), RT = 1.28 min. Calculated [M + H]$^+$ = 315; Observed [M + H]$^+$ = 315. |

TABLE 1-continued

| Example | Compound | Compound Name | Characterization |
|---|---|---|---|
| 3 | | (3-Fluoro-piperidin-1-yl)-(2-phenylethynyl-thiazol-5-yl)-methanone | $^1$H NMR (400 MHz, CDCl$_3$) δ 7.95 (s, 1H), 7.58-7.52 (m, 2H), 7.43-7.30 (m, 3H), 5.62-5.35 (br m, 1H), 4.74 (br d, J = 49.0 Hz, 1H), 4.22-4.07 (br m, 1H), 3.29-3.04 (m, 2H), 1.65-1.54 (m, 2H), 1.26-1.12 (m, 2H). LCMS (Method 1), RT = 1.28 min. Calculated [M + H]$^+$ = 315; Observed [M + H]$^+$ = 315. |
| 4 | | (2-Phenylethynyl-thiazol-5-yl)-pyrrolidin-1-yl-methanone | $^1$H NMR (400 MHz, CDCl$_3$) δ 8.18 (s, 1H), 7.64-7.58 (m, 2H), 7.47-7.36 (m, 3H), 3.76 (t, J = 6.9 Hz, 2H), 3.67 (t, J = 7.0 Hz, 2H), 2.06 (quintet, J = 6.9 Hz, 2H), 1.98 (quintet, J = 6.9 Hz, 2H). LCMS (Method 1), RT = 1.23 min. Calculated [M + H]$^+$ = 283; Observed [M + H]$^+$ = 283. |
| 5 | | ((S)-3-Fluoro-pyrrolidin-1-yl)-(2-phenylethynyl-thiazol-5-yl)-methanone | $^1$H NMR (300 MHz, CDCl$_3$) δ 8.20 (s, 1H), 7.67-7.57 (m, 2H), 7.50-7.35 (m, 3H) 5.35 (br d, J = 52 Hz, 1H), 4.17-3.69 (br m, 4H), 2.55-1.89 (br m, 2H). LCMS (Method 1), RT = 1.18 min. Calculated [M + H]$^+$ = 301; Observed [M + H]$^+$ = 301. |
| 6 | | ((R)-3-Fluoro-pyrrolidin-1-yl)-(2-phenylethynyl-thiazol-5-yl)-methanone | $^1$H NMR (300 MHz, CDCl$_3$) δ 8.18 (s, 1H), 7.65-7.52 (m, 2H), 7.45-7.32 (m, 3H), 5.34 (br d, J = 52 Hz, 1H), 4.15-3.66 (br m, 4H), 2.53-1.91 (br m, 2H). LCMS (Method 1), RT = 1.18 min. Calculated [M + H]$^+$ = 301; Observed [M + H]$^+$ = 301. |
| 7 | | Morpholin-4-yl-(2-phenylethynyl-thiazol-5-yl)-methanone | $^1$H NMR (400 MHz, CDCl$_3$) δ 7.96 (s, 1H), 7.63-7.56 (m, 2H), 7.49-7.37 (m, 3H), 3.69 (t, J = 4.6 Hz, 4H), 2.49 (t, J = 4.6 Hz, 4H). LCMS (Method 2), RT = 0.70 min. Calculated [M + H]$^+$ = 298; Observed [M + H]$^+$ = 298.9. |
| 8 | | (3-Hydroxy-piperidin-1-yl)-(2-phenylethynyl-thiazol-5-yl)-methanone | $^1$H NMR (400 MHz, CDCl$_3$) δ 8.04 (s, 1H), 7.64-7.57 (m, 2H), 7.49-7.35 (m, 3H), 3.98-3.89 (br m, 1H), 3.87-3.80 (br s, 1H), 3.72-3.54 (br m, 4H), 2.02-1.87 (m, 2H), 1.78-1.65 (m, 1H), 1.65-1.53 (br m, 1H). LCMS (Method 2), RT = 0.70 min. Calculated [M + H]$^+$ = 313; Observed [M + H]$^+$ = 313. |
| 9 | | (4-Hydroxymethyl-piperidin-1-yl)-(2-phenylethynyl-thiazol-5-yl)-methanone | $^1$H NMR (400 MHz, CDCl$_3$) δ 7.95 (s, 1H), 7.64-7.58 (m, 2H), 7.50-7.36 (m, 3H), 3.56 (d, J = 6.0 Hz, 2H), 3.28-3.12 (m, 2H), 3.10-2.74 (br m, 2H), 1.94-1.77 (m, 2H), 1.39-1.08 (br m, 3H). LCMS (Method 2), RT = 0.71 min. Calculated [M + H]$^+$ = 327; Observed [M + H]$^+$ = 327. |
| 10 | | (2,6-Dimethyl-morpholin-4-yl)-(2-phenylethynyl-thiazol-5-yl)-methanone | $^1$H NMR (400 MHz, CDCl$_3$) δ 7.95 (s, 1H), 7.64-7.58 (m, 2H), 7.50-7.36 (m, 3H), 4.6-3.92 (m, 2H), 3.64 (t, J = 6.0 Hz, 2H), 3.11-2.48 (br m, 2H), 1.22 (d, J = 6.0 Hz, 6H). LCMS (Method 2), RT = 1.03 min. Calculated [M + H]$^+$ = 327; Observed [M + H]$^+$ = 327. |
| 11 | | (4-Methyl-piperidin-1-yl)-(2-phenylethynyl-thiazol-5-yl)-methanone | $^1$H NMR (CDCl$_3$) δ 7.93 (s, 1H), 7.62-7.56 (m, 2H), 7.45-7.34 (m, 3H), 4.39 (br s, 2H), 2.98 (br s, 2H), 1.77-1.63 (m, 2H), 1.27-1.14 (m, 3H), 0.99 (d, J = 6.3 Hz, 3H). LCMS (Method 1), RT = 1.50 min. Calculated [M + H]$^+$ = 311; Observed [M + H]$^+$ = 311. |

TABLE 1-continued

| Example | Compound | Compound Name | Characterization |
|---|---|---|---|
| 12 | 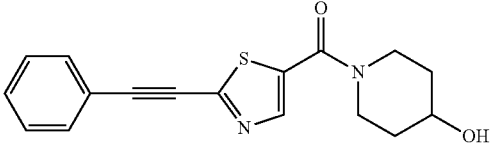 [SMILES: O=C(c1cnc(C#Cc2ccccc2)s1)N1CCC(O)CC1] | (4-Hydroxy-piperidin-1-yl)-(2-phenylethynyl-thiazol-5-yl)-methanone | ¹H NMR (CDCl₃) δ 7.95 (s, 1H), 7.62-7.58 (m, 2H), 7.48-7.35 (m, 3H), 4.10-4.01 (m, 3H), 3.53-3.45 (m, 2H), 2.04-1.93 (m, 2H), 1.80 (br s, 1H), 1.69-1.58 (m, 2H). LCMS (Method 1), RT = 0.94 min. Calculated [M + H]⁺ = 313; Observed [M + H]⁺ = 313. |
| 13 | 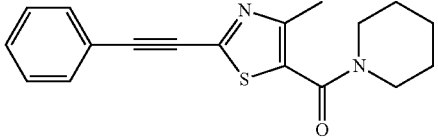 [SMILES: Cc1nc(C#Cc2ccccc2)sc1C(=O)N1CCCCC1] | (4-Methyl-2-phenylethynyl-thiazol-5-yl)-piperidin-1-yl-methanone | ¹H NMR (CDCl₃) δ 7.63-7.59 (m, 2H), 7.44-7.36 (m, 3H), 3.58 (br s, 4H), 2.49 (s, 3H), 1.75-1.64 (m, 6H). LCMS (Method 1), RT = 1.45 min. Calculated [M + H]⁺ = 311; Observed [M + H]⁺ = 311. |
| 14 | 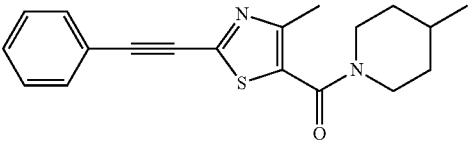 [SMILES: Cc1nc(C#Cc2ccccc2)sc1C(=O)N1CCC(C)CC1] | (4-Methyl-2-phenylethynyl-thiazol-5-yl)-(4-methyl-piperidin-1-yl)-methanone | ¹H NMR (CDCl₃) δ 7.63-7.59 (m, 2H), 7.44-7.36 (m, 3H), 4.20 (br s, 2H), 2.96 (br s, 2H), 2.49 (s, 3H), 1.77-1.64 (m, 4H), 1.30-1.14 (m, 3H), 0.88 (d, J = 6.3 Hz, 3H). LCMS (Method 1), RT = 1.59 min. Calculated [M + H]⁺ = 325; Observed [M + H]⁺ = 325. |
| 15 | 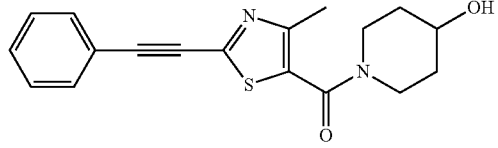 [SMILES: Cc1nc(C#Cc2ccccc2)sc1C(=O)N1CCC(O)CC1] | (4-Hydroxy-piperidin-1-yl)-(4-methyl-2-phenylethynyl-thiazol-5-yl)-methanone | ¹H NMR (300 MHz, CDCl₃) δ 7.62-7.58 (m, 2H), 7.47-7.38 (m, 3H), 4.05 (pentet, J = 3.8 Hz, 1H), 3.95 (br s, 2H), 3.41 (m, 2H), 2.50 (s, 3H), 2.00-1.57 (m, 4H). LCMS (Method 1), RT = 0.96 min. Calculated [M + H]⁺ = 327; Observed [M + H]⁺ = 327. |
| 16 | 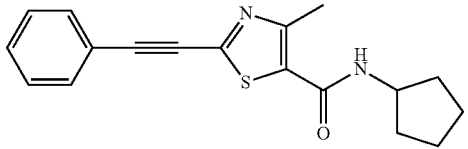 [SMILES: Cc1nc(C#Cc2ccccc2)sc1C(=O)NC1CCCC1] | 4-Methyl-2-phenylethynyl-thiazole-5-carboxylic acid cyclopentylamide | ¹H NMR (300 MHz, CDCl₃) δ 7.63-7.59 (m, 2H), 7.47-7.37 (m, 3H), 5.71 (d, J = 5.9 Hz, 1H), 4.43-4.32 (m, 1H), 2.72 (s, 3H), 2.15-2.06 (m, 2H), 1.78-1.46 (m, 6H). LCMS (Method 1), RT = 1.50 min. Calculated [M + H]⁺ = 311; Observed [M + H]⁺ = 311. |
| 17 | 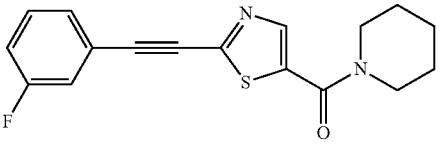 [SMILES: O=C(c1cnc(C#Cc2cccc(F)c2)s1)N1CCCCC1] | [2-(3-Fluoro-phenylethynyl)-thiazol-5-yl]-piperidin-1-yl-methanone | ¹H NMR (400 MHz, CDCl₃) δ 7.95 (s, 1H), 7.42-7.28 (m, 3H), 7.18-7.10 (m, 1H), 3.73-3.62 (m, 4H), 1.78-1.61 (m, 6H). LCMS (Method 3), RT = 1.46 min. Calculated [M + H]⁺ = 315; Observed [M + H]⁺ = 315. |
| 18 | 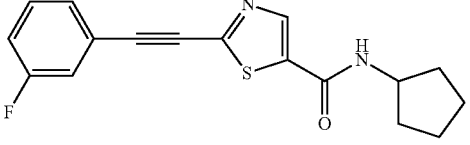 | 2-(3-Fluoro-phenylethynyl)-thiazole-5-carboxylic acid cyclopentylamide | ¹H NMR (400 MHz, CDCl₃) δ 8.12 (s, 1H), 7.42-7.28 (m, 3H), 7.18-7.11 (m, 1H), 5.98 (d, J = 7.1 Hz, 1H), 4.43-4.33 (m, 1H), 2.17-2.06 (m, 2H), 1.81-1.46 (m, 6H). LCMS (Method 3), RT = 1.49 min. Calculated [M + H]⁺ = 315; Observed [M + H]⁺ = 315. |
| 19 | 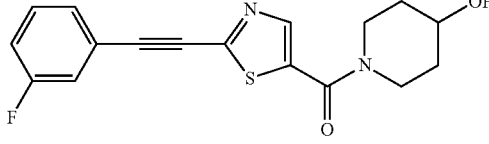 | [2-(3-Fluoro-phenylethynyl)-thiazol-5-yl]-(4-hydroxy-piperidin-1-yl)-methanone | ¹H NMR (400 MHz, CDCl₃) δ 7.97 (s, 1H), 7.42-7.28 (m, 3H), 7.18-7.11 (m, 1H), 4.11-3.96 (m, 3H), 3.55-3.46 (m, 2H), 2.05-1.75 (m, 3H), 1.72-1.57 (m, 2H). LCMS (Method 3), RT = 1.11 min. Calculated [M + H]⁺ = 331; Observed [M + H]⁺ = 331. |
| 20 | 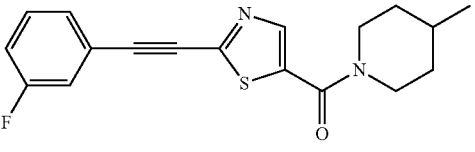 [SMILES: CC1CCN(C(=O)c2cnc(C#Cc3cccc(F)c3)s2)CC1] | 2-(3-Fluoro-phenylethynyl)-thiazol-5-yl]-(4-methyl-piperidin-1-yl)-methanone | ¹H NMR (400 MHz, CDCl₃) δ 7.94 (s, 1H), 7.44-7.28 (m, 3H), 7.18-7.11 (m, 1H), 4.82-3.78 (br s, 2H), 3.37-2.60 (br s, 2H), 1.82-1.62 (m, 3H), 1.31-1.13 (m, 2H), 1.00 (d, J = 6.6 Hz, 3H). LCMS (Method 3), RT = 1.57 min. Calculated [M + H]⁺ = 329; Observed [M + H]⁺ = 329. |

TABLE 1-continued

| Example | Compound Name | Characterization |
|---|---|---|
| 21 | [2-(3-Fluoro-phenylethynyl)-thiazol-5-yl]-pyrrolidin-1-yl-methanone | ¹H NMR (400 MHz, CDCl₃) δ 8.18 (s, 1H), 7.43-7.28 (m, 3H), 7.18-7.11 (m, 1H), 3.81-3.63 (m, 4H), 2.14-1.87 (m, 4H). LCMS (Method 3), RT = 1.35 min. Calculated [M + H]⁺ = 301; Observed [M + H]⁺ = 301. |
| 22 | [2-(3-Fluoro-phenylethynyl)-thiazol-5-yl]-morpholin-4-yl-methanone | ¹H NMR (400 MHz, CDCl₃) δ 7.98 (s, 1H), 7.42-7.28 (m, 3H), 7.18-7.12 (m, 1H), 3.76 (m, 8H). LCMS (Method 3), RT = 1.23 min. Calculated [M + H]⁺ = 317; Observed [M + H]⁺ = 317. |
| 23 | Piperidin-1-yl-(2-m-tolylethynyl-thiazol-5-yl)-methanone | ¹H NMR (400 MHz, CDCl₃) δ 7.94 (s, 1H), 7.45-7.39 (m, 2H), 7.31-7.22 (m, 2H), 3.73-3.63 (m, 4H), 2.38 (s, 3H), 1.78-1.59 (m, 6H). LCMS (Method 3), RT = 1.54 min. Calculated [M + H]⁺ = 311; Observed [M + H]⁺ = 311. |
| 24 | 2-m-Tolylethynyl-thiazole-5-carboxylic acid cyclopentylamide | ¹H NMR (400 MHz, CDCl₃) δ 8.11 (s, 1H), 7.44-7.38 (m, 2H), 7.31-7.22 (m, 2H), 6.07 (d, J = 7.1 Hz, 1H), 4.43-4.32 (m, 1H), 2.37 (s, 3H), 2.16-2.04 (m, 2H), 1.81-1.45 (m, 6H). LCMS (Method 3), RT = 1.56 min. Calculated [M + H]⁺ = 311; Observed [M + H]⁺ = 311. |
| 25 | (4-Hydroxy-piperidin-1-yl)-(2-m-tolylethynyl-thiazol-5-yl)-methanone | ¹H NMR (400 MHz, CDCl₃) δ 7.94 (s, 1H), 7.45-7.39 (m, 2H), 7.31-7.21 (m, 2H), 4.11-3.97 (m, 3H), 3.55-3.44 (m, 2H), 2.37 (s, 3H), 2.04-1.75 (m, 3H), 1.71-1.56 (m, 2H). LCMS (Method 3), RT = 1.19 min. Calculated [M + H]⁺ = 327; Observed [M + H]⁺ = 327. |
| 26 | Morpholin-4-yl-(2-m-tolylethynyl-thiazol-5-yl)-methanone | ¹H NMR (400 MHz, CDCl₃) δ 7.96 (s, 1H), 7.45-7.39 (m, 2H), 7.31-7.22 (m, 2H), 3.76 (m, 8H), 2.37 (s, 3H). LCMS (Method 3), RT = 1.32 min. Calculated [M + H]⁺ = 313; Observed [M + H]⁺ = 313. |
| 27 | Pyrrolidin-1-yl-(2-m-tolylethynyl-thiazol-5-yl)-methanone | ¹H NMR (400 MHz, CDCl₃) δ 8.16 (s, 1H), 7.46-7.38 (m, 2H), 7.32-7.21 (m, 2H), 3.81-3.63 (m, 4H), 2.37 (s, 3H), 2.14-1.87 (m, 4H). LCMS (Method 3), RT = 1.43 min. Calculated [M + H]⁺ = 297; Observed [M + H]⁺ = 297. |
| 28 | (4-Methyl-piperidin-1-yl)-(2-m-tolylethynyl-thiazol-5-yl)-methanone | ¹H NMR (400 MHz, CDCl₃) δ 7.93 (s, 1H), 7.45-7.39 (m, 2H), 7.31-7.22 (m, 2H), 4.85-3.81 (br s, 2H), 3.37-2.60 (br s, 2H), 2.37 (s, 3H), 1.82-1.62 (m, 3H), 1.31-1.14 (m, 2H), 1.01 (d, J = 6.6 Hz, 3H). LCMS (Method 3), RT = 1.64 min. Calculated [M + H]⁺ = 325; Observed [M + H]⁺ = 325. |
| 29 | [2-(4-Fluoro-phenylethynyl)-thiazol-5-yl]-(4-hydroxy-piperidin-1-yl)-methanone | ¹H NMR (400 MHz, CDCl₃) δ 7.95 (s, 1H), 7.65-7.56 (m, 2H), 7.15-7.05 (m, 2H), 4.14-3.92 (m, 3H), 3.56-3.43 (m, 2H), 2.21-1.84 (m, 3H), 1.72-1.56 (m, 2H). LCMS (Method 3), RT = 1.11 min. Calculated [M + H]⁺ = 331; Observed [M + H]⁺ = 331. |

TABLE 1-continued

| Example | Compound | Compound Name | Characterization |
|---|---|---|---|
| 30 | | [2-(4-Fluoro-phenylethynyl)-thiazol-5-yl]-piperidin-1-yl-methanone | $^1$H NMR (400 MHz, CDCl$_3$) δ 7.94 (s, 1H), 7.65-7.56 (m, 2H), 7.15-7.05 (m, 2H), 3.76-3.60 (m, 4H), 1.79-1.58 (m, 6H). LCMS (Method 3), RT = 1.46 min. Calculated [M + H]$^+$ = 315; Observed [M + H]$^+$ = 315. |
| 31 | | 2-(4-Fluoro-phenylethynyl)-thiazole-5-carboxylic acid cyclopentylamide | $^1$H NMR (400 MHz, CDCl$_3$) δ 8.10 (s, 1H), 7.64-7.58 (m, 2H), 7.14-7.07 (m, 2H), 5.90 (d, J = 7.1 Hz, 1H), 4.44-4.33 (m, 1H), 2.18-2.06 (m, 2H), 1.82-1.46 (m, 6H). LCMS (Method 3), RT = 1.44 min. Calculated [M + H]$^+$ = 315; Observed [M + H]$^+$ = 315. |
| 32 | | [2-(4-Fluoro-phenylethynyl)-thiazol-5-yl]-morpholin-4-yl-methanone | $^1$H NMR (400 MHz, CDCl$_3$) δ 7.96 (s, 1H), 7.63-7.57 (m, 2H), 7.13-7.06 (m, 2H), 3.76 (s, 8H). LCMS (Method 3), RT = 1.21 min. Calculated [M + H]$^+$ = 317; Observed [M + H]$^+$ = 317. |
| 33 | | [2-(3-Fluoro-phenylethynyl)-thiazol-5-yl]-pyrrolidin-1-yl-methanone | $^1$H NMR (400 MHz, CDCl$_3$) δ 8.17 (s, 1H), 7.64-7.58 (m, 2H), 7.14-7.05 (m, 2H), 3.81-3.65 (m, 4H), 2.12-1.93 (m, 4H). LCMS (Method 3), RT = 1.33 min. Calculated [M + H]$^+$ = 301; Observed [M + H]$^+$ = 301. |
| 34 | | [2-(4-Fluoro-phenylethynyl)-thiazol-5-yl]-(4-methyl-piperidin-1-yl)-methanone | $^1$H NMR (300 MHz, CDCl$_3$) δ 7.93 (s, 1H), 7.63-7.55 (m, 2H), 7.13-7.06 (m, 2H), 4.83-3.78 (br s, 2H), 3.33-2.53 (br s, 2H), 1.82-1.60 (m, 3H), 1.31-1.12 (m, 2H), 1.00 (d, J = 6.3 Hz, 3H). LCMS (Method 3), RT = 1.55 min. Calculated [M + H]$^+$ = 329; Observed [M + H]$^+$ = 329. |
| 35 | | [2-(3-Chloro-phenylethynyl)-thiazol-5-yl]-piperidin-1-yl-methanone | $^1$H NMR (300 MHz, CDCl$_3$) δ 7.95 (s, 1H), 7.62-7.58 (m, 1H), 7.52-7.46 (m, 1H), 7.44-7.38 (m, 1H), 7.37-7.30 (m, 1H), 3.76-3.59 (m, 4H), 1.80-1.57 (m, 6H). LCMS (Method 3), RT = 1.56 min. Calculated [M + H]$^+$ = 331; Observed [M + H]$^+$ = 331. |
| 36 | | [2-(3-Chloro-phenylethynyl)-thiazol-5-yl]-morpholin-4-yl-methanone | $^1$H NMR (300 MHz, CDCl$_3$) δ 7.98 (s, 1H), 7.62-7.58 (m, 1H), 7.53-7.47 (m, 1H), 7.45-7.39 (m, 1H), 7.38-7.31 (m, 1H), 3.77 (s, 8H). LCMS (Method 3), RT = 1.31 min. Calculated [M + H]$^+$ = 333; Observed [M + H]$^+$ = 333. |
| 37 | | 2-(3-Chloro-phenylethynyl)-thiazole-5-carboxylic acid cyclopentylamide | $^1$H NMR (300 MHz, CDCl$_3$) δ 8.12 (s, 1H), 7.63-7.58 (m, 1H), 7.53-7.46 (m, 1H), 7.45-7.39 (m, 1H), 7.38-7.31 (m, 1H), 5.97 (d, J = 7.2 Hz, 1H), 4.45-4.32 (m, 1H), 2.20-2.03 (m, 2H), 1.83-1.45 (m, 6H). LCMS (Method 3), RT = 1.58 min. Calculated [M + H]$^+$ = 331; Observed [M + H]$^+$ = 331. |
| 38 | | [2-(3-Chloro-phenylethynyl)-thiazol-5-yl]-(4-hydroxy-piperidin-1-yl)-methanone | $^1$H NMR (300 MHz, CDCl$_3$) δ 7.97 (s, 1H), 7.62-7.58 (m, 1H), 7.52-7.47 (m, 1H), 7.44-7.38 (m, 1H), 7.37-7.30 (m, 1H), 4.13-3.95 (m, 3H), 3.58-3.44 (m, 2H), 2.05-1.90 (m, 2H), 1.84-1.57 (m, 3H). LCMS (Method 3), RT = 1.20 min. Calculated [M + H]$^+$ = 347; Observed [M + H]$^+$ = 347. |

TABLE 1-continued

| Example | Compound | Compound Name | Characterization |
|---|---|---|---|
| 39 | 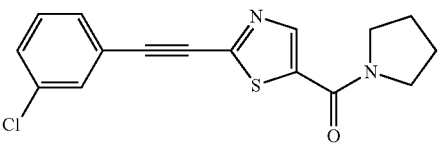 [SMILES: O=C(c1cnc(C#Cc2cccc(Cl)c2)s1)N1CCCC1] | [2-(3-Chloro-phenylethynyl)-thiazol-5-yl]-pyrrolidin-1-yl-methanone | $^1$H NMR (400 MHz, CDCl$_3$) δ 8.17 (s, 1H), 7.64-7.58 (m, 2H), 7.14-7.05 (m, 2H), 3.81-3.65 (m, 4H), 2.12-1.93 (m, 4H). LCMS (Method 3), RT = 1.33 min. Calculated [M + H]$^+$ = 301; Observed [M + H]$^+$ = 301. |
| 40 | 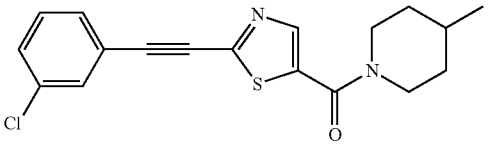 [SMILES: CC1CCN(C(=O)c2cnc(C#Cc3cccc(Cl)c3)s2)CC1] | [2-(4-Fluoro-phenylethynyl)-thiazol-5-yl]-(4-methyl-piperidin-1-yl)-methanone | $^1$H NMR (300 MHz, CDCl$_3$) δ 7.95 (s, 1H), 7.62-7.58 (m, 1H), 7.53-7.46 (m, 1H), 7.45-7.38 (m, 1H), 7.37-7.30 (m, 1H), 4.85-3.82 (br s, 2H), 3.29-2.65 (br s, 2H), 1.84-1.60 (m, 3H), 1.34-1.10 (m, 2H), 1.01 (d, J = 6.3 Hz, 3H). LCMS (Method 3), RT = 1.63 min. Calculated [M + H]$^+$ = 345; Observed [M + H]$^+$ = 345. |
| 41 | 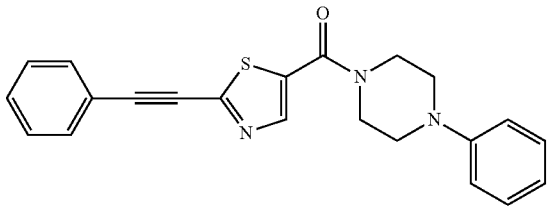 [SMILES: O=C(c1cnc(C#Cc2ccccc2)s1)N1CCN(c2ccccc2)CC1] | (2-Phenylethynyl-thiazol-5-yl)-(4-phenyl-piperazin-1-yl)-methanone | $^1$H NMR (300 MHz, CDCl$_3$) δ 7.93 (s, 1H), 7.57-7.53 (m, 2H), 7.40-7.29 (m, 3H), 7.27-7.20 (m, 2H), 6.90-6.84 (m, 3H), 3.46 (t, J = 5.1 Hz, 4H), 3.19 (t, J = 5.1 Hz, 4H). LCMS (Method 1), RT = 1.58 min. Calculated [M + H]$^+$ = 374; Observed [M + H]$^+$ = 374. |
| 42 | 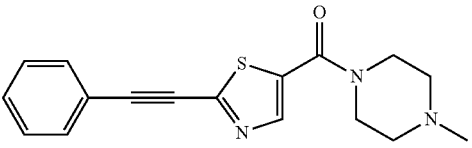 [SMILES: CN1CCN(C(=O)c2cnc(C#Cc3ccccc3)s2)CC1] | (4-Methyl-piperazin-1-yl)-(2-phenylethynyl-thiazol-5-yl)-methanone | $^1$H NMR (300 MHz, CDCl$_3$) δ 7.87 (s, 1H), 7.56-7.52 (m, 2H), 7.36-7.29 (m, 3H), 3.70 (t, J = 4.9 Hz, 4H), 2.42 (t, J = 5.0 Hz, 4H), 2.28 (s, 3H). LCMS (Method 1); RT = 1.00 min. Calculated [M + H]$^+$ = 312; Observed [M + H]$^+$ = 312. |
| 43 | 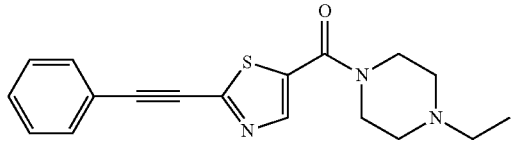 [SMILES: CCN1CCN(C(=O)c2cnc(C#Cc3ccccc3)s2)CC1] | (4-Ethyl-piperazin-1-yl)-(2-phenylethynyl-thiazol-5-yl)-methanone | $^1$H NMR (300 MHz, CDCl$_3$) δ 7.95 (s, 1H), 7.63-7.59 (m, 2H), 7.46-7.36 (m, 3H), 3.78 (t, J = 4.8 Hz, 4H), 2.53 (t, J = 4.8 Hz, 4H), 2.49 (q overlap triplet at 2.53 ppm, J = 7.2 Hz, 2H), 1.12 (t, J = 7.2 Hz, 3H). LCMS (Method 1), RT = 1.09 min. Calculated [M + H]$^+$ = 326; Observed [M + H]$^+$ = 326. |
| 44 | 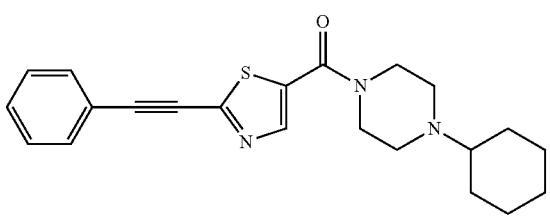 [SMILES: O=C(c1cnc(C#Cc2ccccc2)s1)N1CCN(C2CCCCC2)CC1] | (4-Cyclohexyl-piperazin-1-yl)-(2-phenylethynyl-thiazol-5-yl)-methanone | $^1$H NMR (300 MHz, DMSO-d$_6$) δ 8.19 (s, 1H), 7.70-7.66 (m, 2H), 7.54-7.49 (m, 3H), 3.60 (t, J = 5.0 Hz, 4H), 2.53 (t, J = 5.0 Hz, 4H), 2.06 (m, 1H), 1.75-1.72 (m, 4H), 1.19-1.15 (m, 6H). LCMS (Method 1), RT = 1.51 min. Calculated [M + H]$^+$ = 380; Observed [M + H]$^+$ = 380. |
| 45 | 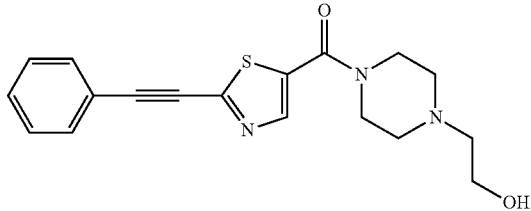 [SMILES: O=C(c1cnc(C#Cc2ccccc2)s1)N1CCN(CCO)CC1] | [4-(2-Hydroxy-ethyl)-piperazin-1-yl]-(2-phenylethynyl-thiazol-5-yl)-methanone | $^1$H NMR (300 MHz, CDCl$_3$) δ 7.95 (s, 1H), 7.63-7.59 (m, 2H), 7.47-7.36 (m, 3H), 3.78 (t, J = 5.0 Hz, 4H), 3.68 (t, J = 5.3 Hz, 2H), 2.63-2.58 (m, 6H). LCMS (Method 1), RT = 0.87 min. Calculated [M + H]$^+$ = 342; Observed [M + H]$^+$ = 342. |
| 46 | 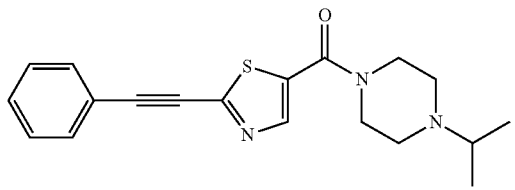 [SMILES: CC(C)N1CCN(C(=O)c2cnc(C#Cc3ccccc3)s2)CC1] | (4-Isopropyl-piperazin-1-yl)-(2-phenylethynyl-thiazol-5-yl)-methanone | $^1$H NMR (300 MHz, CDCl$_3$) δ 7.95 (s, 1H), 7.62-7.59 (m, 2H), 7.45-7.35 (m, 3H), 3.75 (t, J = 4.8 Hz, 4H), 2.75 (septet, J = 6.5 Hz, 1H), 2.57 (t, J = 4.9 Hz, 2H), 1.05 (d, J = 6.5 Hz, 6H). LCMS (Method 1), RT = 1.16 min. Calculated [M + H]$^+$ = 340; Observed [M + H]$^+$ = 340. |

TABLE 1-continued

| Example | Compound Name | Characterization |
|---|---|---|
| 47 | 4-(2-Phenylethynyl-thiazole-5-carbonyl)-piperazin-2-one | $^1$H NMR (300 MHz, CDCl$_3$) δ 8.04 (s, 1H), 7.62-7.59 (m, 2H), 7.47-7.36 (m, 3H), 6.95 (br s, 1H), 4.41 (s, 2H), 3.96 (t, J = 5.3 Hz, 2H), 3.51 (br m, 2H). LCMS (Method 1), RT = 0.82 min. Calculated [M + H]$^+$ = 312; Observed [M + H]$^+$ = 312. |
| 48 | Piperidin-1-yl-(2-p-tolylethynyl-thiazol-5-yl)-methanone | $^1$H NMR (300 MHz, CDCl$_3$) δ 7.93 (s, 1H), 7.53-7.47 (m, 2H), 7.23-7.17 (m, 2H), 3.73-3.62 (m, 4H), 2.39 (s, 3H), 1.79-1.59 (m, 6H). LCMS (Method 3), RT = 1.53 min. Calculated [M + H]$^+$ = 311; Observed [M + H]$^+$ = 311. |
| 49 | [2-p-Tolylethynyl-thiazole-5-carboxylic acid cyclopentylamide | $^1$H NMR (300 MHz, CDCl$_3$) δ 8.11 (s, 1H), 7.53-7.46 (m, 2H), 7.24-7.17 (m, 2H), 6.04 (d, J = 7.2 Hz, 1H), 4.45-4.31 (m, 1H), 2.39 (s, 3H), 2.19-2.03 (m, 2H), 1.82-1.44 (m, 6H). LCMS (Method 3), RT = 1.54 min. Calculated [M + H]$^+$ = 311; Observed [M + H]$^+$ = 311. |
| 50 | (4-Hydroxy-piperidin-1-yl)-(2-p-tolylethynyl-thiazol-5-yl)-methanone | $^1$H NMR (300 MHz, CDCl$_3$) δ 7.94 (s, 1H), 7.53-7.47 (m, 2H), 7.24-7.17 (m, 2H), 4.13-3.96 (m, 3H), 3.56-3.43 (m, 2H), 2.39 (s, 3H), 2.14-1.90 (m, 3H), 1.72-1.57 (m, 2H). LCMS (Method 3), RT = 1.17 min. Calculated [M + H]$^+$ = 327; Observed [M + H]$^+$ = 327. |
| 51 | Pyrrolidin-1-yl-(2-p-tolylethynyl-thiazol-5-yl)-methanone | $^1$H NMR (300 MHz, CDCl$_3$) δ 8.16 (s, 1H), 7.54-7.47 (m, 2H), 7.23-7.17 (m, 2H), 3.83-3.62 (m, 4H), 2.39 (s, 3H), 2.14-1.90 (m, 4H). LCMS (Method 3), RT = 1.37 min. Calculated [M + H]$^+$ = 297; Observed [M + H]$^+$ = 297. |
| 52 | (4-Methyl-piperidin-1-yl)-(2-p-tolylethynyl-thiazol-5-yl)-methanone | $^1$H NMR (300 MHz, CDCl$_3$) δ 7.93 (s, 1H), 7.53-7.46 (m, 2H), 7.23-7.16 (m, 2H), 4.78-3.89 (br s, 2H), 3.27-2.64 (br s, 2H), 2.39 (s, 3H), 1.82-1.60 (m, 3H), 1.31-1.12 (m, 2H), 1.00 (d, J = 6.3 Hz, 3H). LCMS (Method 3), RT = 1.59 min. Calculated [M + H]$^+$ = 325; Observed [M + H]$^+$ = 325. |
| 53 | Morpholin-4-yl-(2-p-tolylethynyl-thiazol-5-yl)-methanone | $^1$H NMR (300 MHz, CDCl$_3$) δ 7.96 (s, 1H), 7.54-7.48 (m, 2H), 7.25-7.18 (m, 2H), 3.77 (s, 8H), 2.40 (s, 3H). LCMS (Method 3), RT = 1.30 min. Calculated [M + H]$^+$ = 313; Observed [M + H]$^+$ = 313. |
| 54 | [2-(4-Chloro-phenylethynyl)-thiazol-5-yl]-piperidin-1-yl-methanone | $^1$H NMR (300 MHz, CDCl$_3$) δ 7.94 (s, 1H), 7.57-7.51 (m, 2H), 7.41-7.35 (m, 2H), 3.73-3.62 (m, 4H), 1.79-1.60 (m, 6H). LCMS (Method 3), RT = 1.54 min. Calculated [M + H]$^+$ = 331; Observed [M + H]$^+$ = 331 |
| 55 | [2-(4-Chloro-phenylethynyl)-thiazol-5-yl]-(4-hydroxy-piperidin-1-yl)-methanone | $^1$H NMR (300 MHz, CDCl$_3$) δ 7.96 (s, 1H), 7.57-7.52 (m, 2H), 7.41-7.36 (m, 2H), 4.12-3.95 (m, 3H), 3.57-3.44 (m, 2H), 2.04-1.90 (m, 2H), 1.86-1.56 (m, 3H). LCMS (Method 3), RT = 1.19 min. Calculated [M + H]$^+$ = 347; Observed [M + H]$^+$ = 347. |

TABLE 1-continued

| Example | Compound | Compound Name | Characterization |
|---|---|---|---|
| 56 | | [2-(4-Chloro-phenylethynyl)-thiazol-5-yl]-morpholin-4-yl-methanone | $^1$H NMR (300 MHz, CDCl$_3$) δ 7.97 (s, 1H), 7.57-7.52 (m, 2H), 7.42-7.36 (m, 2H), 3.77 (s, 8H). LCMS (Method 3), RT = 1.31 min. Calculated [M + H]$^+$ = 333; Observed [M + H]$^+$ = 333. |
| 57 | | [2-(4-Chloro-phenylethynyl)-thiazol-5-yl]-(4-methyl-piperidin-1-yl)-methanone | $^1$H NMR (300 MHz, CDCl3) δ 7.94 (s, 1H), 7.57-7.51 (m, 2H), 7.41-7.36 (m, 2H), 4.77-3.96 (br s, 2H), 3.28-2.66 (br s, 2H), 1.83-1.61 (m, 3H), 1.36-1.12 (m, 2H), 1.01 (d, J = 6.4 Hz, 3H). LCMS (Method 3), RT = 1.62 min. Calculated [M + H]$^+$ = 345; Observed [M + H]$^+$ = 345. |
| 58 | | Azepan-1-yl-(2-phenylethynyl-thiazol-5-yl)-methanone | $^1$H NMR (300 MHz, CDCl$_3$) δ 8.00 (s, 1H), 7.63-7.59 (m, 2H), 7.47-7.36 (m, 3H), 3.68 (dd, J = 5.9 Hz, 4H), 1.82 (br s, 4H), 1.65-1.61 (m, 4H). LCMS (Method 1), RT = 1.50 min. Calculated [M + H]$^+$ = 311; Observed [M + H]$^+$ = 311. |
| 59 | | 2-(2-Fluoro-phenylethynyl)-thiazole-5-carboxylic acid cyclopentylamide | $^1$H NMR (300 MHz, CDCl$_3$) δ 8.14 (s, 1H), 7.62-7.55 (m, 1H), 7.47-7.38 (m, 1H), 7.22-7.10 (m, 2H), 6.09 (d, J = 7.2 Hz, 1H), 4.44-4.31 (m, 1H), 2.18-2.03 (m, 2H), 1.82-1.45 (m, 6H). LCMS (Method 3), RT = 1.48 min. Calculated [M + H]$^+$ = 315; Observed [M + H]$^+$ = 315. |
| 60 | | [2-(2-Fluoro-phenylethynyl)-thiazol-5-yl]-(4-hydroxy-piperidin-1-yl)-methanone | $^1$H NMR (300 MHz, CDCl$_3$) δ 7.97 (s, 1H), 7.63-7.55 (m, 1H), 7.47-7.38 (m, 1H), 7.22-7.10 (m, 2H), 4.13-3.95 (m, 3H), 3.58-3.43 (m, 2H), 2.06-1.77 (m, 3H), 1.73-1.56 (m, 2H). LCMS (Method 3), RT = 1.09 min. Calculated [M + H]$^+$ = 331; Observed [M + H]$^+$ = 331. |
| 61 | | [2-(2-Fluoro-phenylethynyl)-thiazol-5-yl]-morpholin-4-yl-methanone | $^1$H NMR (300 MHz, CDCl$_3$) δ 7.98 (s, 1H), 7.63-7.55 (m, 1H), 7.47-7.38 (m, 1H), 7.22-7.11 (m, 2H), 3.76 (s, 8H). LCMS (Method 3), RT = 1.21 min. Calculated [M + H]$^+$ = 317; Observed [M + H]$^+$ = 317. |
| 62 | | [2-(2-Fluoro-phenylethynyl)-thiazol-5-yl]-piperidin-1-yl-methanone | $^1$H NMR (300 MHz, CDCl$_3$) δ 7.96 (s, 1H), 7.63-7.55 (m, 1H), 7.47-7.38 (m, 1H), 7.22-7.10 (m, 2H), 3.75-3.61 (m, 4H), 1.79-1.60 (m, 6H). LCMS (Method 3), RT = 1.44 min. Calculated [M + H]$^+$ = 315; Observed [M + H]$^+$ = 315. |
| 63 | | [2-(2-Fluoro-phenylethynyl)-thiazol-5-yl]-(4-methyl-piperidin-1-yl)-methanone | $^1$H NMR (300 MHz, CDCl$_3$) δ 7.96 (s, 1H), 7.62-7.55 (m, 1H), 7.46-7.37 (m, 1H), 7.21-7.10 (m, 2H), 4.86-3.85 (br s, 2H), 3.37-2.61 (br s, 2H), 1.83-1.61 (m, 3H), 1.35-1.12 (m, 2H), 1.00 (d, J = 6.4 Hz, 3H). LCMS (Method 3), RT = 1.55 min. Calculated [M + H]$^+$ = 329; Observed [M + H]$^+$ = 329. |
| 64 | | 2-(2-Chloro-phenylethynyl)-thiazole-5-carboxylic acid cyclopentylamide | $^1$H NMR (300 MHz, CDCl$_3$) δ 8.16 (s, 1H), 7.62 (dd, J = 7.5, 1.9 Hz, 1H), 7.49-7.42 (m, 1H), 7.40-7.24 (m, 2H), 6.18 (d, J = 7.2 Hz, 1H), 4.44-4.30 (m, 1H), 2.17-2.02 (m, 2H), 1.82-1.43 (m, 6H). LCMS (Method 3), RT = 1.54 min. Calculated [M + H]$^+$ = 331; Observed [M + H]$^+$ = 331. |

TABLE 1-continued

| Example | Compound | Compound Name | Characterization |
|---|---|---|---|
| 65 | | [2-(2-Chloro-phenylethynyl)-thiazol-5-yl]-(4-hydroxy-piperidin-1-yl)-methanone | $^1$H NMR (300 MHz, CDCl$_3$) δ 7.97 (s, 1H), 7.62 (dd, J = 7.6, 1.7 Hz, 1H), 7.50-7.43 (m, 1H), 7.41-7.25 (m, 2H), 4.17-3.91 (m, 3H), 3.60-3.41 (m, 2H), 2.19-1.85 (m, 3H), 1.76-1.54 (m, 2H). LCMS (Method 3), RT = 1.16 min. Calculated [M + H]$^+$ = 347; Observed [M + H]$^+$ = 347. |
| 66 | | [2-(2-Chloro-phenylethynyl)-thiazol-5-yl]-morpholin-4-yl-methanone | $^1$H NMR (300 MHz, CDCl$_3$) δ 7.99 (s, 1H), 7.63 (dd, J = 7.6, 1.7 Hz, 1H), 7.50-7.44 (m, 1H), 7.41-7.26 (m, 2H), 3.76 (s, 8H). LCMS (Method 3), RT = 1.28 min. Calculated [M + H]$^+$ = 333; Observed [M + H]$^+$ = 333. |
| 67 | | [2-(2-Chloro-phenylethynyl)-thiazol-5-yl]-(4-methyl-piperidin-1-yl)-methanone | $^1$H NMR (300 MHz, CDCl$_3$) δ 7.96 (s, 1H), 7.63 (dd, J = 7.6, 1.7 Hz, 1H), 7.50-7.44 (m, 1H), 7.41-7.25 (m, 2H), 4.82-3.86 (br s, 2H), 3.35-2.61 (br s, 2H), 1.83-1.61 (m, 3H), 1.35-1.12 (m, 2H), 1.00 (d, J = 6.2 Hz, 3H). LCMS (Method 3), RT = 1.62 min. Calculated [M + H]$^+$ = 345; Observed [M + H]$^+$ = 345. |
| 68 | | [2-(2-Chloro-phenylethynyl)-thiazol-5-yl]-piperidin-1-yl-methanone | $^1$H NMR (300 MHz, CDCl$_3$) δ 7.96 (s, 1H), 7.63 (dd, J = 7.6, 1.8 Hz, 1H), 7.49-7.44 (m, 1H), 7.40-7.26 (m, 2H), 3.74-3.62 (m, 4H), 1.79-1.60 (m, 6H). LCMS (Method 3), RT = 1.52 min. Calculated [M + H]$^+$ = 331; Observed [M + H]$^+$ = 331. |
| 69 | | Piperidin-1-yl-(2-o-tolylethynyl-thiazol-5-yl)-methanone | $^1$H NMR (300 MHz, CDCl$_3$) δ 7.94 (s, 1H), 7.57 (d, J = 7.6 Hz, 1H), 7.36-7.17 (m, 3H), 3.72-3.63 (m, 4H), 2.54 (s, 3H), 1.79-1.61 (m, 6H). LCMS (Method 3), RT = 1.52 min. Calculated [M + H]$^+$ = 311; Observed [M + H]$^+$ = 311. |
| 70 | | (4-Hydroxy-piperidin-1-yl)-(2-o-tolylethynyl-thiazol-5-yl)-methanone | $^1$H NMR (300 MHz, CDCl$_3$) δ 7.95 (s, 1H), 7.56 (d, J = 7.7 Hz, 1H), 7.37-7.17 (m, 3H), 4.14-3.95 (m, 3H), 3.57-3.44 (m, 2H), 2.53 (s, 3H), 2.07-1.85 (m, 3H), 1.74-1.56 (m, 2H). LCMS (Method 3), RT = 1.16 min. Calculated [M + H]$^+$ = 327; Observed [M + H]$^+$ = 327. |
| 71 | | Morpholin-4-yl-(2-o-tolylethynyl-thiazol-5-yl)-methanone | $^1$H NMR (300 MHz, CDCl$_3$) δ 7.97 (s, 1H), 7.57 (d, J = 7.6 Hz, 1H), 7.37-7.17 (m, 3H), 3.77 (s, 8H), 2.53 (s, 3H). LCMS (Method 3), RT = 1.29 min. Calculated [M + H]$^+$ = 313; Observed [M + H]$^+$ = 313. |
| 72 | | (4-Methyl-piperidin-1-yl)-(2-o-tolylethynyl-thiazol-5-yl)-methanone | $^1$H NMR (300 MHz, CDCl$_3$) δ 7.94 (s, 1H), 7.56 (d, J = 7.7 Hz, 1H), 7.36-7.17 (m, 3H), 4.87-3.83 (br s, 2H), 3.27-2.73 (br s, 2H), 2.53 (s, 3H), 1.83-1.61 (m, 3H), 1.34-1.12 (m, 2H), 1.00 (d, J = 6.4 Hz, 3H). LCMS (Method 3), RT = 1.62 min. Calculated [M + H]$^+$ = 325; Observed [M + H]$^+$ = 325. |
| 73 | | 2-o-Tolylethynyl-thiazole-5-carboxylic acid cyclopentylamide | $^1$H NMR (300 MHz, CDCl$_3$) δ 8.13 (s, 1H), 7.56 (d, J = 7.6 Hz, 1H), 7.38-7.17 (m, 3H), 6.11 (d, J = 7.1 Hz, 1H), 4.45-4.31 (m, 1H), 2.53 (s, 3H), 2.20-2.03 (m, 2H), 1.84-1.45 (m, 6H). LCMS (Method 3), RT = 1.54 min. Calculated [M + H]$^+$ = 311; Observed [M + H]$^+$ = 311. |

TABLE 1-continued

| Example | Compound | Compound Name | Characterization |
|---|---|---|---|
| 74 | | Pyrrolidin-1-yl-(2-o-tolylethynyl-thiazol-5-yl)-methanone | $^1$H NMR (300 MHz, CDCl$_3$) δ 8.17 (s, 1H), 7.57 (d, J = 7.7 Hz, 1H), 7.36-7.17 (m, 3H), 3.82-3.63 (m, 4H), 2.54 (s, 3H), 2.13-1.91 (m, 4H). LCMS (Method 3), RT = 1.40 min. Calculated [M + H]$^+$ = 297; Observed [M + H]$^+$ = 297. |
| 75 | | 1-(2-Phenylethynyl-thiazole-5-carbonyl)-piperidin-4-one | $^1$H NMR (300 MHz, CDCl$_3$) δ 8.04 (s, 1H), 7.63-7.59 (m, 2H), 7.47-7.32 (m, 3H), 4.03 (t, J = 6.3 Hz, 4H), 2.59 (t, J = 6.3 Hz, 4H). LCMS (Method 1), RT = 1.05 min. Calculated [M + H]$^+$ = 311; Observed [M + H]$^+$ = 311. |
| 76 | | (2-Phenylethynyl-thiazol-5-yl)-(1,4,6,7-tetrahydro-imidazo[4,5-c]pyridin-5-yl)-methanone | $^1$H NMR (300 MHz, CDCl$_3$) δ 8.04 (s, 1H), 7.63-7.59 (m, 2H), 7.59 (s, 1H), 7.46-7.36 (m, 3H), 4.81(s, 2H), 4.02 (br m, 2H), 2.86 (t, J = 5.5 Hz, 2H). LCMS (Method 1), RT = 0.89 min. Calculated [M + H]$^+$ = 335; Observed [M + H]$^+$ = 335. |
| 77 | | (2-Phenylethynyl-thiazol-5-yl)-(1,4,6,7-tetrahydro-pyrazolo[4,3-c]pyridin-5-yl)-methanone | $^1$H NMR (300 MHz, CDCl$_3$) δ 8.06 (s, 1H), 7.63-7.59 (m, 2H), 7.46-7.36 (m, 4H), 4.80(s, 2H), 4.00 (br t, J = 5.7 Hz, 2H), 2.95 (t, J = 5.8 Hz, 2H). LCMS (Method 1), RT = 0.99 min. Calculated [M + H]$^+$ = 335; Observed [M + H]$^+$ = 335. |
| 78 | | (1-Oxa-8-aza-spiro[4.5]dec-8-yl)-2-phenylethynyl-thiazol-5-yl)-methanone | $^1$H NMR (300 MHz, CDCl$_3$) δ 7.94 (s, 1H), 7.63-7.59 (m, 2H), 7.45-7.35 (m, 3H), 4.01 (br s, 2H), 3.89 (t, J = 6.7 Hz, 2H), 3.52 (br s, 2H), 1.96 (pentet, J = 7.1 Hz, 2H), 1.77-1.59 (m, 6H). LCMS (Method 1), RT = 1.39 min. Calculated [M + H]$^+$ = 353; Observed [M + H]$^+$ = 353. |
| 79 | | 8-(2-Phenylethynyl-thiazole-5-carbonyl)-1-oxa-8-aza-spiro[4.5]decan-2-one | $^1$H NMR (300 MHz, CDCl$_3$) δ 7.96 (s, 1H), 7.63-7.59 (m, 2H), 7.47-7.36 (m, 3H), 4.25 (br s, 2H), 3.49 (br s, 2H), 2.67 (t, J = 8.3 Hz, 2H), 2.11 (t, J = 8.3 Hz, 2H), 1.97-1.75 (m, 4H). LCMS (Method 1), RT = 1.13 min. Calculated [M + H]$^+$ = 367; Observed [M + H]$^+$ = 367. |
| 80 | | (4-Hydroxy-4-methyl-piperidin-1-yl)-(2-phenylethynyl-thiazol-5-yl)-methanone | $^1$H NMR (300 MHz, CDCl$_3$) δ 7.94 (s, 1H), 7.63-7.59 (m, 2H), 7.45-7.35 (m, 3H), 4.08 (br s, 2H), 3.48 (br s, 2H), 1.68-1.65 (m, 4H), 1.33 (s, 3H). LCMS (Method 1), RT = 1.05 min. Calculated [M + H]$^+$ = 327; Observed [M + H]$^+$ = 327. |
| 81 | | ((R)-3-Hydroxy-piperidin-1-yl)-(2-phenylethynyl-thiazol-5-yl)-methanone | $^1$H NMR (300 MHz, CDCl$_3$) δ 8.01 (s, 1H), 7.61-7.58 (m, 2H), 7.45-7.35 (m, 3H), 3.92-3.60 (m, 2H), 3.58-3.54 (m, 3H), 2.25 (br s, 1H), 1.97-1.87 (m, 2H), 1.77-1.61 (m, 2H). LCMS (Method 1), RT = 0.99 min. Calculated [M + H]$^+$ = 313; Observed [M + H]$^+$ = 313. |

TABLE 1-continued

| Example | Compound Name | Characterization |
|---|---|---|
| 82 | (4,4-Difluoro-piperidin-1-yl)-(2-phenylethynyl-thiazol-5-yl)-methanone; | $^1$H NMR (300 MHz, CDCl$_3$) δ 7.99 (s, 1H), 7.66-7.59 (m, 2H), 7.49-7.37 (m, 3H), 3.92-3.82 (m, 4H), 2.18-2.01 (m, 4H). LCMS (Method 3), RT = 1.43 min. Calculated [M + H]$^+$ = 333; Observed [M + H]$^+$ = 333. |
| 83 | (4,4-Difluoro-piperidin-1-yl)-[2-(3-fluoro-phenylethynyl)-thiazol-5-yl]-methanone | $^1$H NMR (300 MHz, CDCl$_3$) δ 8.00 (s, 1H), 7.43-7.28 (m, 3H), 7.21-7.12 (m, 1H), 3.91-3.82 (m, 4H), 2.18-2.00 (m, 4H). LCMS (Method 3), RT = 1.45 min. Calculated [M + H]$^+$ = 351; Observed [M + H]$^+$ = 351. |
| 84 | [2-(3-Fluoro-phenylethynyl)-thiazol-5-yl]-(4-fluoro-piperidin-1-yl)-methanone | $^1$H NMR (300 MHz, CDCl$_3$) δ 7.98 (s, 1H), 7.43-7.28 (m, 3H), 7.21-7.11 (m, 1H), 4.96 (dsept, J = 48, 2.8 Hz, 1H), 4.08-3.83 (m, 2H), 3.79-3.60 (m, 2H), 2.09-1.80 (m, 4H). LCMS (Method 3), RT = 1.39 min. Calculated [M + H]$^+$ = 333; Observed [M + H]$^+$ = 333. |
| 85 | (3,3-Difluoro-piperidin-1-yl)-(2-phenylethynyl-thiazol-5-yl)-methanone | $^1$H NMR (300 MHz, CDCl$_3$) δ 8.00 (s, 1H), 7.66-7.58 (m, 2H), 7.48-7.36 (m, 3H), 4.00-3.84 (m, 2H), 3.78-3.68 (m, 2H), 2.22-2.05 (m, 2H), 1.95-1.84 (m, 2H). LCMS (Method 3), RT = 1.44 min. Calculated [M + H]$^+$ = 333; Observed [M + H]$^+$ = 333. |
| 86 | 2-Phenylethynyl-thiazole-4-carboxylic acid cyclopropylamide | LCMS (Method 5), RT = 1.33 min. Calculated [M + H]$^+$ = 269; Observed [M + H]$^+$ = 269. |
| 87 | 2-Phenylethynyl-thiazole-4-carboxylic acid benzylamide | LCMS (Method 5), RT = 1.57 min. Calculated [M + H]$^+$ = 319; Observed [M + H]$^+$ = 319. |
| 88 | 2-Phenylethynyl-thiazole-4-carboxylic acid o-tolylamide | LCMS (Method 5), RT = 1.70 min. Calculated [M + H]$^+$ = 319; Observed [M + H]$^+$ = 319. |

TABLE 1-continued

| Example | Compound | Compound Name | Characterization |
|---|---|---|---|
| 89 | | 2-Phenylethynyl-thiazole-4-carboxylic acid (2-chloro-phenyl)-amide | LCMS (Method 5), RT = 1.87 min. Calculated [M + H]⁺ = 339; Observed [M + H]⁺ = 339. |
| 90 | | 2-Phenylethynyl-thiazole-4-carboxylic acid ethylamide | LCMS (Method 5), RT = 1.31 min. Calculated [M + H]⁺ = 257; Observed [M + H]⁺ = 257. |
| 91 | | 2-Phenylethynyl-thiazole-4-carboxylic acid phenylamide | LCMS (Method 5), RT = 1.63 min. Calculated [M + H]⁺ = 305; Observed [M + H]⁺ = 305. |
| 92 | | 2-Phenylethynyl-thiazole-4-carboxylic acid isopropylamide | LCMS (Method 5), RT = 1.45 min. Calculated [M + H]⁺ = 271; Observed [M + H]⁺ = 271. |
| 93 | | 2-Phenylethynyl-thiazole-4-carboxylic acid m-tolylamide | LCMS (Method 5), RT = 1.74 min. Calculated [M + H]⁺ = 319; Observed [M + H]⁺ = 319. |
| 94 | | 2-Phenylethynyl-thiazole-4-carboxylic acid cyclohexylamide | LCMS (Method 5), RT = 1.71 min. Calculated [M + H]⁺ = 311; Observed [M + H]⁺ = 311. |
| 95 | | 2-Phenylethynyl-thiazole-4-carboxylic acid (4-chloro-phenyl)-amide | LCMS (Method 5), RT = 1.78 min. Calculated [M + H]⁺ = 339; Observed [M + H]⁺ = 339. |
| 96 | | 2-Phenylethynyl-thiazole-4-carboxylic acid p-tolylamide | LCMS (Method 5), RT = 1.73 min. Calculated [M + H]⁺ = 319; Observed [M + H]⁺ = 319. |

TABLE 1-continued

| Example | Compound | Compound Name | Characterization |
|---|---|---|---|
| 97 | | 2-Phenylethynyl-thiazole-4-carboxylic acid cyclopentylamide | LCMS (Method 5), RT = 1.60 min. Calculated [M + H]$^+$ = 297; Observed [M + H]$^+$ = 297. |
| 98 | | 2-Phenylethynyl-thiazole-4-carboxylic acid cyclopropylmethyl-amide | LCMS (Method 5), RT = 1.48 min. Calculated [M + H]$^+$ = 283; Observed [M + H]$^+$ = 283. |
| 99 | | 2-Phenylethynyl-thiazole-5-carboxylic acid (4-chloro-phenyl)-amide | LCMS (Method 5), RT = 1.66 min. Calculated [M + H]$^+$ = 339; Observed [M + H]$^+$ = 339. |
| 100 | | 2-Phenylethynyl-thiazole-5-carboxylic acid phenylamide | LCMS (Method 5), RT = 1.50 min. Calculated [M + H]$^+$ = 305; Observed [M + H]$^+$ = 305. |
| 101 | | 2-Phenylethynyl-thiazole-5-carboxylic acid cyclopropylmethyl-amide | LCMS (Method 5), RT = 1.33 min. Calculated [M + H]$^+$ = 283; Observed [M + H]$^+$ = 283. |
| 102 | | 2-Phenylethynyl-thiazole-5-carboxylic acid m-tolylamide | LCMS (Method 5). RT = 1.60 min. Calculated [M + H]$^+$ = 319; Observed [M + H]$^+$ = 319. |
| 103 | | 2-Phenylethynyl-thiazole-5-carboxylic acid isopropylamide | LCMS (Method 5), RT = 1.28 min. Calculated [M + H]$^+$ = 271; Observed [M + H]$^+$ = 271. |
| 104 | | 2-Phenylethynyl-thiazole-5-carboxylic acid cyclopentylamide | LCMS (Method 5), RT = 1.43 min. Calculated [M + H]$^+$ = 297; Observed [M + H]$^+$ = 297. |
| 105 | | 2-Phenylethynyl-thiazole-5-carboxylic acid p-tolylamide | LCMS (Method 5), RT = 1.59 min. Calculated [M + H]$^+$ = 319; Observed [M + H]$^+$ = 319. |

TABLE 1-continued

| Example | Compound | Compound Name | Characterization |
|---|---|---|---|
| 106 | | 2-Phenylethynyl-thiazole-5-carboxylic acid o-tolylamide | LCMS (Method 5), RT = 1.49 min. Calculated [M + H]$^+$ = 319; Observed [M + H]$^+$ = 319. |
| 107 | | 2-Phenylethynyl-thiazole-5-carboxylic acid benzylamide | LCMS (Method 5), RT = 1.45 min. Calculated [M + H]$^+$ = 319; Observed [M + H]$^+$ = 319 |
| 108 | | 2-Phenylethynyl-thiazole-5-carboxylic acid cyclopropylamide | LCMS (Method 5), RT = 1.19 min. Calculated [M + H]$^+$ = 269; Observed [M + H]$^+$ = 269. |
| 109 | | 2-Phenylethynyl-thiazole-5-carboxylic acid ethylamide | LCMS (Method 5), RT = 1.17 min. Calculated [M + H]$^+$ = 257; Observed [M + H]$^+$ = 257. |
| 110 | | 2-Phenylethynyl-thiazole-5-carboxylic acid cyclohexylamide | LCMS (Method 5), RT = 1.65 min. Calculated [M + H]$^+$ = 311; Observed [M + H]$^+$ = 311. |
| 111 | | (2-Phenylethynyl-thiazol-5-yl)-(4-trifluoromethyl-piperidin-1-yl)-methanone | $^1$H NMR (400 MHz, DMSO-d$_6$) δ 8.24 (s, 1H), 7.77-7.63 (m, 2H), 7.61-7.44 (m, 3H), 4.68-3.91 (br s, 2H), 3.49-2.82 (br s, 2H), 2.80-2.61 (m, 1H), 2.04-1.80 (m, 2H), 1.64-1.38 (m, 2H). LCMS (Method 7), RT = 4.566 min. Calculated [M + H]$^+$ = 365; Observed [M + H]$^+$ = 365. Yield 46% |
| 112 | | 2-Phenylethynyl-thiazole-5-carboxylic acid diethylamide | $^1$H NMR (400 MHz, DMSO-d$_6$) δ 8.19 (s, 1H), 7.77-7.63 (m, 2H), 7.60-7.43 (m, 3H), 3.62-3.40 (br s, 4H), 1.30-1.05 (br s, 6H).LCMS (Method 7), RT = 4.406 min. Calculated [M + H]$^+$ = 285; Observed [M + H]$^+$ = 285. Yield 71% |
| 113 | | (3-Dimethylamino-pyrrolidin-1-yl)-(2-phenylethynyl-thiazol-5-yl)-methanone | $^1$H NMR (400 MHz, DMSO-d$_6$) δ 8.48-8.29 (m, 1H), 7.78-7.62 (m, 2H), 7.62-7.37 (m, 3H), 4.05-3.86 (m, 1H), 3.86-3.50 (m, 2H), 3.50-3.12 (1H, hidden under H2O peak), 2.87-2.65 (m, 1H), 2.29-1.98 (m, 1H), 2.20 (s, 6H), 1.94-1.65 (m, 1H). LCMS (Method 7), RT = 3.178 min. Calculated [M + H]$^+$ = 326; Observed [M + H]$^+$ = 326. Yield 26% |

TABLE 1-continued

| Example | Compound Name | Characterization |
|---|---|---|
| 114 | (3,3-Difluoro-azetidin-1-yl)-(2-phenylethynyl-thiazol-5-yl)-methanone | $^1$H NMR (400 MHz, DMSO-d$_6$) δ 8.34 (s, 1H), 7.75-7.64 (m, 2H), 7.59-7.45 (m, 3H), 5.22-4.82 (br s, 2H), 4.73-4.34 (br s, 2H). LCMS (Method 7), RT = 4.307 min. Calculated [M + H]$^+$ = 305; Observed [M + H]$^+$ = 305. Yield 55% |
| 115 | (3,3-Difluoro-pyrrolidin-1-yl)-(2-phenylethynyl-thiazol-5-yl)-methanone | $^1$H NMR (400 MHz, CD$_3$OD) δ 8.36-8.23 (br s, 1H), 7.69-7.57 (m, 2H), 7.55-7.38 (m, 3H), 4.36-3.77 (m, 4H), 2.68-2.40 (m, 2H). LCMS (Method 7), RT = 4.336 min. Calculated [M + H]$^+$ = 319; Observed [M + H]$^+$ = 319. Yield 43% |
| 116 | 2-Phenylethynyl-thiazole-5-carboxylic acid dimethylamide | $^1$H NMR (400 MHz, DMSO-d$_6$) δ 8.29 (s, 1H), 7.75-7.63 (m, 2H), 7.60-7.44 (m, 3H), 3.22 (br s, 3H), 3.02 (br s, 3H). LCMS (Method 7), RT = 3.99 min. Calculated [M + H]$^+$ = 257; Observed [M + H]$^+$ = 257. Yield 36% |
| 117 | (4-Dimethylamino-piperidin-1-yl)-(2-phenylethynyl-thiazol-5-yl)-methanone | $^1$H NMR (400 MHz, DMSO-d$_6$) δ 8.20 (s, 1H), 7.76-7.62 (m, 2H), 7.60-7.41 (m, 3H), 4.60-3.86 (br m, 2H), 3.60-2.78 (br m, 2H hidden under H2O peak), 2.64-2.39 (m, 1H, hidden under DMSO peak), 2.27 (s, 6H), 1.94-1.76 (m, 2H), 1.55-1.33 (m, 2H). LCMS (Method 7), RT = 3.245 min. Calculated [M + H]$^+$ = 340; Observed [M + H]$^+$ = 340. Yield 28% |
| 118 | (2-Phenylethynyl-thiazol-5-yl)-(4-pyrrolidin-1-yl-piperidin-1-yl)-methanone | $^1$H NMR (400 MHz, DMSO-d$_6$) δ 8.19 (s, 1H), 7.76-7.62 (m, 2H), 7.60-7.42 (m, 3H), 4.35-3.82 (br m, 2H), 3.54-2.87 (br m, 2H, hidden under H$_2$O peak), 2.72-2.39 (m, 4H, hidden under DMSO peak), 2.39-2.21 (m, 1H), 2.00-1.82 (m, 2H), 1.80-1.59 (m 4H), 1.56-1.35 (m, 2H). LCMS (Method 7), RT = 3.325 min. Calculated [M + H]$^+$ = 366; Observed [M + H]$^+$ = 366. Yield 28% |
| 119 | (3-Methoxy-piperidin-1-yl)-(2-phenylethynyl-thiazol-5-yl)-methanone | $^1$H NMR (400 MHz, DMSO-d$_6$) δ 8.18 (s, 1H), 7.75-7.62 (m, 2H), 7.59-7.41 (m, 3H), 3.97-3.43 (br m, 4H), 3.43-3.33 (br s, 1H), 3.27-3.06 (br s, 3H), 1.96-1.55 (br m, 3H), 1.55-1.38 (m, 1H). LCMS (Method 7), RT = 4.298 min. Calculated [M + H]$^+$ = 327; Observed [M + H]$^+$ = 327. Yield 18% |

TABLE 1-continued

| Example | Compound | Compound Name | Characterization |
|---|---|---|---|
| 120 | | (3-Ethoxy-piperidin-1-yl)-(2-phenylethynyl-thiazol-5-yl)-methanone | ¹H NMR (400 MHz, DMSO-d₆) δ 8.19 (s, 1H), 7.76-7.64 (m, 2H), 7.59-7.43 (m, 3H), 4.01-3.38 (br m, 7H), 2.00-1.37 (m, 4H), 1.18-0.98 (m, 3H). LCMS (Method 7), RT = 5.746 min. Calculated [M + H]⁺ = 341; Observed [M + H]⁺ = 341. Yield 30% |
| 121 | | (4-Methoxy-piperidin-1-yl)-(2-phenylethynyl-thiazol-5-yl)-methanone | ¹H NMR (400 MHz, CDCl₃) δ 7.95 (s, 1H), 7.67-7.58 (m, 2H), 7.49-7.37 (m, 3H), 3.98-3.85 (m, 2H), 3.66-3.50 (m, 3H), 3.39 (s, 3H), 1.99-1.86 (m, 2H), 1.80-1.66 (m, 2H). LCMS (Method 7), RT = 3.52 min. Calculated [M + H]⁺ = 327; Observed [M + H]⁺ = 327. Yield 32% |
| 122 | | (4-Ethoxy-piperidin-1-yl)-(2-phenylethynyl-thiazol-5-yl)-methanone | ¹H NMR (400 MHz, DMSO-d₆) δ 8.20 (s, 1H), 7.74-7.63 (m, 2H), 7.58-7.44 (m, 3H), 3.94-3.75 (m, 2H), 3.63-3.53 (m, 1H), 3.48 (q, J = 7.0 Hz, 2H), 3.44-3.21 (m, 2H, hidden under H₂O peak), 1.95-1.81 (m, 2H), 1.57-1.42 (m, 2H), 1.12 (t, J = 7.0 Hz, 3H). LCMS (Method 7), RT = 5.561 min. Calculated [M + H]⁺ = 341; Observed [M + H]⁺ = 341. Yield 59% |
| 123 | | (3-Methoxymethyl-piperidin-1-yl)-(2-phenylethynyl-thiazol-5-yl)-methanone | ¹H NMR (400 MHz, CDCl₃) δ 7.98 (s, 1H), 7.65-7.57 (m, 2H), 7.47-7.35 (m, 3H), 4.66-3.85 (br m, 2H), 3.44-3.24 (m, 5H), 3.21-2.69 (br m, 2H), 1.99-1.74 (m, 3H), 1.47-1.20 (m, 2H). LCMS (Method 7), RT = 4.478 min. Calculated [M + H]⁺ = 341; Observed [M + H]⁺ = 341. Yield 78% |
| 124 | | (4-Methoxymethyl-piperidin-1-yl)-(2-phenylethynyl-thiazol-5-yl)-methanone | ¹H NMR (400 MHz, CDCl₃) δ 7.94 (s, 1H), 7.65-7.57 (m, 2H), 7.47-7.35 (m, 3H), 4.87-3.93 (br m, 2H), 3.36 (s, 3H), 3.28 (d, J = 6.1 Hz, 2H), 3.22-2.66 (br m, 2H), 2.00-1.76 (m, 3H), 1.40-1.18 (m, 2H). LCMS (Method 7), RT = 4.395 min. Calculated [M + H]⁺ = 341; Observed [M + H]⁺ = 341. Yield 48% |
| 125 | | (2-Phenylethynyl-thiazol-5-yl)-(3-pyrrolidin-1-yl-piperidin-1-yl)-methanone | LCMS (Method 7), RT = 8.51 min. Calculated [M + H]⁺ = 366; Observed [M + H]⁺ = 366. Yield 18% |

TABLE 1-continued

| Example | Compound Name | Characterization |
|---|---|---|
| 126 | 1-(2-Phenylethynyl-thiazole-5-carbonyl)-piperidine-4-carboxylic acid methyl ester | $^1$H NMR (400 MHz, DMSO-d$_6$) δ 8.20 (s, 1H), 7.72-7.64 (m, 2H), 7.57-7.45 (m, 3H), 4.37-3.84 (br m, 2H), 3.63 (s, 3H), 3.43-2.93 (br m, 2H), 2.78-2.64 (m, 1H), 1.99-1.85 (m, 2H), 1.69-1.51 (m, 2H). LCMS (Method 7), RT = 4.798 min. Calculated [M + H]$^+$ = 355; Observed [M + H]$^+$ = 355. Yield 32% |
| 127 | 1-(2-Phenylethynyl-thiazole-5-carbonyl)-piperidine-3-carboxylic acid methyl ester | LCMS (Method 7), RT = 4.88 min. Calculated [M + H]$^+$ = 355; Observed [M + H]$^+$ = 355. Yield 26% |
| 128 | Azetidin-1-yl-(2-phenylethynyl-thiazol-5-yl)-methanone | $^1$H NMR (400 MHz, DMSO-d$_6$) δ 8.25 (s, 1H), 7.74-7.63 (m, 2H), 7.59-7.44 (m, 3H), 4.58-4.42 (m, 2H), 4.15-3.99 (m, 2H), 2.39-2.24 (m, 2H). LCMS (Method 7), RT = 4.072 min. Calculated [M + H]$^+$ = 269; Observed [M + H]$^+$ = 269. Yield 86% |
| 129 | (3-Hydroxy-azetidin-1-yl)-(2-phenylethynyl-thiazol-5-yl)-methanone | $^1$H NMR (400 MHz, DMSO-d$_6$) δ 8.27 (s, 1H), 7.76-7.63 (m, 2H), 7.60-7.48 (m, 3H), 5.86 (br d, J = 5.9 Hz, 1H), 4.75-4.62 (m, 1H), 4.62-4.50 (m, 1H), 4.35-4.16 (m, 2H), 3.87-3.72 (m, 1H). LCMS (Method 7), RT = 3.572 min. Calculated [M + H]$^+$ = 285; Observed [M + H]$^+$ = 285. Yield 48% |
| 130 | N-[1-(2-Phenylethynyl-thiazole-5-carbonyl)-piperidin-4-yl]-acetamide | $^1$H NMR (400 MHz, CDCl$_3$) δ 7.95 (s, 1H), 7.65-7.57 (m, 2H), 7.48-7.35 (m, 3H), 5.41 (d, J = 7.2 Hz, 1H), 4.76-4.16 (br m, 2H), 4.16-4.03 (m, 1H), 3.41-2.83 (br m, 2H), 2.14-2.04 (m, 2H), 2.01 (s, 3H), 1.51-1.32 (m, 2H). LCMS (Method 7), RT = 2.921 min. Calculated [M + H]$^+$ = 354; Observed [M + H]$^+$ = 354. Yield 40% |
| 131 | N-[1-(2-Phenylethynyl-thiazole-5-carbonyl)-piperidin-3-yl]-acetamide | $^1$H NMR (400 MHz, CDCl$_3$) δ 8.09 (s, 1H), 7.67-7.56 (m, 2H), 7.48-7.34 (m, 3H), 5.65 (br s, 1H), 4.16-3.72 (br m, 3H), 3.72-3.24 (br m, 2H), 2.00 (s, 3H), 1.89-1.53 (br m, 4H). LCMS (Method 7), RT = 3.675 min. Calculated [M + H]$^+$ = 354; Observed [M + H]$^+$ = 354. Yield 22% |

TABLE 1-continued

| Example | Compound | Compound Name | Characterization |
|---|---|---|---|
| | | (2-Phenylethynyl-thiazol-5-yl)-(3-piperidin-1-yl-azetidin-1-yl)-methanone | $^1$H NMR (400 MHz, CDCl$_3$) δ 8.12 (s, 1H), 7.65-7.57 (m, 2H), 7.48-7.36 (m, 3H), 4.52-4.31 (m, 2H), 4.31-4.18 (m, 1H), 4.18-4.03 (m, 1H), 3.32-3.22 (m, 1H), 2.56-2.20 (m, 4H), 1.75-1.58 (m, 4H), 1.58-1.43 (m, 2H). LCMS (Method 7), RT = 5.571 min. Calculated [M + H]$^+$ = 352; Observed [M + H]$^+$ = 352. Yield 46% |
| 132 | | (3-Morpholin-4-yl-azetidin-1-yl)-(2-phenylethynyl-thiazol-5-yl)-methanone | $^1$H NMR (400 MHz, CDCl$_3$) δ 8.12 (s, 1H), 7.66-7.57 (m, 2H), 7.49-7.36 (m, 3H), 4.55-4.40 (m, 1H), 4.40-4.18 (m, 2H), 4.18-4.02 (m, 1H), 3.88-3.66 (m, 4H), 3.38-3.25 (m, 1H), 2.45 (br s, 4H). LCMS (Method 7), RT = 2.578 min. Calculated [M + H]$^+$ = 354; Observed [M + H]$^+$ = 354. Yield 35% |
| 133 | | (2-Phenylethynyl-thiazol-5-yl)-(3-pyrrolidin-1-yl-azetidin-1-yl)-methanone | $^1$H NMR (400 MHz, CDCl$_3$) δ 8.12 (s, 1H), 7.68-7.56 (m, 2H), 7.51-7.34 (m, 3H), 4.60-4.37 (m, 2H), 4.37-4.24 (m, 1H), 4.24-4.07 (m, 1H), 3.62-3.48 (m, 1H), 2.77-2.60 (m, 4H), 1.99-1.81 (m, 4H). LCMS (Method 7), RT = 5.423 min. Calculated [M + H]$^+$ = 338; Observed [M + H]$^+$ = 338. Yield 75% |
| 134 | | (2,3-Dihydro-benzo[1,4]oxazin-4-yl)-(2-phenylethynyl-thiazol-5-yl)-methanone | $^1$H NMR (400 MHz, DMSO-d$_6$) δ 8.24 (s, 1H), 7.77-7.63 (m, 2H), 7.61-7.41 (m, 4H), 7.15-7.02 (m, 1H), 7.00-6.90 (m, 1H), 6.90-6.77 (m, 1H), 4.42-4.27 (m, 2H), 4.13-3.98 (m, 2H). LCMS (Method 7), RT = 7.138 min. Calculated [M + H]$^+$ = 347; Observed [M + H]$^+$ = 347. Yield 26% |
| 135 | | (6,7-Dihydro-4H-thieno[3,2-c]pyridin-5-yl)-(2-phenylethynyl-thiazol-5-yl)-methanone | $^1$H NMR (400 MHz, DMSO-d$_6$) δ 8.32 (s, 1H), 7.76-7.63 (m, 2H), 7.60-7.44 (m, 3H), 7.44-7.31 (m, 1H), 7.02-6.83 (m, 1H), 4.93-4.56 (m, 2H), 4.01-3.80 (m, 2H), 3.11-2.80 (m, 2H). LCMS (Method 7), RT = 5.15 min. Calculated [M + H]$^+$ = 351; Observed [M + H]$^+$ = 351. Yield 20% |
| 136 | | (3-Methoxy-pyrrolidin-1-yl)-(2-phenylethynyl-thiazol-5-yl)-methanone | $^1$H NMR (400 MHz, DMSO-d$_6$) δ 8.39 (s, 1H), 7.74-7.63 (m, 2H), 7.59-7.44 (m, 3H), 4.12-3.96 (m, 1H), 3.96-3.72 (m, 2H), 3.67-3.43 (m, 2H), 3.26 (s, 3H), 2.19-1.88 (m, 2H). LCMS (Method 7), RT = 4.059 min. Calculated [M + H]$^+$ = 313; Observed [M + H]$^+$ = 313. Yield 30% |

TABLE 1-continued

| Example | Compound Name | Characterization |
|---|---|---|
| 137 | (3-Hydroxy-3-methyl-pyrrolidin-1-yl)-(2-phenylethynyl-thiazol-5-yl)-methanone | $^1$H NMR (400 MHz, CDCl$_3$) δ 8.21 and 8.13 (2 s, 1H, rotamers), 7.67-7.56 (m, 2H), 7.49-7.35 (m, 3H), 4.11-3.52 (m, 4H), 2.20-1.92 (m, 2H), 1.71 and 1.65 (2 s, 1H, rotamers), 1.53 (s, 3H). LCMS (Method 7), RT = 3.03 min. Calculated [M + H]$^+$ = 313; Observed [M + H]$^+$ = 313. Yield 22% |
| 138 | 1-(2-Phenylethynyl-thiazole-5-carbonyl)-pyrrolidine-3-carboxylic acid methyl ester | LCMS (Method 7), RT = 4.366 min. Calculated [M + H]$^+$ = 341; Observed [M + H]$^+$ = 341. Yield 71% |
| 139 | (Octahydro-isoindol-2-yl)-(2-phenylethynyl-thiazol-5-yl)-methanone | $^1$H NMR (400 MHz, DMSO-d$_6$) δ 8.40 (s, 1H), 7.75-7.64 (m, 2H), 7.59-7.45 (m, 3H), 3.86-3.75 (m, 1H), 3.71-3.61 (m, 1H), 3.56-3.45 (m, 1H), 3.44-3.25 (m, 1H, partially hidden by H$_2$O peak), 2.39-2.28 (m, 1H), 2.27-2.15 (m, 1H), 1.65-1.11 (m, 8H). LCMS (Method 7), RT = 4.918 min. Calculated [M + H]$^+$ = 337; Observed [M + H]$^+$ = 337. Yield 35% |
| 140 | 1-(2-Phenylethynyl-thiazole-5-carbonyl)-pyrrolidin-3-one | $^1$H NMR (400 MHz, DMSO-d$_6$) δ 8.42 (br s, 1H), 7.77-7.63 (m, 2H), 7.61-7.43 (m, 3H), 4.38-4.26 (m, 1H), 4.26-4.14 (m, 1H), 4.04-3.84 (m, 2H), 2.80-2.58 (m, 2H). LCMS (Method 7), RT = 10.17 min. Calculated [M + H]$^+$ = 297; Observed [M + H]$^+$ = 297. Yield 27% |
| 141 | [1,3]Bipyrrolidinyl-1-yl-(2-phenylethynyl-thiazol-5-yl)-methanone | LCMS (Method 7), RT = 2.967 min. Calculated [M + H]$^+$ = 352; Observed [M + H]$^+$ = 352. Yield 47% |
| 142 | (3-Azetidin-1-yl-pyrrolidin-1-yl)-(2-phenylethynyl-thiazol-5-yl)-methanone | LCMS (Method 7), RT = 5.443 min. Calculated [M + H]$^+$ = 338; Observed [M + H]$^+$ = 338. Yield 68% |

TABLE 1-continued

| Example | Compound Name | Characterization |
|---|---|---|
| 143 | N-[1-(2-Phenylethynyl-thiazole-5-carbonyl)-pyrrolidin-3-yl]-acetamide | $^1$H NMR (400 MHz, CDCl$^3$) δ 8.19 and 8.15 (2 br s, 1H, rotamers), 7.66-7.56 (m, 2H), 7.49-7.35 (m, 3H), 5.77-5.64 (m, 1H), 4.67-4.53 (m, 1H), 4.16-3.55 (m, 4H), 2.44-2.22 (m, 1H), 2.20-1.88 (m, 1H), 2.03 (s, 3H). LCMS (Method 7), RT = 2.86 min. Calculated [M + H]$^+$ = 340; Observed [M + H]$^+$ = 340. Yield 11% |
| 144 | (Hexahydro-cyclopenta[c]pyrrol-2-yl)-(2-phenylethynyl-thiazol-5-yl)-methanone | $^1$H NMR (400 MHz, DMSO-d$_6$) δ 8.35 (s, 1H), 7.74-7.64 (m, 2H), 7.58-7.45 (m, 3H), 4.07-3.91 (m, 1H), 3.86-3.22 (m, 3H, partially hidden by H$_2$O peak), 2.85-2.71 (m, 1H), 2.71-2.58 (m, 1H), 1.86-1.67 (m, 3H), 1.67-1.39 (m, 3H). LCMS (Method 7), RT = 4.801 min. Calculated [M + H]$^+$ = 323; Observed [M + H]$^+$ = 323. Yield 66% |
| 145 | (7-Aza-bicyclo[2.2.1]hept-7-yl)-(2-phenylethynyl-thiazol-5-yl)-methanone | $^1$H NMR (400 MHz, DMSO-d$_6$) δ 8.39 (s, 1H), 7.74-7.62 (m, 2H), 7.59-7.43 (m, 3H), 4.56 (s, 2H), 1.78 (br s, 4H), 1.62-1.42 (m, 4H). LCMS (Method 7), RT = 4.57 min. Calculated [M + H]$^+$ = 309; Observed [M + H]$^+$ = 309. Yield 41% |
| 146 | (2-Aza-bicyclo[2.2.1]hept-2-yl)-(2-phenylethynyl-thiazol-5-yl)-methanone | $^1$H NMR (400 MHz, DMSO-d$_6$) δ 8.33-8.27 (2 s, 1H, rotamers), 7.74-7.62 (m, 2H), 7.59-7.43 (m, 3H), 4.56 (s, 1H), 3.81-3.71 (m, 0.6 H, major rotamer), 3.49-3.43 (m, 0.6H, major rotamer), 3.43-3.39 (m, 0.4H, minor rotamer), 3.16-3.07 (m, 0.4H, minor rotamer), 2.67 and 2.61 (2 br s, 1H, rotamers), 1.88-1.57 (m, 4H), 1.56-1.38 (m, 2H). LCMS (Method 7), RT = 4.46 min. Calculated [M + H]$^+$ = 309; Observed [M + H]$^+$ = 309. Yield 34% |
| 147 | 1-(2-Phenylethynyl-thiazole-5-carbonyl)-azepan-4-one | $^1$H NMR (400 MHz, DMSO-d$_6$) δ 8.20 (s, 1H), 7.77-7.62 (m, 2H), 7.61-7.42 (m, 3H), 3.98-3.68 (m, 4H), 2.79-2.58 (m, 4H), 1.95-1.71 (m, 2H). LCMS (Method 7), RT = 4.159 min. Calculated [M + H]$^+$ = 325; Observed [M + H]$^+$ = 325. Yield 99% |
| 148 | (4-Morpholin-4-yl-azepan-1-yl)-(2-phenylethynyl-thiazol-5-yl)-methanone | $^1$H NMR (400 MHz, CDCl$_3$) δ 8.02 (s, 1H), 7.68-7.57 (m, 2H), 7.50-7.35 (m, 3H), 3.92-3.78 (m, 2H), 3.71 (br s, 4H), 3.65-3.39 (m, 2H), 2.65-2.43 (m, 5H), 2.15-1.91 (m, 3H), 1.91-1.78 (m, 1H), 1.78-1.66 (m, 1H), 1.66-1.49 (m, 1H). LCMS (Method 7), RT = 2.642 min. Calculated [M + H]$^+$ = 396; Observed [M + H]$^+$ = 396. Yield 29% |

TABLE 1-continued

| Example | Compound | Compound Name | Characterization |
|---|---|---|---|
| 149 | | 1-(2-Phenylethynyl-thiazole-5-carbonyl)-piperidin-4-one | $^1$H NMR (400 MHz, DMSO-d$_6$) δ 8.30 (s, 1H), 7.74-7.65 (m, 2H), 7.58-7.46 (m, 3H), 4.01-3.83 (m, 4H), 2.62-2.37 (m, 4H, partially hidden under solvent peak). LCMS (Method 7), RT = 3.809 min. Calculated [M + H]$^+$ = 311; Observed [M + H]$^+$ = 311. Yield 59% |
| 150 | | (3-Dimethylamino-piperidin-1-yl)-(2-phenylethynyl-thiazol-5-yl)-methanone | $^1$H NMR (400 MHz, CDCl$_3$) δ 7.97 (s, 1H), 7.68-7.56 (m, 2H), 7.51-7.35 (m, 3H), 4.89-3.86 (br m, 2H), 3.31-2.64 (br m, 2H), 2.34 (s, 6H), 2.16-2.03 (m, 1H), 1.96-1.81 (m, 1H), 1.70-1.45 (m, 3H). LCMS (Method 7), RT = 2.626 min. Calculated [M + H]$^+$ = 340; Observed [M + H]$^+$ = 340. Yield 20% |
| 151 | | (4-Hydroxy-4-methyl-azepan-1-yl)-(2-phenylethynyl-thiazol-5-yl)-methanone | $^1$H NMR (400 MHz, CDCl$_3$) δ 8.02 (s, 1H), 7.66-7.56 (m, 2H), 7.48-7.35 (m, 3H), 4.06-3.88 (m, 1H), 3.88-3.56 (m 3H), 3.56-3.34 (m, 1H), 2.39-0.72 (m, 6H), 1.33 (s, 3H). LCMS (Method 7), RT = 3.205 min. Calculated [M + H]$^+$ = 341; Observed [M + H]$^+$ = 341. Yield 8% |
| 152 | | (4-Methoxy-azepan-1-yl)-(2-phenylethynyl-thiazol-5-yl)-methanone | $^1$H NMR (400 MHz, CDCl$_3$) δ 8.01 (s, 1H), 7.66-7.57 (m, 2H), 7.48-7.36 (m, 3H), 3.88-3.44 (m, 5H), 3.35 (s, 3H), 2.16-1.86 (m, 4H), 1.86-1.65 (m, 2H). LCMS (Method 7), RT = 3.64 min. Calculated [M + H]$^+$ = 341; Observed [M + H]$^+$ = 341. Yield 45% |
| 153 | | (2,5-Dimethyl-pyrrolidin-1-yl)-(2-phenylethynyl-thiazol-5-yl)-methanone | $^1$H NMR (300 MHz, CDCl$_3$) δ 8.17 (s, 1H, minor isomer), 8.13 (s, 1H, major isomer), 7.66-7.57 (m, 2H), 7.48-7.35 (m, 3H), 4.55-4.40 (m, 2H, minor isomer), 4.40-4.25 (m, 2H, major isomer), 2.45-1.97 (m, 2H), 1.88-1.55 (m, 2H), 1.39 (d, J = 6.4 Hz, 3H, major isomer), 1.28 (d, J = 6.7 Hz, 3H, minor isomer), 1.13 (d, J = 5.8 Hz, 3H, minor isomer). LCMS (Method 3), RT = 1.52 min. Calculated [M + H]$^+$ = 311; Observed [M + H]$^+$ = 311. Yield >99% |
| 154 | | (2-Methyl-piperidin-1-yl)-(2-phenylethynyl-thiazol-5-yl)-methanone | $^1$H NMR (300 MHz, CDCl$_3$) δ 7.93 (s, 1H), 7.67-7.57 (m, 2H), 7.49-7.35 (m, 3H), 4.83-4.53 (br m, 1H), 4.39-4.09 (br m, 1H), 3.23-3.00 (m, 1H), 1.87-1.42 (m, 6H), 1.32 (d, J = 7.0 Hz, 3H). LCMS (Method 3), RT = 1.51 min. Calculated [M + H]$^+$ = 311; Observed [M + H]$^+$ = 311. Yield 94% |
| 155 | | (2,6-Dimethyl-piperidin-1-yl)-(2-phenylethynyl-thiazol-5-yl)-methanone | $^1$H NMR (300 MHz, CDCl$_3$) δ 7.95 (s, 1H), 7.65-7.56 (m, 2H), 7.47-7.35 (m, 3H), 4.99-4.26 (br m, 2H), 2.01-1.50 (m, 6H), 1.37 (d, J = 7.2 Hz, 6H). LCMS (Method 3), RT = 1.60 min. Calculated [M + H]$^+$ = 325; Observed [M + H]$^+$ = 325. Yield 32% |

TABLE 1-continued

| Example | Compound Name | Characterization |
|---|---|---|
| 156 | (2-Methyl-pyrrolidin-1-yl)-(2-phenylethynyl-thiazol-5-yl)-methanone | $^1$H NMR (300 MHz, CDCl$_3$) δ 8.15 (s, 1H), 7.66-7.57 (m, 2H), 7.48-7.34 (m, 3H), 4.46-4.33 (m, 1H), 3.87-3.67 (m, 3H), 2.23-1.89 (m, 3H), 1.86-1.58 (m, 1H), 1.34 (d, J = 5.8 Hz, 3H). LCMS (Method 3), RT = 1.42 min. Calculated [M + H]$^+$ = 297; Observed [M + H]$^+$ = 297. Yield 52% |
| 157 | [2-(3-Chloro-phenylethynyl)-thiazol-5-yl]-[4-(2-methoxy-ethyl)-piperazin-1-yl]-methanone | $^1$H NMR (300 MHz, CDCl$_3$) δ 7.96 (s, 1H), 7.62-7.58 (m, 1H), 7.52-7.46 (m, 1H), 7.45-7.39 (m, 1H), 7.38-7.30 (m, 1H), 3.90-3.69 (m, 4H), 3.60-3.49 (m, 2H), 3.38 (s, 3H), 2.74-2.49 (m, 6H). LCMS (Method 3), RT = 1.34 min. Calculated [M + H]$^+$ = 390; Observed [M + H]$^+$ = 390. Yield 78% |
| 158 | [2-(3-Chloro-phenylethynyl)-thiazol-5-yl]-(4-methyl-piperazin-1-yl)-methanone | $^1$H NMR (300 MHz, CDCl$_3$) δ 7.97 (s, 1H), 7.63-7.58 (m, 1H), 7.53-7.46 (m, 1H), 7.45-7.39 (m, 1H), 7.39-7.30 (m, 1H), 3.85-3.69 (m, 4H), 2.57-2.43 (m, 4H), 2.35 (s, 3H). LCMS (Method 3), RT = 1.30 min. Calculated [M + H]$^+$ = 346; Observed [M + H]$^+$ = 346. Yield 74% |
| 159 | [2-(3-Chloro-phenylethynyl)-thiazol-5-yl]-(4-ethyl-piperazin-1-yl)-methanone | $^1$H NMR (300 MHz, CDCl$_3$) δ 7.97 (s, 1H), 7.63-7.58 (m, 1H), 7.53-7.46 (m, 1H), 7.45-7.39 (m, 1H), 7.38-7.30 (m, 1H), 3.87-3.70 (m, 4H), 2.62-2.42 (m, 6H), 1.13 (t, J = 7.2 Hz, 3H). LCMS (Method 3), RT = 1.35 min. Calculated [M + H]$^+$ = 360; Observed [M + H]$^+$ = 360. Yield 76% |
| 160 | [2-(3-Chloro-phenylethynyl)-thiazol-5-yl]-[4-(2-hydroxy-ethyl)-piperazin-1-yl]-methanone | $^1$H NMR (300 MHz, CDCl$_3$) δ 7.97 (s, 1H), 7.62-7.58 (m, 1H), 7.52-7.46 (m, 1H), 7.45-7.39 (m, 1H), 7.38-7.30 (m, 1H), 3.85-3.73 (m, 4H), 3.73-3.63 (m, 2H), 2.68-2.53 (m, 6H), 2.44-1.76 (br s, 1H). LCMS (Method 3), RT = 1.15 min. Calculated [M + H]$^+$ = 376; Observed [M + H]$^+$ = 376. Yield 74% |
| 161 | [2-(3-Chloro-phenylethynyl)-thiazol-5-yl]-(4-hydroxy-4-methyl-piperidin-1-yl)-methanone | $^1$H NMR (300 MHz, CDCl$_3$) δ 7.98 (s, 1H), 7.63-7.58 (m, 1H), 7.53-7.46 (m, 1H), 7.45-7.38 (m, 1H), 7.38-7.30 (m, 1H), 4.63-3.76 (br m, 2H), 3.76-3.07 (br m, 2H), 1.79-1.59 (m, 4H), 1.59-1.43 (br s, 1H), 1.34 (s, 3H). LCMS (Method 3), RT = 1.31 min. Calculated [M + H]$^+$ = 361; Observed [M + H]$^+$ = 361. Yield 63% |

TABLE 1-continued

| Example | Compound Name | Characterization |
|---|---|---|
| 162 | [2-(2-Fluoro-phenylethynyl)-thiazol-5-yl]-pyrrolidin-1-yl-methanone | $^1$H NMR (300 MHz, CDCl$_3$) δ 8.20 (s, 1H), 7.64-7.56 (m, 1H), 7.48-7.38 (m, 1H), 7.23-7.11 (m, 2H), 3.82-3.64 (m, 4H), 2.14-1.91 (m, 4H). LCMS (Method 3), RT = 1.33 min. Calculated [M + H]$^+$ = 301; Observed [M + H]$^+$ = 301. Yield 19% |
| 163 | [2-(2-Chloro-phenylethynyl)-thiazol-5-yl]-pyrrolidin-1-yl-methanone | $^1$H NMR (300 MHz, CDCl$_3$) δ 8.20 (s, 1H), 7.64 (dd, J = 7.6, 1.6 Hz, 1H), 7.50-7.44 (m, 1H), 7.41-7.28 (m, 2H), 3.83-3.64 (m, 4H), 2.14-1.92 (m, 4H). LCMS (Method 3), RT = 1.40 min. Calculated [M + H]$^+$ = 317; Observed [M + H]$^+$ = 317. Yield 13% |
| 164 | [2-(3-Chloro-phenylethynyl)-thiazol-5-yl]-(3,4,6,7-tetrahydro-imidazo[4,5-c]pyridin-5-yl)-methanone | $^1$H NMR (300 MHz, CDCl$_3$) δ 8.07 (s, 1H), 7.66-7.56 (m, 2H), 7.54-7.46 (m, 1H), 7.46-7.39 (m, 1H), 7.39-7.30 (m, 1H), 4.96-4.66 (br s, 2H), 4.13-3.88 (m, 2H), 2.99-2.68 (m, 2H). LCMS (Method 3), RT = 1.17 min. Calculated [M + H]$^+$ = 369; Observed [M + H]$^+$ = 369. Yield 51% |
| 165 | [2-(3-Chloro-phenylethynyl)-thiazol-5-yl]-(1,4,6,7-tetrahydro-pyrazolo[4,3-c]pyridin-5-yl)-methanone | $^1$H NMR (300 MHz, CDCl$_3$) δ 8.06 (s, 1H), 7.64-7.59 (m, 1H), 7.54-7.48 (m, 1H), 7.46-7.40 (m, 1H), 7.39-7.31 (m, 1H), 6.13-5.10 (br m, 2H), 4.87-4.77 (m, 2H), 4.09-3.93 (m, 2H), 3.05-2.85 (m, 2H). LCMS (Method 3), RT = 1.24 min. Calculated [M + H]$^+$ = 369; Observed [M + H]$^+$ = 369. Yield 24% |
| 166 | [2-(4-Chloro-phenylethynyl)-thiazol-5-yl]-pyrrolidin-1-yl-methanone | $^1$H NMR (300 MHz, CDCl$_3$) δ 8.17 (s, 1H), 7.58-7.50 (m, 2H), 7.42-7.35 (m, 2H), 3.81-3.64 (m, 4H), 2.12-1.92 (m, 4H). LCMS (Method 3), RT = 1.44 min. Calculated [M + H]$^+$ = 317; Observed [M + H]$^+$ = 317. Yield 8% |
| 167 | (2-Oxa-6-aza-spiro[3.3]hept-6-yl)-(2-phenylethynyl-thiazol-5-yl)-methanone | $^1$H NMR (300 MHz, CDCl$_3$) δ 8.11 (s, 1H), 7.65-7.58 (m, 2H), 7.49-7.36 (m, 3H), 4.86 (s, 4H), 4.76-4.50 (br s, 2H), 4.50-4.22 (br s, 2H). LCMS (Method 3), RT = 1.23 min. Calculated [M + H]$^+$ = 311; Observed [M + H]$^+$ = 311. Yield 40% |

TABLE 1-continued

| Example | Compound | Compound Name | Characterization |
|---|---|---|---|
| 168 | Chiral | ((S)-2-Methoxymethyl-pyrrolidin-1-yl)-(2-phenylethynyl-thiazol-5-yl)-methanone | $^1$H NMR (300 MHz, CDCl$_3$) δ 8.18 (s, 1H), 7.67-7.58 (m, 2H), 7.49-7.36 (m, 3H), 4.52-4.40 (m, 1H), 3.86-3.70 (m, 2H), 3.69-3.52 (m, 2H), 3.38 (s, 3H), 2.23-1.91 (m, 4H). LCMS (Method 3), RT = 1.48 min. Calculated [M + H]$^+$ = 327; Observed [M + H]$^+$ = 327. Yield 71% |
| 169 | Chiral | ((R)-2-Methoxymethyl-pyrrolidin-1-yl)-(2-phenylethynyl-thiazol-5-yl)-methanone | $^1$H NMR (300 MHz, CDCl$_3$) δ 8.18 (s, 1H), 7.67-7.58 (m, 2H), 7.49-7.36 (m, 3H), 4.52-4.40 (m, 1H), 3.86-3.70 (m, 2H), 3.69-3.52 (m, 2H), 3.38 (s, 3H), 2.23-1.91 (m, 4H). LCMS (Method 3), RT = 1.48 min. Calculated [M + H]$^+$ = 327; Observed [M + H]$^+$ = 327. Yield 85% |
| 170 | | (2-Hydroxymethyl-piperidin-1-yl)-(2-phenylethynyl-thiazol-5-yl)-methanone | $^1$H NMR (300 MHz, CDCl$_3$) δ 8.05 (s, 1H), 7.66-7.58 (m, 2H), 7.48-7.36 (m, 3H), 4.81-4.50 (br m, 1H), 4.39-4.10 (br m, 1H), 4.09-3.97 (m, 1H), 3.74 (dd, J = 11, 5.3 Hz, 1H), 3.33-3.02 (br m, 1H), 2.35-1.94 (br m, 1H), 1.87-1.47 (m, 6H). LCMS (Method 3), RT = 1.32 min. Calculated [M + H]$^+$ = 327; Observed [M + H]$^+$ = 327. Yield 53% |
| 171 | | 5-(2-Phenylethynyl-thiazole-5-carbonyl)-hexahydro-pyrrolo[3,4-c]pyrrole-2-carboxylic acid tert-butyl ester | $^1$H NMR (300 MHz, CDCl$_3$) δ 8.16 (s, 1H), 7.69-7.58 (m, 2H), 7.51-7.36 (m, 3H), 4.12-3.87 (m, 2H), 3.76-3.57 (m, 4H), 3.42-3.25 (m, 2H), 3.16-2.90 (m, 2H), 1.48 (s, 9H). LCMS (Method 3), RT = 1.57 min. Calculated [M + H]$^+$ = 424; Observed [M + H]$^+$ = 424. Yield 60% |
| 172 | Chiral | (2-Phenylethynyl-thiazol-5-yl)-((S)-2-pyrrolidin-1-ylmethyl-pyrrolidin-1-yl)-methanone | $^1$H NMR (300 MHz, CDCl$_3$) δ 8.20 (s, 1H), 7.65-7.57 (m, 2H), 7.48-7.35 (m, 3H), 4.61-4.48 (m, 1H). LCMS (Method 3), RT = 1.09 min. Calculated [M + H]$^+$ = 366; Observed [M + H]$^+$ = 366. Yield 42% |
| 173 | | (Hexahydro-pyrrolo[3,4-c]pyrrol-2-yl)-(2-phenylethynyl-thiazol-5-yl)-methasone | $^1$H NMR (300 MHz, CDCl$_3$) δ 8.10 (s, 1H), 7.63-7.54 (m, 2H), 7.45-7.33 (m, 3H), 4.08-3.87 (m, 2H), 3.67-3.53 (m, 2H), 3.21-3.06 (m, 2H), 3.03-2.72 (m, 4H), 2.20 (s, 1H). LCMS (Method 3), RT = 0.91 min. Calculated [M + H]$^+$ = 324; Observed [M + H]$^+$ = 324. |

TABLE 1-continued

| Example | Compound Name | Characterization |
|---|---|---|
| 174 | 1-[5-(2-Phenylethynyl-thiazole-5-carbonyl)-hexahydro-pyrrolo[3,4-c]pyrrol-2-yl]-ethanone | $^1$H NMR (300 MHz, CDCl$_3$) δ 8.15 (s, 1H), 7.66-7.58 (m, 2H), 7.49-7.36 (m, 3H), 4.17-3.88 (m, 2H), 3.88-3.57 (m, 4H), 3.57-3.35 (m, 2H), 3.26-2.91 (m, 2H), 2.08 (s, 3H). LCMS (Method 3), RT = 1.15 min. Calculated [M + H]$^+$ = 366; Observed [M + H]$^+$ = 366. |
| 175 | (5-Methyl-hexahydro-pyrrolo[3,4-c]pyrrol-2-yl)-(2-phenylethynyl-thiazol-5-yl)-methasone | $^1$H NMR (300 MHz, CDCl$_3$) δ 8.11 (s, 1H), 7.65-7.58 (m, 2H), 7.48-7.36 (m, 3H), 4.03 (dd, J = 12, 8.7 Hz, 2H), 3.65 (dd, J = 12, 3.8 Hz, 2H), 3.13-2.86 (m, 2H), 2.73-2.53 (m, 4H), 2.37 (s, 3H). LCMS (Method 3), RT = 1.01 min. Calculated [M + H]$^+$ = 338; Observed [M + H]$^+$ = 338. |
| 176 | ((S)-3-Hydroxy-pyrrolidin-1-yl)-(2-phenylethynyl-thiazol-5-yl)-methanone | $^1$H NMR (300 MHz, CDCl$_3$) δ 8.21 and 8.16 (2 s, 1H, rotamers), 7.68-7.56 (m, 2H), 7.50-7.34 (m, 3H), 4.72-4.57 (m, 1H), 4.08-3.70 (m, 4H), 2.25-1.93 (m, 3H). LCMS (Method 3), RT = 1.13 min. Calculated [M + H]$^+$ = 299; Observed [M + H]$^+$ = 299. Yield 63% |
| 177 | ((R)-3-Hydroxy-pyrrolidin-1-yl)-(2-phenylethynyl-thiazol-5-yl)-methanone | $^1$H NMR (300 MHz, CDCl$_3$) δ 8.21 and 8.16 (2 s, 1H, rotamers), 7.68-7.56 (m, 2H), 7.50-7.34 (m, 3H), 4.72-4.57 (m, 1H), 4.08-3.70 (m, 4H), 2.25-1.93 (m, 3H). LCMS (Method 3), RT = 1.13 min. Calculated [M + H]$^+$ = 299; Observed [M + H]$^+$ = 299. Yield 15% |
| 178 | (4-Bromo-2-phenylethynyl-thiazol-5-yl)-piperidin-1-yl-methanone | $^1$H NMR (400 MHz, CDCl$_3$) δ 7.63-7.59 (m, 2H), 7.48-7.39 (m, 3H), 3.74 (br., s, 2H), 3.46 (br., s, 2H) and 1.76-1.53 (br., m, 6H). LCMS (Method 2), RT = 1.18 min. Calculated [M + H]$^+$ = 374; Observed [M + H]$^+$ = 375.8. Yield 20% |
| 179 | [2-(2,6-Difluoro-phenylethynyl)-thiazol-5-yl]-piperidin-1-yl-methanone | $^1$H NMR (400 MHz, CDCl$_3$) δ 7.96 (s, 1H), 7.37 (quintet, J = 7.3 Hz, 1H), 6.96 (t, J = 7.5 Hz, 2H), 3.66 (br s, 4H), 1.74-1.62 (br m, 6H). RT = 10.79 Min; Calculated [M + H]$^+$ = 333; Observed [M + H]$^+$ = 333. Yield 16% |

TABLE 1-continued

| Example | Compound Name | Characterization |
|---|---|---|
| 180 | [2-(3,5-Difluoro-phenylethynyl)-thiazol-5-yl]-piperidin-1-yl-methanone | $^1$H NMR (400 MHz, CDCl$_3$) δ 7.94 (s, 1H), 7.14-7.09 (m, 2H), 6.89 (t, J = 8.6 Hz, 1H), 3.65 (br s, 4H), 1.75-1.62 (br m, 6H). RT = 4.62 Min; Calculated [M + H]$^+$ = 333; Observed [M + H]$^+$ = 333. Yield 24% |
| 181 | [2-(2-Hydroxy-phenylethynyl)-thiazol-5-yl]-piperidin-1-yl-methanone | $^1$H NMR (400 MHz, CDCl$_3$) δ 7.90 (s, 1H), 7.47 (d, J = 4.3 Hz, 2H), 6.84 (d, J = 4.3 Hz, 2H), 5.78 (br s, 1H), 3.66 (br s, 4H), 1.74-1.61 (br m, 6H). RT = 3.86 Min; Calculated [M + H]$^+$ = 313; Observed [M + H]$^+$ = 313. Yield 39% |
| 182 | [2-(4-Hydroxy-phenylethynyl)-thiazol-5-yl]-piperidin-1-yl-methanone | $^1$H NMR (400 MHz, CDCl$_3$) δ 7.86 (d, J = 4.2 Hz, 1H), 7.40 (s, 1H), 7.36 (t, J = 7.6 Hz, 1H), 7.08 (d, J = 4.2 Hz, 1H), 7.01 (t, J = 7.6 Hz, 2H), 3.69 (br s, 1H), 3.48 (br s, 4H), 1.69-1.58 (br m, 6H). RT = 3.29 Min; Calculated [M + H]$^+$ = 313; Observed [M + H]$^+$ = 313. Yield 66% |
| 183 | [2-(3-Hydroxy-phenylethynyl)-thiazol-5-yl]-piperidin-1-yl-methanone | $^1$H NMR (400 MHz, CDCl$_3$) δ 7.93 (s, 1H), 7.22 (d, J = 4.2 Hz, 1H), 7.13 (d, J = 4.2 Hz, 1H), 7.09 (s, 1H), 6.91 (d, J = 4.3 Hz, 1H), 6.56 (br s, 1H), 3.66 (br s, 4H), 1.74-1.61 (br m, 6H). RT = 3.91 Min; Calculated [M + H]$^+$ = 313; Observed [M + H]$^+$ = 313. Yield 47% |
| 184 | 2-(2,4-Difluoro-phenylethynyl)-thiazol-5-yl]-piperidin-1-yl-methanone | $^1$H NMR (400 MHz, CDCl$_3$) δ 7.94 (s, 1H), 7.59-7.54 (m, 2H), 6.94-6.87 (m, 1H), 3.65 (br s, 4H), 1.73-1.60 (br m, 6H). RT = 4.59 Min; Calculated [M + H]$^+$ = 333; Observed [M + H]$^+$ = 333. Yield 7% |
| 185 | (2-Cyclohexylethynyl-thiazol-5-yl)-piperidin-1-yl-methanone | $^1$H NMR (400 MHz, CDCl$_3$) δ 7.84 (s, 1H), 3.75-3.54 (m, 4H), 2.72-2.59 (m, 1H), 1.99-1.46 (m, 13H), 1.45-1.27 (m, 3H). LCMS (Method 3), RT = 1.67 min. Calculated [M + H]$^+$ = 303; Observed [M + H]$^+$ = 303. Yield 82% |
| 186 | [2-(3,3-Dimethyl-but-1-ynyl)-thiazol-5-yl]-piperidin-1-yl-methanone | $^1$H NMR (400 MHz, CDCl$_3$) δ 7.82 (s, 1H), 3.73-3.53 (m, 4H), 1.76-1.54 (m, 6H), 1.33 (s, 9H). LCMS (Method 3), RT = 1.55 min. Calculated [M + H]$^+$ = 277; Observed [M + H]$^+$ = 277. Yield 81% |
| 187 | Piperidin-1-yl-[2-(3-trifluoromethyl-phenylethynyl)-thiazol-5-yl]-methanone | $^1$H NMR (400 MHz, DMSO-d$_6$) δ 8.20 (s, 1H), 8.10 (br s, 1H), 8.04-7.96 (m, 1H), 7.93-7.86 (m, 1H), 7.78-7.69 (m, 1H), 3.68-3.48 (m, 4H), 1.75-1.44 (m, 6H). LCMS (Method 7), RT = 4.086 min. Calculated [M + H]$^+$ = 365; Observed [M + H]$^+$ = 365. |

TABLE 1-continued

| Example | Compound Name | Characterization |
|---|---|---|
| 188 | Piperidin-1-yl-(2-pyridin-3-ylethynyl-thiazol-5-yl)-methanone | $^1$H NMR (400 MHz, DMSO-d$_6$) δ 8.90 (br s, 1H), 8.71 (br s, 1H), 8.20 (s, 1H), 8.17-8.09 (m, 1H), 7.63-7.48 (m, 1H), 3.68-3.48 (m, 4H), 1.71-1.45 (m, 6H). LCMS (Method 7), RT = 3.600 min. Calculated [M + H]$^+$ = 298; Observed [M + H]$^+$ = 298. |
| 189 | [2-(3-Methoxyphenylethynyl)-thiazol-5-yl]-piperidin-1-yl-methanone | $^1$H NMR (400 MHz, DMSO-d$_6$) δ 8.17 (s, 1H), 7.45-7.36 (m, 1H), 7.31-7.21 (m, 2H), 7.15-7.07 (m, 1H), 3.81 (s, 3H), 3.64-3.52 (m, 4H), 1.70-1.48 (m, 6H). LCMS (Method 7), RT = 4.556 min. Calculated [M + H]$^+$ = 327; Observed [M + H]$^+$ = 327. |
| 190 | Piperidin-1-yl-(2-thiophen-3-ylethynyl-thiazol-5-yl)-methanone | $^1$H NMR (400 MHz, DMSO-d$_6$) δ 8.22-8.12 (m, 2H), 7.77-7.69 (m, 1H), 7.43-7.35 (m, 1H), 3.66-3.49 (m, 4H), 1.69-1.46 (m, 6H). LCMS (Method 7), RT = 3.688 min. Calculated [M + H]$^+$ = 303; Observed [M + H]$^+$ = 303. |
| 191 | Piperidin-1-yl-(2-pyridin-2-ylethynyl-thiazol-5-yl)-methanone | $^1$H NMR (400 MHz, DMSO-d$_6$) δ 8.74-8.64 (m, 1H), 8.23 (s, 1H), 7.99-7.90 (m, 1H), 7.86-7.78 (m, 1H), 7.58-7.50 (m, 1H), 3.69-3.48 (m, 4H), 1.71-1.45 (m, 6H). LCMS (Method 7), RT = 3.733 min. Calculated [M + H]$^+$ = 298; Observed [M + H]$^+$ = 298. |
| 192 | [2-(4-Methoxyphenylethynyl)-thiazol-5-yl]-piperidin-1-yl-methasone | $^1$H NMR (400 MHz, DMSO-d$_6$) δ 8.14 (s, 1H), 7.69-7.59 (m, 2H), 7.11-7.01 (m, 2H), 3.82 (s, 3H), 3.64-3.52 (m, 4H), 1.69-1.48 (m, 6H). LCMS (Method 7), RT = 4.508 min. Calculated [M + H]$^+$ = 327; Observed [M + H]$^+$ = 327. |
| 193 | [2-(6-Methyl-pyridin-2-ylethynyl)-thiazol-5-yl]-piperidin-1-yl-methasone | $^1$H NMR (400 MHz, CDCl$_3$) δ 7.96 (s, 1H), 7.68-7.59 (m, 1H), 7.51-7.43 (m, 1H), 7.24-7.16 (m, 1H), 3.79-3.56 (m, 4H), 2.61 (s, 3H), 1.80-1.61 (m, 6H). LCMS (Method 7), RT = 5.8 min. Calculated [M + H]$^+$ = 312; Observed [M + H]$^+$ = 312. |
| 194 | Piperidin-1-yl-(2-pyrimidin-5-ylethynyl-thiazol-5-yl)-methasone | $^1$H NMR (400 MHz, CDCl$_3$) δ 9.24 (s, 1H), 8.95 (s, 2H), 7.99 (s, 1H), 3.80-3.57 (m, 4H), 1.83-1.60 (m, 6H). LCMS (Method 7), RT = 6.618 min. Calculated [M + H]$^+$ = 299; Observed [M + H]$^+$ = 299. |

TABLE 1-continued

| Example | Compound Name | Characterization |
|---|---|---|
| 195 | (2-Ethynyl-thiazol-5-yl)-piperidin-1-yl-methasone | $^1$H NMR (300 MHz, CDCl$_3$) δ 7.91 (s, 1H), 3.73-3.58 (m, 4H), 3.55 (s, 1H), 1.80-1.44 (m, 6H). LCMS (Method 3), RT = 1.07 min. Calculated [M + H]$^+$ = 221; Observed [M + H]$^+$ = 221. |
| 196 | 3-[5-(Piperidine-1-carbonyl)-thiazol-2-ylethynyl]-benzonitrile | $^1$H NMR (400 MHz, CDCl$_3$) δ 7.97 (s, 1H), 7.92-7.87 (m, 1H), 7.86-7.80 (m, 1H), 7.75-7.67 (m, 1H), 7.58-7.50 (m, 1H), 3.78-3.57 (m, 4H), 1.81-1.63 (m, 6H). LCMS (Method 7), RT = 4.21 min. Calculated [M + H]$^+$ = 322; Observed [M + H]$^+$ = 322. |
| 197 | 4-[5-(Piperidine-1-carbonyl)-thiazol-2-ylethynyl]-benzonitrile | $^1$H NMR (400 MHz, CDCl3) δ 7.98 (s, 1H), 7.70 (s, 4H), 3.76-3.61 (m, 4H), 1.80-1.63 (m, 6H). LCMS (Method 7), RT = 4.21 min. Calculated [M + H]$^+$ = 322; Observed [M + H]$^+$ = 322. |
| 198 | (2-Pyridin-2-ylethynyl-thiazol-5-yl)-pyrrolidin-1-yl-methanone | $^1$H NMR (300 MHz, CDCl$_3$) δ 8.78-8.62 (m, 1H), 8.21 (s, 1H), 7.82-7.71 (m, 1H), 7.70-7.59 (m, 1H), 7.41-7.31 (m, 1H), 3.84-3.63 (m, 4H), 2.16-1.90 (m, 4H). LCMS (Method 3), RT = 1.07 min. Calculated [M + H]$^+$ = 284; Observed [M + H]$^+$ = 284. Yield 34% |
| 199 | Morpholin-4-yl-(2-pyridin-2-ylethynyl-thiazol-5-yl)-methanone | $^1$H NMR (300 MHz, CDCl$_3$) δ 8.75-8.64 (m, 1H), 8.00 (s, 1H), 7.81-7.72 (m, 1H), 7.70-7.60 (m, 1H), 7.41-7.32 (m, 1H), 3.77 (s, 8H). LCMS (Method 3), RT = 0.95 min. Calculated [M + H]$^+$ = 300; Observed [M + H]$^+$ = 300. Yield 31% |
| 200 | (2-Cyclohexylethynyl-thiazol-5-yl)-piperidin-1-yl-methanone | $^1$H NMR (400 MHz, CDCl$_3$) δ 7.84 (s, 1H), 3.75-3.54 (m, 4H), 2.72-2.59 (m, 1H), 1.99-1.46 (m, 13H), 1.45-1.27 (m, 3H). LCMS (Method 3), RT = 1.67 min. Calculated [M + H]$^+$ = 303; Observed [M + H]$^+$ = 303. Yield 82% |

TABLE 1-continued

| Example | Compound | Compound Name | Characterization |
|---|---|---|---|
| 201 | | [2-(3,3-Dimethyl-but-1-ynyl)-thiazol-5-yl]-piperidin-1-yl-methanone | $^1$H NMR (400 MHz, CDCl$_3$) δ 7.82 (s, 1H), 3.73-3.53 (m, 4H), 1.76-1.54 (m, 6H), 1.33 (s, 9H). LCMS (Method 3), RT = 1.55 min. Calculated [M + H]$^+$ = 277; Observed [M + H]$^+$ = 277. Yield 81% |
| 202 | | Piperidin-1-yl-[2-(3-trifluoromethyl-phenylethynyl)-thiazol-5-yl]-methanone | $^1$H NMR (400 MHz, DMSO-d$_6$) δ 8.20 (s, 1H), 8.10 (br s, 1H), 8.04-7.96 (m, 1H), 7.93-7.86 (m, 1H), 7.78-7.69 (m, 1H), 3.68-3.48 (m, 4H), 1.75-1.44 (m, 6H). LCMS (Method 7), RT = 4.086 min. Calculated [M + H]$^+$ = 365; Observed [M + H]$^+$ = 365. |
| 203 | | Piperidin-1-yl-(2-pyridin-3-ylethynyl-thiazol-5-yl)-methanone | $^1$H NMR (400 MHz, DMSO-d$_6$) δ 8.90 (br s, 1H), 8.71 (br s, 1H), 8.20 (s, 1H), 8.17-8.09 (m, 1H), 7.63-7.48 (m, 1H), 3.68-3.48 (m, 4H), 1.71-1.45 (m, 6H). LCMS (Method 7), RT = 3.600 min. Calculated [M + H]$^+$ = 298; Observed [M + H]$^+$ = 298. |
| 204 | | [2-(2-Methoxy-phenylethynyl)-thiazol-5-yl]-piperidin-1-yl-methanone | $^1$H NMR (400 MHz, DMSO-d$_6$) δ 7.90 (s, 1H), 7.53 (D, J = 8.3 Hz, 2H), 6.90 (d, J = 8.4 Hz, 2H), 3.66 (br., s, 4H), 1.72-1.56 (m, 6H). LCMS (Method 7), RT = 4.22 min. Calculated [M + H]$^+$ = 327; Observed [M + H]$^+$ = 327. |

Example 205

2-Phenylethynyl-thiazole-5-carbaldehyde

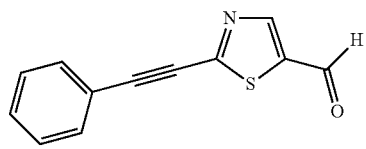 [SMILES: O=Cc1cnc(C#Cc2ccccc2)s1]

Example 205 was prepared via the Scheme 3, step a, using standard Sonogashira coupling between 2-Bromo-5-formylthiazole (49) and phenylacetylene, as follows:

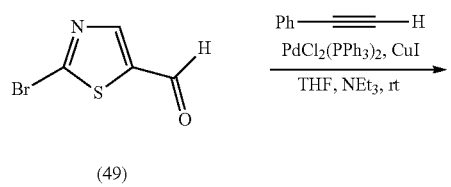

-continued

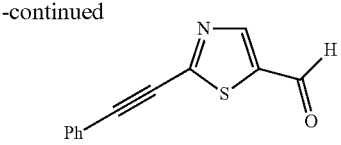

Example-205

To a round bottom flask was added 2-bromo-5-formylthiazole (3.83 g, 19.9 mmol, purchased from Frontier Scientific, Inc.), THF (100 mL) and triethylamine (20 mL). To the solution was successively added CuI (228 mg, 1.20 mmol), PdCl$_2$(PPh$_3$)$_2$ (420 mg, 0.60 mmol) and a solution of phenylacetylene (2.24 g, 21.9 mmol) in THF (20 mL) over a period of about 5 minutes. The reaction was then stirred at room temperature for 18 hours. The volatiles were removed under reduced pressure, the residue transferred to a 1.0-L separatory funnel with EtOAc (200 mL) and saturated aqueous sodium bicarbonate (300 mL) and extracted. The layers were separated and the aqueous layer was extracted again with EtOAc (2×100 mL). The combined organic layers were then washed with brine, dried over sodium sulfate, filtered and concentrated under reduced pressure. The residue was purified by silica gel chromatography, eluting with a gradient ranging from 5% to 50% EtOAc in hexanes to afford the titled compound, 2-phenylethynyl-thiazole-5-carbaldehyde, (3.94 g, 93%) as an orange solid.

Synthesis of Compounds of Invention Type Ib

The compounds of type Ib can be synthesized via reductive amination of aldehyde (Example—205) with amines using sodium triacetoxyborohydride as described in Scheme 3, step b, when $R^5$ is H. The compounds of type Ib can also be synthesized in a two step process involving the formation of a Katrizky aminal intermediate formed from aldehyde (Example—205), amines and benzotriazole in THF-EtOH followed by addition of a Grignard reagent (Scheme 3, step b, when $R^5$ is not H but as previously defined). Both syntheses are illustrated as follows

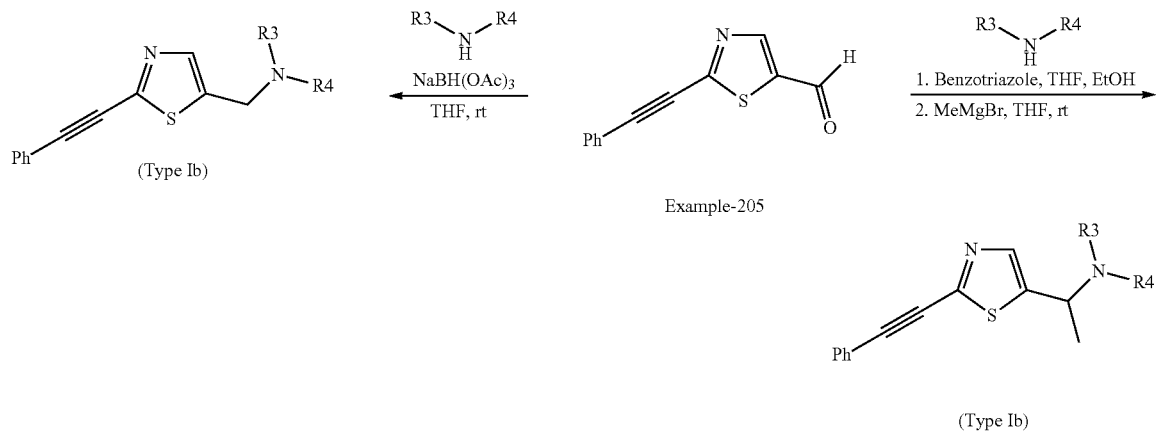

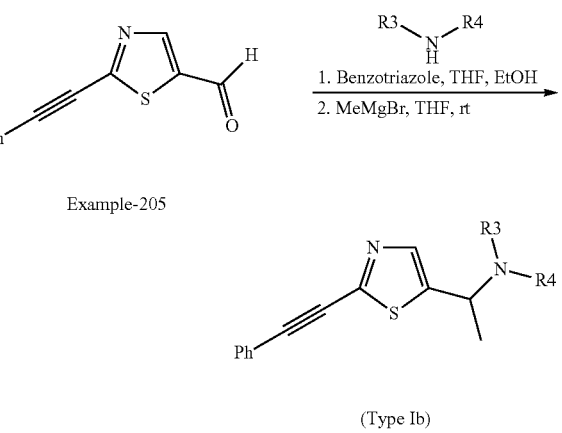

Alternatively, the compounds of type Ib may be synthesized in a two step process involving Grignard addition to aldehyde (Example 205) followed by oxidation with pyridinium dichromate to afford ketones of type Id. (See Scheme 3, steps a, c and d.) Further reductive amination of the ketones of type Id with amines using either sodium triacetoxyborohydride or Ti(OiPr)$_4$/NaBH$_4$ affords amines of type Ib. (See Scheme 3, step b following steps a, c and d.)

Example 206

1-(2-Phenylethynyl-thiazol-5-ylmethyl)-piperidine

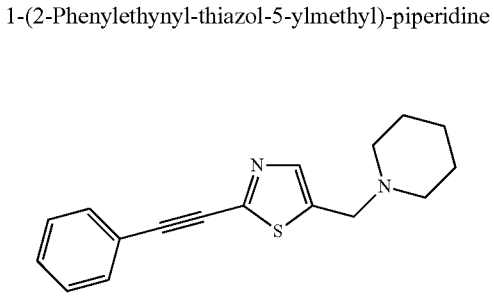

Example 206 was prepared via Scheme 3, steps b, from Example 205, as follows:

In a culture tube was added 2-phenylethynyl-thiazole-5-carbaldehyde (Example 205, 50 mg, 0.23 mmol), piperidine (24 mg, 0.28 mmol) and THF (2.0 mL). The mixture was stirred at room temperature for 1 hour then treated with sodium triacetoxyborohydride (75 mg, 0.35 mmol) and stirred at room temperature for about 4 hours. The crude reaction mixture was transferred to a 20-mL vial with saturated aqueous sodium bicarbonate (about 5 mL) and EtOAc (about 5 mL) and stirred vigorously for a few seconds. The layers were then separated and the aqueous layer was stirred again with EtOAc (about 5 mL). The combined organic layers were washed with brine (about 10 mL), dried over sodium sulfate, filtered and concentrated under reduced pressure. The residue was then purified by preparative TLC, eluting with 50% EtOAc in hexanes to afford 32 mg (48%) of the titled compound, 1-(2-Phenylethynyl-thiazol-5-ylmethyl)-piperidine, as an orange solid.

Examples 207-230 were prepared in a similar fashion as Example 206, but with the appropriate intermediate. In some embodiments, dichloromethane was used as a solvent instead of THF. In addition, a slight excess of either triethylamine or diisopropylethylamine was added to the reaction mixture when the hydrochloride or trifluoroacetate salt of the amine was used.

Example 233

2-Phenylethynyl-5-(1-pyrrolidin-1-yl-ethyl)-thiazole

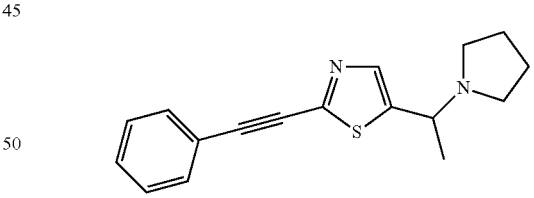

Example 233 was prepared via Scheme 3, steps b, from Example 205, as follows:

In a culture tube was added pyrrolidine (17.8 mg, 0.250 mmol) and benzotriazole (29.8 mg, 0.250 mmol) in ethanol (1.0 mL). After stirring at room temperature for 10 minutes, the solution was treated with 2-phenylethynyl-thiazole-5-carbaldehyde (Example 205, 53.3 mg, 0.250 mmol) and THF (0.5 to 1.0 mL) and stirred at room temperature for 1 hour. The volatiles were then removed under reduced pressure, the residue dissolved in ethanol (1.0 mL) and THF (1.0 mL) and the volatiles removed again under reduced pressure. The residue was dissolved once more in THF (1.0 mL), concentrated under reduced pressure and kept under high vacuum for about 1 hour. The residue was then dissolved in THF (1.0 mL) and treated with methyl magnesium bromide (170 μL of a 3.0 M solution in diethyl ether, 0.50 mmol) and the reaction was stirred at room temperature. The reaction was quenched by adding saturated aqueous sodium bicarbonate (4 mL) and diluted with EtOAc (4 mL). After stirring vigorously for a few minutes, the layers were separated and the aqueous layer was stirred again with EtOAc (4 mL). The combined organic layers were washed with brine, dried over sodium sulfate, filtered and concentrated under reduced pressure. The residue was purified on a reversed phase liquid chromatography/mass spectrometry (RP-HPLC/MS) purification system. Gradient: acetonitrile in water, 28-95% in 3.6 minutes with a cycle time of 5 min. A shallow gradient between 38-68% of acetonitrile was used between 0.75-3.3 min to separate close-eluting impurities. Flow rate: 100 mL/min. Mobile phase additive: 96 mM of ammonium formate. Column: Inertsil® C18, 30×50 mm, 5 μm particle size (GL Sciences, Tokyo, Japan)). Fractions were concentrated under reduced pressure and the solid obtained was partitioned between EtOAc (5 mL) and saturated aqueous sodium bicarbonate (5 mL). After stirring vigorously for a few seconds, the layers were separated and the aqueous layer was stirred again with EtOAc (5 mL). The combined organic layers were washed with brine, dried over sodium sulfate, filtered and concentrated under reduced pressure to afford the titled compound, 2-phenylethynyl-5-(1-pyrrolidin-1-yl-ethyl)-thiazole, (26 mg, 37%) as an amber oil.

Examples 231-232 were prepared in a similar fashion as Example 233, but with the appropriate intermediate.

TABLE 2

| Example | Compound | Compound Name | Characterization |
|---|---|---|---|
| 205 | | 2-Phenylethynyl-thiazole-5-carbaldehyde | $^1$H NMR (300 MHz, CDCl$_3$) δ 10.0 (s, 1H), 8.44 (s, 1H), 7.68-7.61 (m, 2H), 7.51-7.38 (m, 3H). LCMS (Method 3), RT = 1.43 min. Calculated [M + H]$^+$ = 214; Observed [M + H]$^+$ = 214. Yield 93% |
| 206 | | 1-(2-Phenylethynyl-thiazol-5-ylmethyl)-piperidine | $^1$H NMR (300 MHz, CDCl$_3$) δ 7.68-7.53 (m, 3H), 7.47-7.32 (m, 3H), 3.73 (s, 2H), 2.56-2.35 (m, 4H), 1.70-1.53 (m, 4H), 1.52-1.38 (m, 2H). LCMS (Method 3), RT = 1.53 min. Calculated [M + H]$^+$ = 283; Observed [M + H]$^+$ = 283. Yield 48% |
| 207 | | 2-Phenylethynyl-5-pyrrolidin-1-ylmethyl-thiazole | $^1$H NMR (300 MHz, CDCl$_3$) δ 7.65 (br s, 1H), 7.63-7.54 (m, 2H), 7.45-7.33 (m, 3H), 3.87 (s, 2H), 2.68-2.50 (m, 4H), 1.90-1.74 (m, 4H). LCMS (Method 3), RT = 1.26 min. Calculated [M + H]$^+$ = 269; Observed [M + H]$^+$ = 269. Yield 52% |
| 208 | | 4-Methyl-1-(2-phenylethynyl-thiazol-5-ylmethyl)-piperidine | $^1$H NMR (300 MHz, CDCl$_3$) δ 7.67-7.54 (m, 3H), 7.46-7.33 (m, 3H), 3.73 (s, 2H), 2.97-2.83 (m, 2H), 2.11-1.95 (m, 2H), 1.70-1.57 (m, 2H), 1.45-1.16 (m, 3H), 0.93 (d, J = 6.0 Hz, 3H). LCMS (Method 3), RT = 1.65 min. Calculated [M + H]$^+$ = 297; Observed [M + H]$^+$ = 297. Yield 49% |
| 209 | | 4-(2-Phenylethynyl-thiazol-5-ylmethyl)-morpholine | $^1$H NMR (400 MHz, CDCl$_3$) δ 7.64 (br s, 1H), 7.61-7.54 (m, 2H), 7.44-7.34 (m, 3H), 3.80-3.65 (m, 6H), 2.58-2.44 (m, 4H). LCMS (Method 3), RT = 1.42 min. Calculated [M + H]$^+$ = 285; Observed [M + H]$^+$ = 285. Yield 43% |
| 210 | | 1-(2-Phenylethynyl-thiazol-5-ylmethyl)-piperidin-4-ol | $^1$H NMR (400 MHz, CDCl$_3$) δ 7.65-7.55 (m, 3H), 7.45-7.32 (m, 3H), 3.78-3.68 (m, 3H), 2.85-2.74 (m, 2H), 2.31-2.18 (m, 2H), 1.98-1.69 (m, 3H), 1.68-1.53 (m, 2H). LCMS (Method 3), RT = 1.19 min. Calculated [M + H]$^+$ = 299; Observed [M + H]$^+$ = 299. Yield 60% |

TABLE 2-continued

| Example | Compound Name | Characterization |
|---|---|---|
| 211 | 1-Methyl-4-(2-phenylethynyl-thiazol-5-ylmethyl)-piperazine | $^1$H NMR (400 MHz, CDCl$_3$) δ 7.63 (s, 1H), 7.60-7.55 (m, 2H), 7.45-7.31 (m, 3H), 3.74 (s, 2H), 2.74-2.33 (br m, 8H), 2.30 (s, 3H). LCMS (Method 3), RT = 1.14 min. Calculated [M + H]$^+$ = 298; Observed [M + H]$^+$ =298. Yield 62% |
| 212 | Dimethyl-(2-phenylethynyl-thiazol-5-ylmethyl)-amine | $^1$H NMR (300 MHz, CDCl$_3$) δ 7.62 (br s, 1H), 7.61-7.54 (m, 2H), 7.45-7.32 (m, 3H), 3.67 (s, 2H), 2.29 (s, 6H). LCMS (Method 3), RT = 1.39 min. Calculated [M + H]$^+$ = 243; Observed [M + H]$^+$ = 243. Yield 73% |
| 213 | Diethyl-(2-phenylethynyl-thiazol-5-ylmethyl)-amine | $^1$H NMR (300 MHz, CDCl$_3$) δ 7.62 (br s, 1H), 7.61-7.54 (m, 2H), 7.44-7.32 (m, 3H), 3.87-3.82 (m, 2H), 2.56 (q, J = 7.2 Hz, 4H), 1.08 (t, J = 7.2 Hz, 6H). LCMS (Method 3), RT = 1.59 min. Calculated [M + H]$^+$ = 271; Observed [M + H]$^+$ = 271. Yield 63% |
| 214 | 5-(3-Methoxy-azetidin-1-ylmethyl)-2-phenylethynyl-thiazole | $^1$H NMR (300 MHz, CDCl$_3$) δ 7.63 (br s, 1H), 7.61-7.55 (m, 2H), 7.43-7.33 (m, 3H), 4.11-4.01 (m, 1H), 3.84 (s, 2H), 3.71-3.60 (m, 2H), 3.26 (s, 3H), 3.05-2.94 (m, 2H). LCMS (Method 3), RT = 1.39 min. Calculated [M + H]$^+$ = 285; Observed [M + H]$^+$ = 285. Yield 53% |
| 215 | 5-Azetidin-1-ylmethyl-2-phenylethynyl-thiazole | $^1$H NMR (300 MHz, CDCl$_3$) 7.66-7.52 (m, 3H), 7.44-7.32 (m, 3H), 3.79-3.74 (m, 2H), 3.26 (t, J = 7.0 Hz, 4H), 2.16-2.05 (m, 2H). LCMS (Method 3), RT = 1.24 min. Calculated [M + H]$^+$ = 255; Observed [M + H]$^+$ = 255. Yield 55% |
| 216 | Chiral 5-((S)-2-Methoxymethyl-pyrrolidin-1-ylmethyl)-2-phenylethynyl-thiazole | $^1$H NMR (300 MHz, CDCl$_3$) δ 7.64 (s, 1H), 7.61-7.54 (m, 2H), 7.43-7.33 (m, 3H), 4.27 (dd, J = 14.5, 0.9 Hz, 1H), 3.88 (d, J = 14.5 Hz, 1H), 3.48-3.32 (m, 2H), 3.37 (s, 3H), 3.10-2.99 (m, 1H), 2.87-2.74 (m, 1H), 2.42-2.29 (m, 1H), 1.99-1.51 (m, 4H). LCMS (Method 3), RT = 1.63 min. Calculated [M + H]$^+$ = 313; Observed [M + H]$^+$ = 313. Yield 72% |
| 217 | Chiral 5-((R)-2-Methoxymethyl-pyrrolidin-1-ylmethyl)-2-phenylethynyl-thiazole | $^1$H NMR (300 MHz, CDCl$_3$) δ 7.64 (s, 1H), 7.61-7.54 (m, 2H), 7.43-7.33 (m, 3H), 4.27 (dd, J = 14.5, 0.9 Hz, 1H), 3.88 (d, J = 14.5 Hz, 1H), 3.48-3.32 (m, 2H), 3.37 (s, 3H), 3.10-2.99 (m, 1H), 2.87-2.74 (m, 1H), 2.42-2.29 (m, 1H), 1.99-1.51 (m, 4H). LCMS (Method 3), RT = 1.62 min. Calculated [M + H]$^+$ = 313; Observed [M + H]$^+$ = 313. Yield 82% |

TABLE 2-continued

| Example | Compound | Compound Name | Characterization |
| --- | --- | --- | --- |
| 218 | | 2-(2-Phenylethynyl-thiazol-5-ylmethyl)-2-aza-bicyclo[2.2.1]heptane | $^1$H NMR (300 MHz, CDCl$_3$) δ 7.67-7.52 (m, 3H), 7.45-7.32 (m, 3H), 3.92-3.74 (m, 2H), 3.26 (s, 1H), 2.81-2.72 (m, 1H), 2.41-2.26 (m, 2H), 1.81-1.39 (m, 4H), 1.39-1.20 (m, 2H). LCMS (Method 3), RT = 1.57 min. Calculated [M + H]$^+$ = 291; Observed [M + H]$^+$ = 291. Yield 52% |
| 219 | | 5-(3,3-Difluoro-azetidin-1-ylmethyl)-2-phenylethynyl-thiazole | $^1$H NMR (300 MHz, CDCl$_3$) δ 7.65 (s, 1H), 7.62-7.55 (m, 2H), 7.44-7.34 (m, 3H), 3.96-3.92 (m, 2H), 3.65 (t, J = 12.0 Hz, 4H). LCMS (Method 3), RT = 1.57 min. Calculated [M + H]$^+$ = 291; Observed [M + H]$^+$ = 291. Yield 61% |
| 220 | | 5-(3,3-Difluoro-pyrrolidin-1-ylmethyl)-2-phenylethynyl-thiazole | $^1$H NMR (300 MHz, CDCl$_3$) δ 7.66 (s, 1H), 7.63-7.56 (m, 2H), 7.45-7.35 (m, 3H), 3.90 (s, 2H), 2.98 (br t, J = 13.1 Hz, 2H), 2.89-2.77 (m, 2H), 2.41-2.23 (m, 2H). LCMS (Method 3), RT = 1.63 min. Calculated [M + H]$^+$ = 305; Observed [M + H]$^+$ = 305. Yield 60% |
| 221 | | 2-Methyl-1-(2-phenylethynyl-thiazol-5-ylmethyl)-piperidine | $^1$H NMR (300 MHz, CDCl$_3$) δ 7.65-7.54 (m, 3H), 7.44-7.33 (m, 3H), 4.04 (d, J = 15.0 Hz, 1H), 3.84 (d, J = 15.0 Hz, 1H), 2.87-2.75 (m, 1H), 2.43-2.27 (m, 1H), 2.17 (td, J = 10.8, 3.2 Hz, 1H), 1.75-1.44 (m, 4H), 1.42-1.22 (m, 2H), 1.17 (d, J = 6.2 Hz, 3H). LCMS (Method 3), RT = 1.72 min. Calculated [M + H]$^+$ = 297; Observed [M + H]$^+$ = 297. Yield 42% |
| 222 | | 3,3-Difluoro-1-(2-phenylethynyl-thiazol-5-ylmethyl)-piperidine | $^1$H NMR (300 MHz, CDCl$_3$) δ 7.64 (br s, 1H), 7.62-7.55 (m, 2H), 7.45-7.34 (m, 3H), 3.86 (s, 2H), 2.71 (t, J = 11.1 Hz, 2H), 2.58-2.48 (m, 2H), 1.99-1.73 (m, 4H). LCMS (Method 3), RT = 1.67 min. Calculated [M + H]$^+$ = 319; Observed [M + H]$^+$ = 319. Yield 25% |
| 223 | | 4,4-Difluoro-1-(2-phenylethynyl-thiazol-5-ylmethyl)-piperidine | $^1$H NMR (300 MHz, CDCl$_3$) δ 7.64 (br s, 1H), 7.62-7.55 (m, 2H), 7.45-7.34 (m, 3H), 3.80 (s, 2H), 2.75-2.50 (m, 4H), 2.15-1.89 (m, 4H). LCMS (Method 3), RT = 1.67 min. Calculated [M + H]$^+$ = 319; Observed [M + H]$^+$ = 319. Yield 40% |
| 224 | | 5-(3-Fluoro-azetidin-1-ylmethyl)-2-phenylethynyl-thiazole | $^1$H NMR (300 MHz, CDCl$_3$) δ 7.64 (br s, 1H), 7.62-7.55 (m, 2H), 7.45-7.34 (m, 3H), 5.15 (d of multiplet, J = 57 Hz, 1H), 3.88 (s, 2H), 3.78-3.64 (m, 2H), 3.32-3.15 (m, 2H). LCMS (Method 3), RT = 1.46 min. Calculated [M + H]$^+$ = 273; Observed [M + H]$^+$ = 273. Yield 34% |

TABLE 2-continued

| Example | Compound | Compound Name | Characterization |
| --- | --- | --- | --- |
| 225 | | 3-Fluoro-1-(2-phenylethynyl-thiazol-5-ylmethyl)-piperidine | $^1$H NMR (300 MHz, CDCl$_3$) δ 7.63 (br s, 1H), 7.61-7.55 (m, 2H), 7.45-7.34 (m, 3H), 4.65 (d of multiplet, J = 48 Hz, 1H), 3.81 (s, 2H), 2.91-2.73 (m, 1H), 2.61-2.42 (m, 2H), 2.42-2.27 (m, 1H), 1.98-1.76 (m, 2H), 1.73-1.47 (m, 2H). LCMS (Method 3), RT = 1.63 min. Calculated [M + H]$^+$ = 301; Observed [M + H]$^+$ = 301. Yield 47% |
| 226 | | 4-Fluoro-1-(2-phenylethynyl-thiazol-5-ylmethyl)-piperidine | $^1$H NMR (300 MHz, CDCl$_3$) δ 7.63 (br s, 1H), 7.62-7.55 (m, 2H), 7.44-7.34 (m, 3H), 4.70 (d of multiplet, J = 49 Hz, 1H), 3.75 (s, 2H), 2.71-2.54 (m, 2H), 2.54-2.37 (m, 2H), 2.03-1.78 (m, 4H). LCMS (Method 3), RT = 1.61 min. Calculated [M + H]$^+$ = 301; Observed [M + H]$^+$ = 301. Yield 40% |
| 227 | | 5-(2-Methyl-pyrrolidin-1-ylmethyl)-2-phenylethynyl-thiazole | $^1$H NMR (300 MHz, CDCl$_3$) δ 7.63 (br s, 1H), 7.61-7.53 (m, 2H), 7.43-7.33 (m, 3H), 4.12 (dd, J = 14.3, 1.1 Hz, 1H), 3.60 (d, J = 14.4 Hz, 1H), 3.08-2.95 (m, 1H), 2.53-2.38 (m, 1H), 2.29-2.16 (m, 1H), 2.02-1.86 (m, 1H), 1.85-1.58 (m, 2H), 1.54-1.38 (m, 1H), 1.15 (d, J = 6.0 Hz, 3H). LCMS (Method 3), RT = 1.55 min. Calculated [M + H]$^+$ = 283; Observed [M + H]$^+$ = 283. Yield 51% |
| 228 | | 5-(2,2-Dimethyl-pyrrolidin-1-ylmethyl)-2-phenylethynyl-thiazole | $^1$H NMR (300 MHz, CDCl$_3$) δ 6 7.62 (br s, 1H), 7.61-7.53 (m, 2H), 7.43-7.33 (m, 3H), 3.75 (s, 2H), 2.77-2.67 (m, 2H), 1.81-1.63 (m, 4H), 1.08 (s, 6H). LCMS (Method 3), RT = 1.70 min. Calculated [M + H]$^+$ = 297; Observed [M + H]$^+$ = 297. Yield 38% |
| 229 | | Chiral 5-((S)-3-Fluoro-pyrrolidin-1-ylmethyl)-2-phenylethynyl-thiazole | $^1$H NMR (300 MHz, CDCl$_3$) δ 7.65 (br s, 1H), 7.63-7.54 (m, 2H), 7.44-7.33 (m, 3H), 5.18 (d of multiplet, J = 55 Hz, 1H), 3.91 (s, 2H), 3.00-2.73 (m, 3H), 2.63-2.49 (m, 1H), 2.29-1.97 (m, 2H). LCMS (Method 3), RT = 1.51 min. Calculated [M + H]$^+$ = 287; Observed [M + H]$^+$ = 287. Yield 35% |
| 230 | | Chiral 5-((R)-3-Fluoro-pyrrolidin-1-ylmethyl)-2-phenylethynyl-thiazole | $^1$H NMR (300 MHz, CDCl$_3$) δ 7.65 (br s, 1H), 7.63-7.54 (m, 2H), 7.44-7.33 (m, 3H), 5.18 (d of multiplet, J = 55 Hz, 1H), 3.91 (s, 2H), 3.00-2.73 (m, 3H), 2.63-2.49 (m, 1H), 2.29-1.97 (m, 2H). LCMS (Method 3), RT = 1.51 min. Calculated [M + H]$^+$ = 287; Observed [M + H]$^+$ =287. Yield 38% |
| 231 | | 1-[1-(2-Phenylethynyl-thiazol-5-yl)-ethyl]-piperidine | $^1$H NMR (300 MHz, CDCl$_3$) δ 7.63-7.52 (m, 3H), 7.44-7.32 (m, 3H), 3.96 (q, J = 6.7 Hz, 1H), 2.53-2.37 (m, 4H), 1.66-1.52 (m, 4H), 1.48-1.37 (m, 2H), 1.44 (d, J = 6.7 Hz, 3H). LCMS (Method 3), RT = 1.77 min. Calculated [M + H]$^+$ = 297; Observed [M + H]$^+$ = 297. Yield 46% |

TABLE 2-continued

| Example | Compound | Compound Name | Characterization |
|---|---|---|---|
| 232 | | 4-[1-(2-Phenylethynyl-thiazol-5-yl)-ethyl]-morpholine | $^1$H NMR (300 MHz, CDCl$_3$) δ 7.64-7.53 (m, 3H), 7.45-7.33 (m, 3H), 3.90 (q, J = 6.7 Hz, 1H), 3.78-3.65 (m, 4H), 2.62-2.44 (m, 4H), 1.46 (d, J = 6.7 Hz, 3H). LCMS (Method 3), RT = 1.54 min. Calculated [M + H]$^+$ = 299; Observed [M + H]$^+$ = 299. Yield 44% |
| 233 | | 2-Phenylethynyl-5-(1-pyrrolidin-1-yl-ethyl)-thiazole | $^1$H NMR (300 MHz, CDCl$_3$) δ 7.65-7.54 (m, 3H), 7.45-7.33 (m, 3H), 3.76 (q, J = 6.7 Hz, 1H), 2.70-2.42 (m, 4H), 1.88-1.68 (m, 4H), 1.50 (d, J = 6.7 Hz, 3H). LCMS (Method 3), RT = 1.51 min. Calculated [M + H]$^+$ = 283; Observed [M + H]$^+$ = 283. Yield 37% |

Synthesis of Compounds of Invention Types Ic, Id and Ie

Alcohols (Ic) and (Ie) and ketones (Id) were prepared via the processes outlined in Scheme 3. Treatment of Example 205 with Grignard reagents provided alcohols (Ic), which were oxidized with pyridinium dichromate to afford ketones (Id). Addition of a Grignard reagent to the ketones (Id) provided tertiary alcohols (Ie); and Examples 234-241 of Table 3 were prepared accordingly:

ring for about 30 minutes at 0° C., the reaction was quenched with saturated aqueous ammonium chloride (25 mL), diluted with EtOAc (25 mL), transferred to a 125-mL separatory funnel and extracted. The layers were separated and the aqueous layer was extracted again with EtOAc (25 mL). The combined organic layers were then washed with brine, dried over sodium sulfate, filtered and concentrated under reduced pressure. The residue was purified by preparative TLC, eluting with 25% EtOAc in hexanes to afford the titled com-

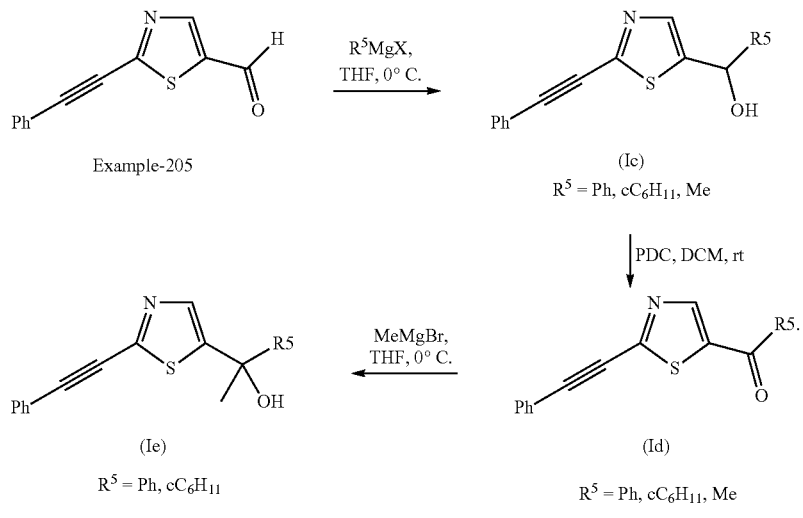

Example 234

Phenyl-(2-phenylethynyl-thiazol-5-yl)-methanol

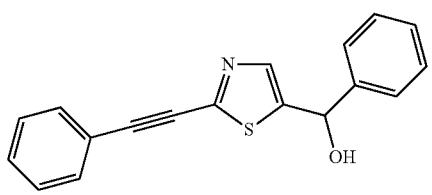 [SMILES: OC(c1ccccc1)c1cnc(C#Cc2ccccc2)s1]

Example 234 was prepared via Scheme 3, step c, from Example 205, as follows:

A solution of 2-phenylethynyl-thiazole-5-carbaldehyde (Example 205, 197 mg, 0.924 mmol) in THF (5.0 mL) was cooled at 0° C. and treated with a 3.0 M solution of phenyl magnesium bromide in Ether (340 μL, 1.0 mmol). After stirpound, pPhenyl-(2-phenylethynyl-thiazol-5-yl)-methanol (190 mg, 71%), as a pale yellow oil.

Example 235

Cyclohexyl-(2-phenylethynyl-thiazol-5-yl)-methanol

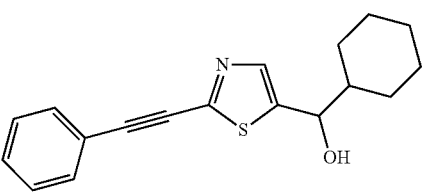 [SMILES: OC(c1cnc(C#Cc2ccccc2)s1)C1CCCCC1]

From 2-phenylethynyl-thiazole-5-carbaldehyde (Example 205, 190 mg, 0.891 mmol), following a similar procedure used for Example 234, but with a 2.0 M solution of cyclohexyl magnesium chloride in ether (490 µL, 0.98 mmol), the titled compound, cyclohexyl-(2-phenylethynyl-thiazol-5-yl)-methanol (135 mg, 51%) as brown oil was afforded.

Example 236

1-(2-Phenylethynyl-thiazol-5-yl)-ethanol

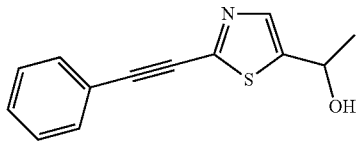 [SMILES: CC(O)c1cnc(C#Cc2ccccc2)s1]

From 2-phenylethynyl-thiazole-5-carbaldehyde (Example 205, 733 mg, 3.44 mmol), following a similar procedure used for Example 234, but with a 3.0 M solution of methyl magnesium bromide in ether (1.72 mL, 5.16 mmol), the titled compound, 1-(2-phenylethynyl-thiazol-5-yl)-ethanol (435 mg, 55%) as a pale brown solid was afforded.

Example 237

Phenyl-(2-phenylethynyl-thiazol-5-yl)-methanone

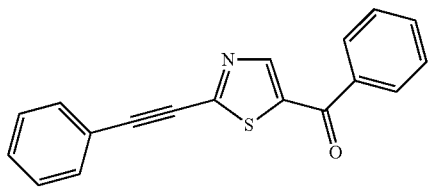 [SMILES: O=C(c1ccccc1)c1cnc(C#Cc2ccccc2)s1]

To a solution of phenyl-(2-phenylethynyl-thiazol-5-yl)-methanol (Example 234, 157 mg, 0.539 mmol) in dichloromethane (5.0 mL) was added pyridinium dichromate (243 mg, 0.647 mmol) and the reaction was stirred at room temperature for about 18 hours. The mixture was then diluted with EtOAc (15 mL), filtered over Celite® and washed with EtOAc. The solution was concentrated under reduced pressure and purified by preparative TLC, eluting with 20% EtOAc in hexanes, to afford the titled compound, phenyl-(2-phenylethynyl-thiazol-5-yl)-methanone (135 mg, 87%) as pale yellow oil.

Example 238

Cyclohexyl-(2-phenylethynyl-thiazol-5-yl)-methanone

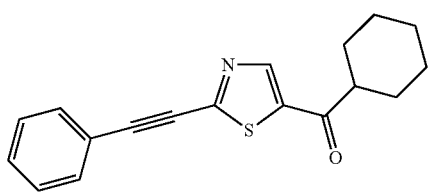 [SMILES: O=C(c1cnc(C#Cc2ccccc2)s1)C1CCCCC1]

From cyclohexyl-(2-phenylethynyl-thiazol-5-yl)-methanol (Example 235, 137 mg, 0.461 mmol), following a similar procedure used for Example 237, the titled compound, cyclohexyl-(2-phenylethynyl-thiazol-5-yl)-methanone, (91 mg, 67%) as a pale yellow solid was afforded.

Example 239

1-(2-Phenylethynyl-thiazol-5-yl)-ethanone

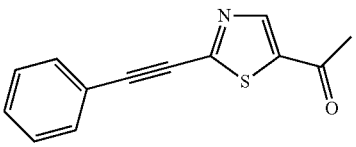 [SMILES: CC(=O)c1cnc(C#Cc2ccccc2)s1]

From 1-(2-phenylethynyl-thiazol-5-yl)-ethanol (Example 236, 428 mg, 1.87 mmol), following a similar procedure used for Example 237, the titled compound, 1-(2-phenylethynyl-thiazol-5-yl)-ethanone, (412 mg, 97%) as a brown solid was afforded.

Example 240

1-Phenyl-1-(2-phenylethynyl-thiazol-5-yl)-ethanol

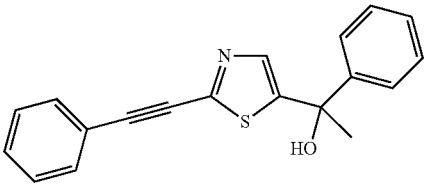 [SMILES: CC(O)(c1ccccc1)c1cnc(C#Cc2ccccc2)s1]

From phenyl-(2-phenylethynyl-thiazol-5-yl)-methanone (Example 237, 40 mg, 0.14 mmol), following a similar procedure used for Example 234, but with a 3.0 M solution of methyl magnesium bromide in ether (60 µL, 0.18 mmol), the titled compound, 1-phenyl-142-phenylethynyl-thiazol-5-yl)-ethanol, (38 mg, 90%) as a pale yellow oil was afforded.

Example 241

1-Cyclohexyl-1-(2-phenylethynyl-thiazol-5-yl)-ethanol

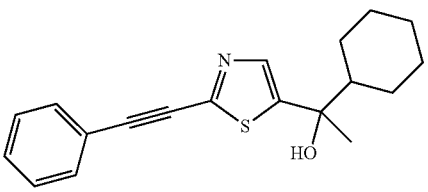 [SMILES: CC(O)(c1cnc(C#Cc2ccccc2)s1)C1CCCCC1]

From cyclohexyl-(2-phenylethynyl-thiazol-5-yl)-methanone (Example 238, 41 mg, 0.14 mmol), following a similar procedure used for Example 234, but with a 3.0 M solution of methyl magnesium bromide in ether (60 µL, 0.18 mmol), the titled compound, 1-Cyclohexyl-1-(2-phenylethynyl-thiazol-5-yl)-ethanol, (36 mg, 84%) as a pale yellow oil was afforded.

TABLE 3

| Example | Compound Name | Characterization |
|---|---|---|
| 234 | Phenyl-(2-phenylethynyl-thiazol-5-yl)-methanol | $^1$H NMR (400 MHz, CDCl$_3$) δ 7.58-7.52 (m, 2H), 7.51-7.46 (m, 1H), 7.46-7.29 (m, 8H), 6.07 (s, 1H), 4.22-3.12 (br s, 1H). (Method 3); RT = 1.55 min; Calculated [M + H]$^+$ = 292; Observed [M + H]$^+$ = 292. Yield 71% |
| 235 | Cyclohexyl-(2-phenylethynyl-thiazol-5-yl)-methanol | $^1$H NMR (400 MHz, CDCl$_3$) δ 7.65-7.51 (m, 3H), 7.46-7.31 (m, 3H), 4.72 (d, J = 6.9 Hz, 1H), 2.88 (br s, 1H), 1.94-1.58 (m, 5H), 1.38-0.92 (m, 6H). (Method 3); RT = 1.71 min; Calculated [M + H]$^+$ = 298; Observed [M + H]$^+$ = 298. Yield 51% |
| 236 | 1-(2-Phenylethynyl-thiazol-5-yl)-ethanol | $^1$H NMR (300 MHz, CDCl$_3$) δ 7.67 (s, 1H), 7.64-7.55 (m, 2H), 7.46-7.32 (m, 3H), 5.21 (q, J = 6.4 Hz, 1H), 2.54-2.12 (br s, 1H), 1.65 (d, J = 6.4 Hz, 3H). (Method 3); RT = 1.30 min; Calculated [M + H]$^+$ = 230; Observed [M + H]$^+$ = 230. Yield 55% |
| 237 | Phenyl-(2-phenylethynyl-thiazol-5-yl)-methanone | $^1$H NMR (300 MHz, CDCl$_3$) δ 8.29 (s, 1H), 7.94-7.87 (m, 2H), 7.71-7.61 (m, 3H), 7.61-7.52 (m, 2H), 7.51-7.38 (m, 3H). (Method 3); RT = 1.75 min; Calculated [M + H]$^+$ = 290; Observed [M + H]$^+$ = 290. Yield 87% |
| 238 | Cyclohexyl-(2-phenylethynyl-thiazol-5-yl)-methanone | $^1$H NMR (300 MHz, CDCl$_3$) δ 8.35 (s, 1H), 7.66-7.58 (m, 2H), 7.50-7.34 (m, 3H), 3.14-2.96 (m, 1H), 2.11-1.10 (m, 10H). (Method 3); RT = 1.89 min; Calculated [M + H]$^+$ = 296; Observed [M + H]$^+$ = 296. Yield 67% |
| 239 | 1-(2-Phenylethynyl-thiazol-5-yl)-ethanone | $^1$H NMR (300 MHz, CDCl$_3$) δ 8.34 (s, 1H), 7.67-7.60 (m, 2H), 7.51-7.36 (m, 3H), 2.63 (s, 3H), (Method 3); RT = 1.46 min; Calculated [M + H]$^+$ = 228; Observed [M + H]$^+$ = 228. Yield 97% |
| 240 | 1-Phenyl-1-(2-phenylethynyl-thiazol-5-yl)-ethanol | $^1$H NMR (400 MHz, CDCl$_3$) δ 7.63-7.54 (m, 3H), 7.54-7.48 (m, 2H), 7.47-7.28 (m, 6H), 3.30-2.59 (br s, 1H), 2.06 (s, 3H). (Method 3); RT = 1.62 min; Calculated [M + H]$^+$ = 306; Observed [M + H]$^+$ = 306. Yield 90% |
| 241 | 1-Cyclohexyl-1-(2-phenylethynyl-thiazol-5-yl)-ethanol | $^1$H NMR (400 MHz, CDCl$_3$) δ 7.65-7.51 (m, 3H), 7.46-7.31 (m, 3H), 2.45-2.12 (br s, 1H), 1.90-1.72 (m, 4H), 1.72-1.55 (m, 1H), 1.62 (s, 3H), 1.38-0.80 (m, 6H). (Method 3); RT = 1.78 min; Calculated [M + H]$^+$ = 312; Observed [M + H]$^+$ = 312. Yield 84% |

4) Hypothetical Compounds of the Invention

Examples 242-246 (below) can be made via Scheme 3 or those similarly known in the art from commercially available starting materials known to one skilled in the art.

Compounds of Formula Id

Example 242

(4-Methyl-cyclohexyl)-(2-phenylethynyl-thiazol-5-yl)-methanone

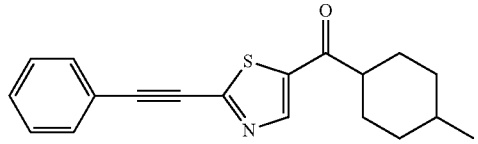 [SMILES: CC1CCC(C(=O)c2cnc(C#Cc3ccccc3)s2)CC1]

Example 243

(4-Fluoro-cyclohexyl)-(2-phenylethynyl-thiazol-5-yl)-methanone

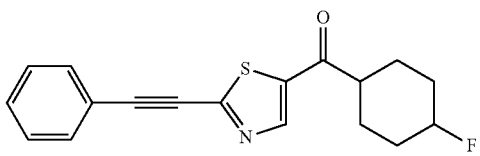 [SMILES: O=C(c1cnc(C#Cc2ccccc2)s1)C1CCC(F)CC1]

Example 244

(4-Hydroxy-cyclohexyl)-(2-phenylethynyl-thiazol-5-yl)-methanone

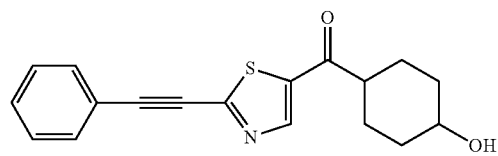

Example 245

[2-(3-Chloro-phenylethynyl)-thiazol-5-yl]-(4-hydroxy-cyclohexyl)-methanone

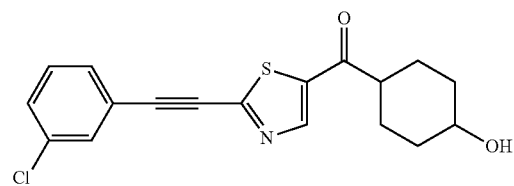 [SMILES: O=C(c1cnc(C#Cc2cccc(Cl)c2)s1)C1CCC(O)CC1]

Example 246

Cyclohexyl-[2-(6-methyl-pyridin-2-ylethynyl)-thiazol-5-yl]-methanone

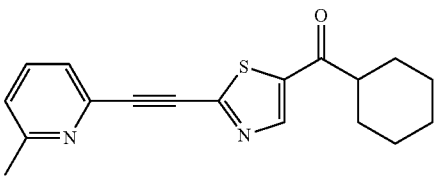 [SMILES: Cc1cccc(C#Cc2ncc(C(=O)C3CCCCC3)s2)n1]

5) Pharmacological Evaluation of Compounds of the Invention

Compounds of the present invention have been tested in vitro and in vivo, and can be tested in vitro and in vivo, in the assays as described below.

a) In vitro Assays i) Radioligand Binding Assays

Binding assays were performed as described in [J. A. O'Brien et al. *Mol. Pharmacol.*, 2003, 64, 731-740] with slight modifications. Briefly, after thawing, the membrane homogenates were resuspended in 50 mM Tris-HCl, 0.9% NaCl binding buffer at pH 7.4 to a final assay concentration of 20 μg protein/well for [$^3$H] methoxy-5-(2-pyridinylethynyl)pyridine ([$^3$H] MPEP) (American Radiolabeled Chemicals, Inc., St. Louis, Mo.) filtration binding. Incubations included 5 nM [$^3$H] MPEP, membranes and either buffer or varying concentrations of compound. Samples were incubated for 60 min at room temperature with shaking. Non-specific binding was defined with 10 μM MPEP. After incubation, samples were filtered over a GF/C filter (presoaked in 0.25% polyethyleneimine (PEI)) and then washed 4 times using a Tomtec® Harvester 96® Mach III cell harvester (Tomtec, Hamden, Conn.) with 0.5 mL ice-cold 50 mM Tris-HCl (pH 7.4).

$IC_{50}$ values were derived from the inhibition curve and $K_i$ values were calculated according to the Cheng and Prusoff equation of $Ki=IC_{50}/(1+[L]/K_d)$ described in [Y. Cheng and W. H. Prusoff *Biochem. Pharmacol.* 1973, 22, 3099-3108] where [L] is the concentration of radioligand and $K_d$ is its dissociation constant at the receptor, derived from the saturation isotherm. The $K_i$ value for representative Examples 1, 2, 7, 11, 12 and 22 were 139, 192, 860, 135, 7175, and 300 nM, respectively.

ii) Calcium Mobilization Assay to Test for Negative or Positive Allosteric Activity The cDNA for human metabotropic glutamate receptor 5 (hmGluR5) was a generous gift from S. Nakanishi (Kyoto University, Kyoto, Japan). The rmGluR5 was stably expressed in a HEK 293 cell line and grown in Dulbecco's Modified Eagle Medium (DMEM) (Invitrogen, Carlsbad, Calif.) with supplements (10% bovine calf serum, 4 mM glutamine, 100 units/mL penicillin, 100 μg/mL streptomycin and 0.75 mM G1418) at 37° C., 5% $CO_2$. Twenty-four hours prior to assay, cells were seeded into 384-well black wall microtiter plates coated with poly-D-lysine. Just prior to assay, media was aspirated and cells dye-loaded (25 μL/well) with 3 μM Fluo-4/0.01% pluronic acid in assay buffer (Hank's Balanced Saline Solution (HBSS)): 150 mM NaCl, 5 mM KCl, 1 mM $CaCl_2$, 1 mM $MgCl_2$, plus 20 mM N-2-Hydroxyethylpiperazine-N'-2-ethanesulfonic acid (HEPES), pH 7.4, 0.1% bovine serum albumin (BSA) and 2.5 mM probenicid) for 1 hour in 5% $CO_2$ at 37° C. After excess dye was discarded, cells were washed in assay buffer and layered with a final volume equal to 30 μL/well. Basal fluorescence is monitored in a fluorometric imaging plate reader (FLIPR) (Molecular Devices, Sunnyvale, Calif.) with an excitation wavelength of 488 nm and an emission range of 500 to 560 nm. Laser excitation energy was adjusted so that basal fluorescence readings were approximately 10,000 relative fluorescent units. Cells were stimulated with an $EC_{20}$ or an $EC_{80}$ concentration of glutamate in the presence of a compound to be tested, both diluted in assay buffer, and relative fluorescent units were measured at defined intervals (exposure=0.6 sec) over a 3 min period at room temperature. Basal readings derived from negative controls were subtracted from all samples. Maximum change in fluorescence was calculated for each well. Concentration-response curves derived from the maximum change in fluorescence were analyzed by non-linear regression (Hill equation).

A negative allosteric modulator (NAM) can be identified from these concentration-response curves if a compound produces a concentration dependent inhibition of the $EC_{80}$ glutamate response. Exemplified compounds of Examples 4-6, 13, 16, 21, 24, 114, 115, 123, 145, 168, 171, 173, 191, 193, 198, 231, 237 and 240 were tested in the above assay for negative allosteric modulation and their FLIPR $IC_{50}$ values were 3.2 nM, 3.2 nM, 37 nM, 53 nM, 36 nM, 7.1 nM, 0.7 nM, 54 nM, 31 nM, 33 nM, 5.0 nM, 27 nM, 25 nM, 440 nM, 29 nM, 29 nM, 20 nM, 700 nM, 360 nM and 140 nM, respectively.

A positive allosteric modulator (PAM) can be identified from these concentration-response curves if a compound produces a concentration dependent increase in the $EC_{20}$ glutamate response. The following exemplified compounds of formula (I) were tested and their exhibited positive modulation in FLIPR $EC_{50}$ ($E_{max}$) and maximum modulation (in parentheses) were: Example 1=3.6 nM (210%); Example 2=7.9 nM (130%); Example 11=3.5 nM (150%); Example 12=280 nM (170%); Example 14=23 nM (91%); Example 20=0.71 nM (110%); Example 25=55 nM (50%); Example 29=2400 nM (100%); Example 30=29 nM (110%); Example 38=12 nM; (42%); Example 41=360 nM (52%); Example 42=530 nM (160%); Example 58=5.2 nM (79%); Example 63=20 nM (140%); Example 68=440 nM (100%); Example 77=100 nM (120%); Example 78=200 nM (120%); Example 80=290 nM (120%); Example 82=4.3 nM (150%); Example 111=64 nM (130%); Example 119=140 nM (46%); Example 121=58 nM (140%); Example 122=220 nM (130%); Example 132=230 nM (40%); Example 135=20 nM (180%); Example 137=110 nM (38%); Example 140=110 nM (110%); Example 140=110 nM (110%); Example 141=4000 nM; Example 144=1.8 nM (110%); Example 146=8.2 nM (69%); Example 148=3400 nM (100%); Example 151=73 nM (61%); Example 140=110 nM (110%); Example 158=140 nM (94%); Example 159=510 nM (74%); Example 167=1900 nM (150%); Example 188=6200 nM (95%); Example 190=5.2 nM (78%); Example 192=2200 nM (64%); Example 196=12 nM (45%); Example 200=510 nM (160%); Example 206=97 nM (130%); Example 207=220 nM (110%); Example 212=37 nM (71%); Example 214=760 nM (120%); Example 218=380 nM (79%); Example 223=36 nM (110%); Example 230=33 nM (110%); Example 232=220 nM (62%); Example 235=53 nM (50%); Example 238=110 nM (130%); and Example 239=190 nM (170%).

A silent allosteric modulator (SAM) can be identified by using a combination of both the calcium mobilization assay data and the radioligand binding data. As used herein, the term "silent allosteric modulator" refers to a ligand that binds to an allosteric site of the receptor but has no measurable intrinsic efficacy. A SAM may indirectly demonstrate efficacy by preventing an allosteric binding compound from displaying its own positive (PAM) or negative (NAM) efficacy. From the above definition, if a test compound demonstrates no measurable efficacy in either the NAM-mode or the PAM-mode calcium mobilization assays, and it demonstrates measurable potency in the radioligand assay, it is a silent allosteric modulator (SAM). Representative examples of SAMs are Examples 7 and 22, for which each had FLIPR $EC_{50}$ values of >10,000 nM.

b) In Vivo Assays

An in vivo effect of a compound of the present invention may also be evaluated by using the following, non-limiting, examples of in vivo behavioral animal models. The following behavioral models are not intended as the only models useful for determining the efficacy of a compound of formula (I) to treat the corresponding disorder or disease.

Preclinically, animals also can be evaluated for blockade/attenuation of symptoms associated with schizophrenia. Positive symptoms in animal models of schizophrenia can be evaluated by measuring changes in the overall level of activity of dopamine (DA) activity with concomitant parallel changes in locomotor activity as described in [R. Depoortere et al. *Neuropsychopharmacology*, 2003, 28, 11: 1889-902], D-amphetamine (AMPH) and phencyclidine (PCP) via induction of model psychosis or locomotor hyperactivity as described in [W. J. Freed et al. *Neuropharmacology*, 1984, 23, 2A: 175-81; F. Sams-Dodd *Neuropsychopharmacology*, 1998 19, 1: 18-25]. For example, Depoortere et al., 2003, have described tests for evaluating locomotor activity, catalepsy, climbing and stereotypy, which relate to positive symptomology and side effect profile, by characterizing compounds with typical and atypical antipsychotic efficacy. Attenuation in apomorphine-induced climbing, stereotypy and catalepsy (AIC) can be evaluated as described in [Y. K. Fung et al. *Pharmacol. Biochem. Behav.*, 1986, 24, 1: 139-41 and Y. K. Fung et al. *Steroids*, 1987, 49, 4-5: 287-94]. Additionally, negative symptoms of schizophrenia can be evaluated by measuring social interaction under the influence of NMDA antagonists such as PCP, as described in F. Sams-Dodd, 1998, supra.

Cognitive symptoms of memory can be evaluated by such models as the Fear Conditioning Paradigm described in [T. J. Gould et al. *Behav. Pharmacol.*, 2002, 13, 4: 287-94, and A. O. Hamm et al. *Brain*, 2003, 126, Pt 2: 267-75] and the Radial Arm Test described in [J. P. Aggleton et al. *Behav. Brain Res.*, 1996, 19, 2: 133-46], while spatial reference memory and learning can be evaluated in the Morris water maze test as described in [Morris. *Learn. Motiv.*, 1981, 12, 239-260; B. Bontempi et al. *Eur. J. Neurosci.* 1996, 8, 11: 2348-60]. More specifically, in the Morris water maze test, a circular water tank (150 cm diameter and 45 cm height) is filled with about 30 cm water and maintained at 26-28° C. with an escape platform (15 cm diameter) 18 cm from the perimeter and always in the same position 1.5 cm beneath the surface of the water. The water is made opaque by addition of a non-toxic coloring agent (e.g., milk powder) rendering the platform invisible. Animals are given a single training session over a single day. The training session consists of 4 consecutive trials in the water maze, each separated by 60 seconds. For each trial, the animal is placed in the water maze at one of two starting points equidistant from the escape platform and allowed to find the escape platform. The animal is left on the escape platform for 60 seconds before starting a new trial. If the animal does not find the platform within 120 seconds, the animal is removed from the water and placed on the platform for 60 seconds. During the 4 trials, the animals start the water maze twice from each starting point in a randomly determined order per animal. Appropriate animals for testing with acclimatization conditions are, for example, the male Rj: Wistar (Hans) rats. The principal measure taken in each trial is the distance traveled to find the platform. Secondary measures taken are the swim speed and escape latency.

The cognitive domain of executive functioning includes processes such as planning, organization, mental flexibility and task coordination and is considered to be the domain in which schizophrenia patients have the most difficulties. The attentional set-shifting paradigm is an animal model which allows assessment of executive functioning via intra-dimensional (ID) versus extra-dimensional (ED) shift discrimination learning. A schizophrenia-disease-like animal model with subchronic phencyclidine (PCP) administration plus washout period is applied. The subchronic PCP with washout treatment regime appears to induce the most selective impairment, with a performance deficit confined to ED shift performance only, indicating that this specific pharmacological manipulation may model more effectively the executive functioning deficits observed in first-episode schizophrenia patients. Executive functioning, therefore, can be evaluated via an in vivo assessment of "attentional set-shifting performance" as described by Rodefer et al. (*Eur. J. Neurosci.* 21:1070-1076 (2005)), and was based on a modified version of the task designed by Birrell & Brown (*J. Neurosci.* 20:4320-4324 (2000)).

Cognition can be assessed by the novel object recognition (NOR). NOR can be used to access cognitive performance with respect to processes of working memory, such as recognition, interpretation and appropriate response. The NOR test was performed using the compound of Example 1 and reference compound in vehicle of 20% β-cyclodextrin (βCD) in dH$_2$O. Example 1 (at 3.0 mg/kg, ip in rats) has activity as measured in the NOR test. See FIG. 1. Along with Example 1, Examples 2, 12 and 35 (at 1.0 mg/kg, po in rats) have activity as measured in the NOR test. See FIG. 2.

Also, it has been demonstrated by [Grayson B. et al. *Behavioural Brain Research* 184 (2007) 31-38] that sub-chronic PCP (phencyclidine) treatment in combination with the NOR test is a useful model for detecting compounds with therapeutic potential in treating the symptomology of cognitive dysfunction associated with schizophrenia.

Additionally, with respect to cognition, memory and hippocampal hypo-functioning can be assessed by measuring the restoration of synaptic plasticity in ovariectomized (OVX) female rats as described in [M. Day and M. Good *Neurobiol. Learn. Mem.*, 2005, 83, 1: 13-21]. Further, changes in attention function because of schizophrenia can be examined by the Five (5) Choice Serial Reaction Time Test (5CSRT) described in [J. L. Muir et al. *Psychopharmacology (Berl)*, 1995, 118, 1: 82-92 and Robbins et al. *Ann. N.Y. Acad. Sci.*, 1998, 846, 222-37].

Human patients can be evaluated for cognitive diseases or disorders by any of the tests within the skill of those in the art, including The MATRICS Consensus Cognitive Battery (MCCB) (2009) (Matrics Assessment Inc., Los Angeles, Calif., USA).

Each reference cited in the present application, including literature references, books, patents and patent applications, is incorporated herein by reference in its entirety.

What is claimed is:
1. A compound of formula (I):

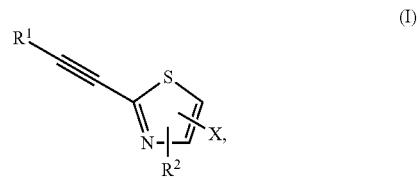

wherein:
X is —CONR$^3$R$^4$, wherein:
R$^3$ is hydrogen or C$_1$-C$_6$alkyl;
R$^4$ is unsubstituted C$_1$-C$_6$alkyl, or R$^4$ may be cycloalkyl, or heterocyclyl, each of which is optionally mono-, di-, or tri-substituted independently with C$_1$-C$_6$alkyl, halogen, cycloalkyl, and aryl; or
R$^3$ and R$^4$ taken together with the N to which they are attached to form a 4 to 10 membered heterocyclyl, which optionally contains at least one additional heteroatom and optionally is mono-, di-, or tri-substituted independently with C$_1$-C$_6$alkyl, hydroxy, C$_1$-C$_6$ alkoxy, C$_1$-C$_6$alkoxyalkyl, C$_1$-C$_6$cycloalkyl, CO$_2$C$_1$-C$_6$alkyl, hydroxyalkyl, —CN, —NH$_2$, —NH(C$_1$-C$_3$alkyl), —N(C$_1$-C$_3$alkyl)$_2$, —NHCOC$_1$-C$_6$alkyl, acyl, aryl, heteroaryl, heterocyclyl, heterocyclyl-C$_1$-C$_6$alkyl, =O, and halogen;
R$^1$ is hydrogen, C$_1$-C$_6$alkyl, C$_3$-C$_6$cycloalkyl, aryl or heteroaryl, which is optionally mono-, or di-substituted independently with C$_1$-C$_3$alkyl, C$_1$-C$_3$alkoxy, hydroxyl, CF$_3$, CHF$_2$, CN and halogen;
R$^2$ is hydrogen, C$_1$-C$_3$alkyl, CF$_3$, CHF$_2$, or halogen;
with the proviso that X and R$^2$ are attached either to the fourth or fifth carbon of the thiazole ring and when X is attached to the fourth carbon, R$^2$ is attached to the fifth carbon and vice versa; or
a pharmaceutically-acceptable salt thereof.
2. The compound of claim 1, wherein the compound is of formula (Ia-i):

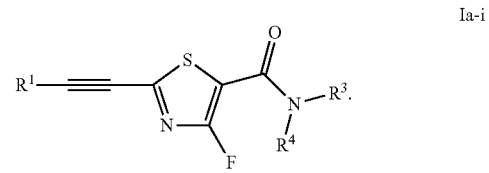

3. The compound of claim 1, wherein R$^1$ is an alkyl, cycloalkyl, aryl or heteroaryl.
4. The compound of claim 1, wherein R$^1$ is a cyclohexyl, phenyl, thienyl, furyl, pyrazinyl, pyrimidyl, pyridyl, thiazolyl, or a moiety as shown below:

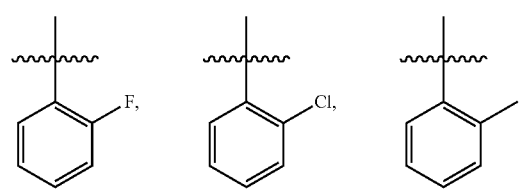

-continued
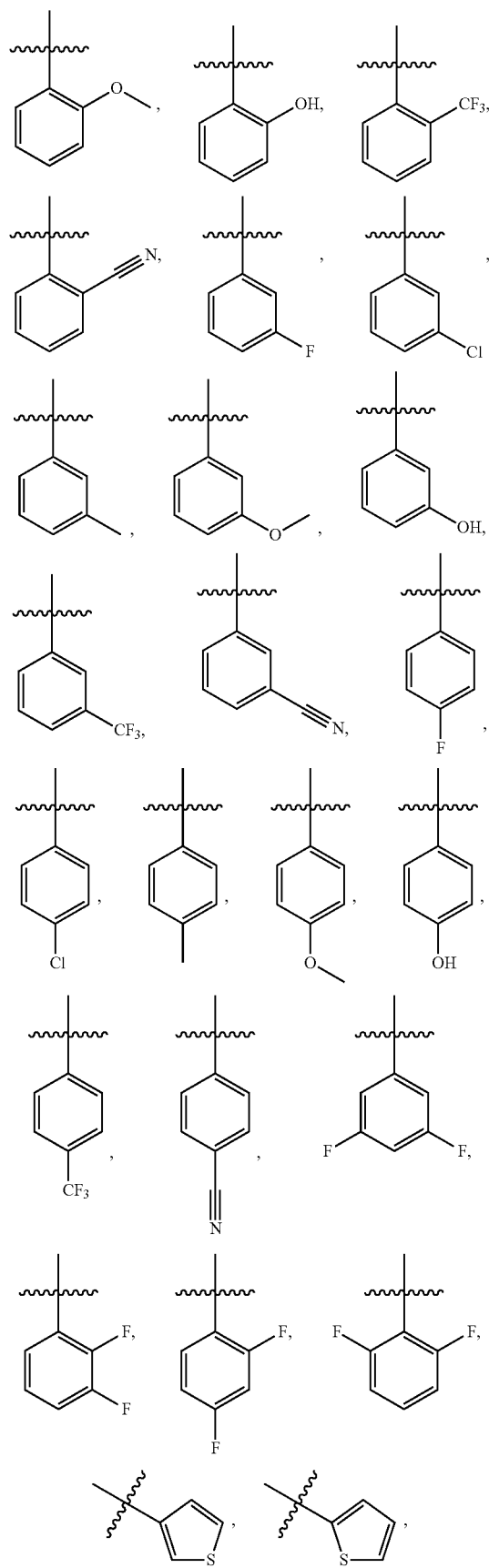
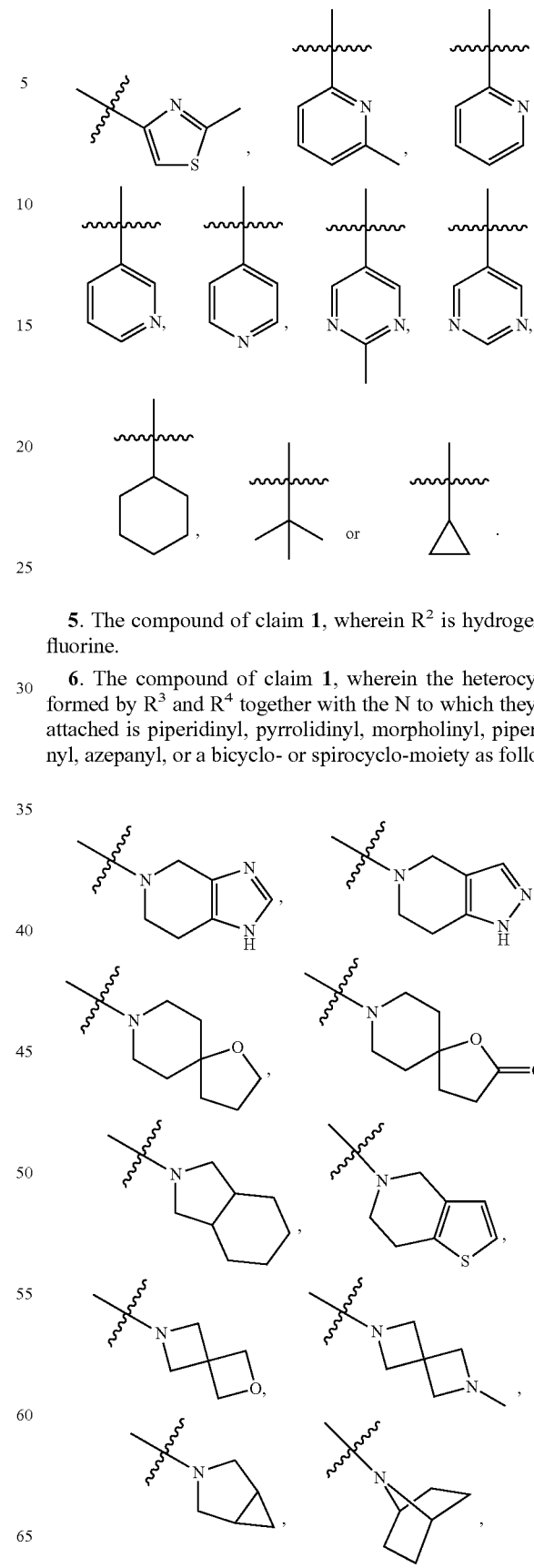
5. The compound of claim 1, wherein $R^2$ is hydrogen or fluorine.
6. The compound of claim 1, wherein the heterocyclyl formed by $R^3$ and $R^4$ together with the N to which they are attached is piperidinyl, pyrrolidinyl, morpholinyl, piperazinyl, azepanyl, or a bicyclo- or spirocyclo-moiety as follows:
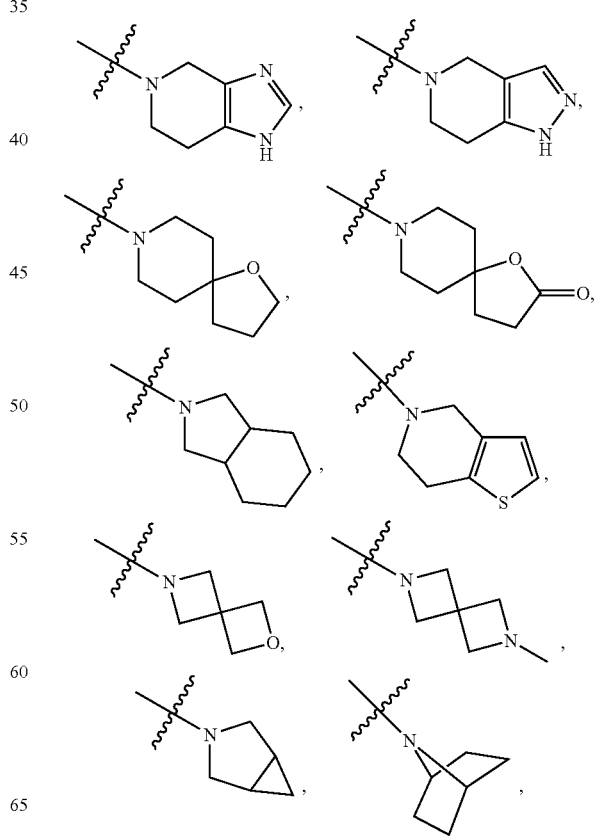

-continued

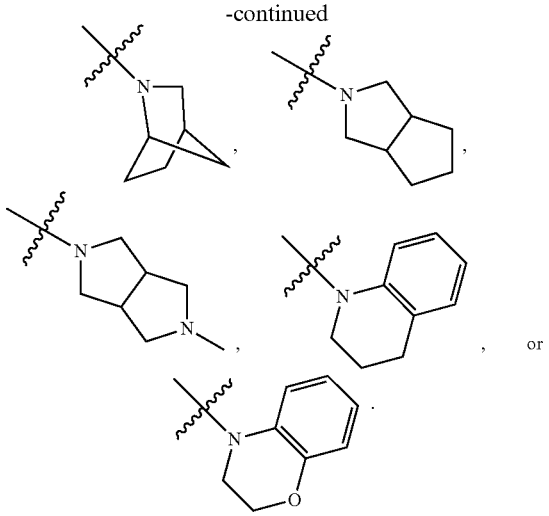

7. The compound of claim 1, wherein the compound is:
(2-Phenylethynyl-thiazol-5-yl)-piperidin-1-yl-methanone;
(4-Fluoro-piperidin-1-yl)-(2-phenylethynyl-thiazol-5-yl)-methanone;
(3-Fluoro-piperidin-1-yl)-(2-phenylethynyl-thiazol-5-yl)-methanone;
(2-Phenylethynyl-thiazol-5-yl)-pyrrolidin-1-yl-methanone;
((S)-3-Fluoro-pyrrolidin-1-yl)-(2-phenylethynyl-thiazol-5-yl)-methanone;
((R)-3-Fluoro-pyrrolidin-1-yl)-(2-phenylethynyl-thiazol-5-yl)-methanone;
Morpholin-4-yl-(2-phenylethynyl-thiazol-5-yl)-methanone;
(3-Hydroxy-piperidin-1-yl)-(2-phenylethynyl-thiazol-5-yl)-methanone;
(4-Hydroxymethyl-piperidin-1-yl)-(2-phenylethynyl-thiazol-5-yl)-methanone;
(2,6-Dimethyl-morpholin-4-yl)-(2-phenylethynyl-thiazol-5-yl)-methanone;
(4-Methyl-piperidin-1-yl)-(2-phenylethynyl-thiazol-5-yl)-methanone;
(4-Hydroxy-piperidin-1-yl)-(2-phenylethynyl-thiazol-5-yl)-methanone;
(4-Methyl-2-phenylethynyl-thiazol-5-yl)-piperidin-1-yl-methanone;
(4-Methyl-2-phenylethynyl-thiazol-5-yl)-(4-methyl-piperidin-1-yl)-methanone;
(4-Hydroxy-piperidin-1-yl)-(4-methyl-2-phenylethynyl-thiazol-5-yl)-methanone;
4-Methyl-2-phenylethynyl-thiazole-5-carboxylic acid cyclopentylamide;
[2-(3-Fluoro-phenylethynyl)-thiazol-5-yl]-piperidin-1-yl-methanone;
2-(3-Fluoro-phenylethynyl)-thiazole-5-carboxylic acid cyclopentylamide;
[2-(3-Fluoro-phenylethynyl)-thiazol-5-yl]-(4-hydroxy-piperidin-1-yl)-methanone;
2-(3-Fluoro-phenylethynyl)-thiazol-5-yl]-(4-methyl-piperidin-1-yl)-methanone;
[2-(3-Fluoro-phenylethynyl)-thiazol-5-yl]-pyrrolidin-1-yl-methanone;
[2-(3-Fluoro-phenylethynyl)-thiazol-5-yl]-morpholin-4-yl-methanone;
Piperidin-1-yl-(2-m-tolylethynyl-thiazol-5-yl)-methanone;
2-m-Tolylethynyl-thiazole-5-carboxylic acid cyclopentylamide;
(4-Hydroxy-piperidin-1-yl)-(2-m-tolylethynyl-thiazol-5-yl)-methanone;
Morpholin-4-yl-(2-m-tolylethynyl-thiazol-5-yl)-methanone;
Pyrrolidin-1-yl-(2-m-tolylethynyl-thiazol-5-yl)-methanone;
(4-Methyl-piperidin-1-yl)-(2-m-tolylethynyl-thiazol-5-yl)-methanone;
[2-(4-Fluoro-phenylethynyl)-thiazol-5-yl]-(4-hydroxy-piperidin-1-yl)-methanone;
[2-(4-Fluoro-phenylethynyl)-thiazol-5-yl]-piperidin-1-yl-methanone;
2-(4-Fluoro-phenylethynyl)-thiazole-5-carboxylic acid cyclopentylamide;
[2-(4-Fluoro-phenylethynyl)-thiazol-5-yl]-morpholin-4-yl-methanone;
[2-(3-Fluoro-phenylethynyl)-thiazol-5-yl]-pyrrolidin-1-yl-methanone;
[2-(4-Fluoro-phenylethynyl)-thiazol-5-yl]-(4-methyl-piperidin-1-yl)-methanone;
[2-(3-Chloro-phenylethynyl)-thiazol-5-yl]-piperidin-1-yl-methanone;
[2-(3-Chloro-phenylethynyl)-thiazol-5-yl]-morpholin-4-yl-methanone;
2-(3-Chloro-phenylethynyl)-thiazole-5-carboxylic acid cyclopentylamide;
[2-(3-Chloro-phenylethynyl)-thiazol-5-yl]-(4-hydroxy-piperidin-1-yl)-methanone;
[2-(3-Chloro-phenylethynyl)-thiazol-5-yl]-pyrrolidin-1-yl-methanone;
[2-(4-Fluoro-phenylethynyl)-thiazol-5-yl]-(4-methyl-piperidin-1-yl)-methanone;
(2-Phenylethynyl-thiazol-5-yl)-(4-phenyl-piperazin-1-yl)-methanone;
(4-Methyl-piperazin-1-yl)-(2-phenylethynyl-thiazol-5-yl)-methanone;
(4-Ethyl-piperazin-1-yl)-(2-phenylethynyl-thiazol-5-yl)-methanone;
(4-Cyclohexyl-piperazin-1-yl)-(2-phenylethynyl-thiazol-5-yl)-methanone;
[4-(2-Hydroxy-ethyl)-piperazin-1-yl]-(2-phenylethynyl-thiazol-5-yl)-methanone;
(4-Isopropyl-piperazin-1-yl)-(2-phenylethynyl-thiazol-5-yl)-methanone;
4-(2-Phenylethynyl-thiazole-5-carbonyl)-piperazin-2-one;
Piperidin-1-yl-(2-p-tolylethynyl-thiazol-5-yl)-methanone;
[2-p-Tolylethynyl-thiazole-5-carboxylic acid cyclopentylamide;
(4-Hydroxy-piperidin-1-yl)-(2-p-tolylethynyl-thiazol-5-yl)-methanone;
Pyrrolidin-1-yl-(2-p-tolylethynyl-thiazol-5-yl)-methanone;
(4-Methyl-piperidin-1-yl)-(2-p-tolylethynyl-thiazol-5-yl)-methanone;
Morpholin-4-yl-(2-p-tolylethynyl-thiazol-5-yl)-methanone;
[2-(4-Chloro-phenylethynyl)-thiazol-5-yl]-piperidin-1-yl-methanone;
[2-(4-Chloro-phenylethynyl)-thiazol-5-yl]-(4-hydroxy-piperidin-1-yl)-methanone;

[2-(4-Chloro-phenylethynyl)-thiazol-5-yl]-morpholin-4-yl-methanone;
[2-(4-Chloro-phenylethynyl)-thiazol-5-yl]-(4-methyl-piperidin-1-yl)-methanone;
Azepan-1-yl-(2-phenylethynyl-thiazol-5-yl)-methanone;
2-(2-Fluoro-phenylethynyl)-thiazole-5-carboxylic acid cyclopentylamide;
[2-(2-Fluoro-phenylethynyl)-thiazol-5-yl]-(4-hydroxy-piperidin-1-yl)-methanone;
[2-(2-Fluoro-phenylethynyl)-thiazol-5-yl]-morpholin-4-yl-methanone;
[2-(2-Fluoro-phenylethynyl)-thiazol-5-yl]-piperidin-1-yl-methanone;
[2-(2-Fluoro-phenylethynyl)-thiazol-5-yl]-(4-methyl-piperidin-1-yl)-methanone;
2-(2-Chloro-phenylethynyl)-thiazole-5-carboxylic acid cyclopentylamide;
[2-(2-Chloro-phenylethynyl)-thiazol-5-yl]-(4-hydroxy-piperidin-1-yl)-methanone;
[2-(2-Chloro-phenylethynyl)-thiazol-5-yl]-morpholin-4-yl-methanone;
[2-(2-Chloro-phenylethynyl)-thiazol-5-yl]-(4-methyl-piperidin-1-yl)-methanone;
[2-(2-Chloro-phenylethynyl)-thiazol-5-yl]-piperidin-1-yl-methanone;
Piperidin-1-yl-(2-o-tolylethynyl-thiazol-5-yl)-methanone;
(4-Hydroxy-piperidin-1-yl)-(2-o-tolylethynyl-thiazol-5-yl)-methanone;
Morpholin-4-yl-(2-o-tolylethynyl-thiazol-5-yl)-methanone;
(4-Methyl-piperidin-1-yl)-(2-o-tolylethynyl-thiazol-5-yl)-methanone;
2-o-Tolylethynyl-thiazole-5-carboxylic acid cyclopentylamide;
Pyrrolidin-1-yl-(2-o-tolylethynyl-thiazol-5-yl)-methanone;
1-(2-Phenylethynyl-thiazole-5-carbonyl)-piperidin-4-one;
(2-Phenylethynyl-thiazol-5-yl)-(1,4,6,7-tetrahydro-imidazo[4,5-c]pyridin-5-yl)-methanone;
(2-Phenylethynyl-thiazol-5-yl)-(1,4,6,7-tetrahydro-pyrazolo[4,3-c]pyridin-5-yl)-methanone;
(1-Oxa-8-aza-spiro[4.5]dec-8-yl)-(2-phenylethynyl-thiazol-5-yl)-methanone;
8-(2-Phenylethynyl-thiazole-5-carbonyl)-1-oxa-8-aza-spiro[4.5]decan-2-one;
(4-Hydroxy-4-methyl-piperidin-1-yl)-(2-phenylethynyl-thiazol-5-yl)-methanone;
((R)-3-Hydroxy-piperidin-1-yl)-(2-phenylethynyl-thiazol-5-yl)-methanone;
(4,4-Difluoro-piperidin-1-yl)-(2-phenylethynyl-thiazol-5-yl)-methanone;
(4,4-Difluoro-piperidin-1-yl)-[2-(3-fluoro-phenylethynyl)-thiazol-5-yl]-methanone;
[2-(3-Fluoro-phenylethynyl)-thiazol-5-yl]-(4-fluoro-piperidin-1-yl)-methanone;
(3,3-Difluoro-piperidin-1-yl)-(2-phenylethynyl-thiazol-5-yl)-methanone;
2-Phenylethynyl-thiazole-4-carboxylic acid cyclopropylamide;
2-Phenylethynyl-thiazole-4-carboxylic acid ethylamide;
2-Phenylethynyl-thiazole-4-carboxylic acid isopropylamide;
2-Phenylethynyl-thiazole-4-carboxylic acid cyclohexylamide;
2-Phenylethynyl-thiazole-4-carboxylic acid cyclopentylamide;
2-Phenylethynyl-thiazole-5-carboxylic acid isopropylamide;
2-Phenylethynyl-thiazole-5-carboxylic acid cyclopentylamide;
2-Phenylethynyl-thiazole-5-carboxylic acid cyclopropylamide;
2-Phenylethynyl-thiazole-5-carboxylic acid ethylamide;
2-Phenylethynyl-thiazole-5-carboxylic acid cyclohexylamide;
(2-Phenylethynyl-thiazol-5-yl)-(4-trifluoromethyl-piperidin-1-yl)-methanone;
2-Phenylethynyl-thiazole-5-carboxylic acid diethylamide;
(3-Dimethylamino-pyrrolidin-1-yl)-(2-phenylethynyl-thiazol-5-yl)-methanone;
(3,3-Difluoro-azetidin-1-yl)-(2-phenylethynyl-thiazol-5-yl)-methanone;
(3,3-Difluoro-pyrrolidin-1-yl)-(2-phenylethynyl-thiazol-5-yl)-methanone;
2-Phenylethynyl-thiazole-5-carboxylic acid dimethylamide;
(4-Dimethylamino-piperidin-1-yl)-(2-phenylethynyl-thiazol-5-yl)-methanone;
(2-Phenylethynyl-thiazol-5-yl)-(4-pyrrolidin-1-yl-piperidin-1-yl)-methanone;
(3-Methoxy-piperidin-1-yl)-(2-phenylethynyl-thiazol-5-yl)-methanone;
(3-Ethoxy-piperidin-1-yl)-(2-phenylethynyl-thiazol-5-yl)-methanone;
(4-Methoxy-piperidin-1-yl)-(2-phenylethynyl-thiazol-5-yl)-methanone;
(4-Ethoxy-piperidin-1-yl)-(2-phenylethynyl-thiazol-5-yl)-methanone;
(3-Methoxymethyl-piperidin-1-yl)-(2-phenylethynyl-thiazol-5-yl)-methanone;
(4-Methoxymethyl-piperidin-1-yl)-(2-phenylethynyl-thiazol-5-yl)-methanone;
(2-Phenylethynyl-thiazol-5-yl)-(3-pyrrolidin-1-yl-piperidin-1-yl)-methanone;
1-(2-Phenylethynyl-thiazole-5-carbonyl)-piperidine-4-carboxylic acid methyl ester;
1-(2-Phenylethynyl-thiazole-5-carbonyl)-piperidine-3-carboxylic acid methyl ester;
Azetidin-1-yl-(2-phenylethynyl-thiazol-5-yl)-methanone;
(3-Hydroxy-azetidin-1-yl)-(2-phenylethynyl-thiazol-5-yl)-methanone;
N-[1-(2-Phenylethynyl-thiazole-5-carbonyl)-piperidin-4-yl]-acetamide;
N-[1-(2-Phenylethynyl-thiazole-5-carbonyl)-piperidin-3-yl]-acetamide;
(2-Phenylethynyl-thiazol-5-yl)-(3-piperidin-1-yl-azetidin-1-yl)-methanone;
(3-Morpholin-4-yl-azetidin-1-yl)-(2-phenylethynyl-thiazol-5-yl)-methanone;
(2-Phenylethynyl-thiazol-5-yl)-(3-pyrrolidin-1-yl-azetidin-1-yl)-methanone;
(2,3-Dihydro-benzo[1,4]oxazin-4-yl)-(2-phenylethynyl-thiazol-5-yl)-methanone;
(6,7-Dihydro-4H-thieno[3,2-c]pyridin-5-yl)-(2-phenylethynyl-thiazol-5-yl)-methanone;
(3-Methoxy-pyrrolidin-1-yl)-(2-phenylethynyl-thiazol-5-yl)-methanone;
(3-Hydroxy-3-methyl-pyrrolidin-1-yl)-(2-phenylethynyl-thiazol-5-yl)-methanone;
1-(2-Phenylethynyl-thiazole-5-carbonyl)-pyrrolidine-3-carboxylic acid methyl ester;

(Octahydro-isoindol-2-yl)-(2-phenylethynyl-thiazol-5-yl)-methanone;
1-(2-Phenylethynyl-thiazole-5-carbonyl)-pyrrolidin-3-one;
[1,3]Bipyrrolidinyl-1-yl-(2-phenylethynyl-thiazol-5-yl)-methanone;
(3-Azetidin-1-yl-pyrrolidin-1-yl)-(2-phenylethynyl-thiazol-5-yl)-methanone;
N-[1-(2-Phenylethynyl-thiazole-5-carbonyl)-pyrrolidin-3-yl]-acetamide;
(Hexahydro-cyclopenta[c]pyrrol-2-yl)-(2-phenylethynyl-thiazol-5-yl)-methanone;
(7-Aza-bicyclo[2.2.1]hept-7-yl)-(2-phenylethynyl-thiazol-5-yl)-methanone;
(2-Aza-bicyclo[2.2.1]hept-2-yl)-(2-phenylethynyl-thiazol-5-yl)-methanone;
1-(2-Phenylethynyl-thiazole-5-carbonyl)-azepan-4-one;
(4-Morpholin-4-yl-azepan-1-yl)-(2-phenylethynyl-thiazol-5-yl)-methanone;
1-(2-Phenylethynyl-thiazole-5-carbonyl)-piperidin-4-one;
(3-Dimethylamino-piperidin-1-yl)-(2-phenylethynyl-thiazol-5-yl)-methanone;
(4-Hydroxy-4-methyl-azepan-1-yl)-(2-phenylethynyl-thiazol-5-yl)-methanone;
(4-Methoxy-azepan-1-yl)-(2-phenylethynyl-thiazol-5-yl)-methanone;
(2,5-Dimethyl-pyrrolidin-1-yl)-(2-phenylethynyl-thiazol-5-yl)-methanone;
(2-Methyl-piperidin-1-yl)-(2-phenylethynyl-thiazol-5-yl)-methanone;
(2,6-Dimethyl-piperidin-1-yl)-(2-phenylethynyl-thiazol-5-yl)-methanone;
(2-Methyl-pyrrolidin-1-yl)-(2-phenylethynyl-thiazol-5-yl)-methanone;
[2-(3-Chloro-phenylethynyl)-thiazol-5-yl]-[4-(2-methoxy-ethyl)-piperazin-1-yl]-methanone;
[2-(3-Chloro-phenylethynyl)-thiazol-5-yl]-(4-methyl-piperazin-1-yl)-methanone;
[2-(3-Chloro-phenylethynyl)-thiazol-5-yl]-(4-ethyl-piperazin-1-yl)-methanone;
[2-(3-Chloro-phenylethynyl)-thiazol-5-yl]-[4-(2-hydroxy-ethyl)-piperazin-1-yl]-methanone;
[2-(3-Chloro-phenylethynyl)-thiazol-5-yl]-(4-hydroxy-4-methyl-piperidin-1-yl)-methanone;
[2-(2-Fluoro-phenylethynyl)-thiazol-5-yl]-pyrrolidin-1-yl-methanone;
[2-(2-Chloro-phenylethynyl)-thiazol-5-yl]-pyrrolidin-1-yl-methanone;
[2-(3-Chloro-phenylethynyl)-thiazol-5-yl]-(3,4,6,7-tetrahydro-imidazo[4,5-c]pyridin-5-yl)-methanone;
[2-(3-Chloro-phenylethynyl)-thiazol-5-yl]-(1,4,6,7-tetrahydro-pyrazolo[4,3-c]pyridin-5-yl)-methanone;
[2-(4-Chloro-phenylethynyl)-thiazol-5-yl]-pyrrolidin-1-yl-methanone;
(2-Oxa-6-aza-spiro[3.3]hept-6-yl)-(2-phenylethynyl-thiazol-5-yl)-methanone;
((S)-2-Methoxymethyl-pyrrolidin-1-yl)-(2-phenylethynyl-thiazol-5-yl)-methanone;
((R)-2-Methoxymethyl-pyrrolidin-1-yl)-(2-phenylethynyl-thiazol-5-yl)-methanone;
(2-Hydroxymethyl-piperidin-1-yl)-(2-phenylethynyl-thiazol-5-yl)-methanone;
5-(2-Phenylethynyl-thiazole-5-carbonyl)-hexahydro-pyrrolo[3,4-c]pyrrole-2-carboxylic acid tert-butyl ester;
(2-Phenylethynyl-thiazol-5-yl)-((S)-2-pyrrolidin-1-ylmethyl-pyrrolidin-1-yl)-methanone;
(Hexahydro-pyrrolo[3,4-c]pyrrol-2-yl)-(2-phenylethynyl-thiazol-5-yl)-methanone;
1-[5-(2-Phenylethynyl-thiazole-5-carbonyl)-hexahydro-pyrrolo[3,4-c]pyrrol-2-yl]-ethanone;
(5-Methyl-hexahydro-pyrrolo[3,4-c]pyrrol-2-yl)-(2-phenylethynyl-thiazol-5-yl)-methanone;
((S)-3-Hydroxy-pyrrolidin-1-yl)-(2-phenylethynyl-thiazol-5-yl)-methanone;
((R)-3-Hydroxy-pyrrolidin-1-yl)-(2-phenylethynyl-thiazol-5-yl)-methanone;
(4-Bromo-2-phenylethynyl-thiazol-5-yl)-piperidin-1-yl-methanone;
[2-(2,6-Difluoro-phenylethynyl)-thiazol-5-yl]-piperidin-1-yl-methanone;
[2-(3,5-Difluoro-phenylethynyl)-thiazol-5-yl]-piperidin-1-yl-methanone;
[2-(2-Hydroxy-phenylethynyl)-thiazol-5-yl]-piperidin-1-yl-methanone;
[2-(4-Hydroxy-phenylethynyl)-thiazol-5-yl]-piperidin-1-yl-methanone;
[2-(3-Hydroxy-phenylethynyl)-thiazol-5-yl]-piperidin-1-yl-methanone;
2-(2,4-Difluoro-phenylethynyl)-thiazol-5-yl]-piperidin-1-yl-methanone;
(2-Cyclohexylethynyl-thiazol-5-yl)-piperidin-1-yl-methanone;
[2-(3,3-Dimethyl-but-1-ynyl)-thiazol-5-yl]-piperidin-1-yl-methanone;
Piperidin-1-yl-[2-(3-trifluoromethyl-phenylethynyl)-thiazol-5-yl]-methanone;
Piperidin-1-yl-(2-pyridin-3-ylethynyl-thiazol-5-yl)-methanone;
[2-(3-Methoxy-phenylethynyl)-thiazol-5-yl]-piperidin-1-yl-methanone;
Piperidin-1-yl-(2-thiophen-3-ylethynyl-thiazol-5-yl)-methanone;
Piperidin-1-yl-(2-pyridin-2-ylethynyl-thiazol-5-yl)-methanone;
[2-(4-Methoxy-phenylethynyl)-thiazol-5-yl]-piperidin-1-yl-methanone;
[2-(6-Methyl-pyridin-2-ylethynyl)-thiazol-5-yl]-piperidin-1-yl-methanone;
Piperidin-1-yl-(2-pyrimidin-5-ylethynyl-thiazol-5-yl)-methanone;
(2-Ethynyl-thiazol-5-yl)-piperidin-1-yl-methanone;
3-[5-(Piperidine-1-carbonyl)-thiazol-2-ylethynyl]-benzonitrile;
4-[5-(Piperidine-1-carbonyl)-thiazol-2-ylethynyl]-benzonitrile;
(2-Pyridin-2-ylethynyl-thiazol-5-yl)-pyrrolidin-1-yl-methanone;
Morpholin-4-yl-(2-pyridin-2-ylethynyl-thiazol-5-yl)-methanone;
(2-Cyclohexylethynyl-thiazol-5-yl)-piperidin-1-yl-methanone;
[2-(3,3-Dimethyl-but-1-ynyl)-thiazol-5-yl]-piperidin-1-yl-methanone;
Piperidin-1-yl-[2-(3-trifluoromethyl-phenylethynyl)-thiazol-5-yl]-methanone;
Piperidin-1-yl-(2-pyridin-3-ylethynyl-thiazol-5-yl)-methanone;
[2-(2-Methoxy-phenylethynyl)-thiazol-5-yl]-piperidin-1-yl-methanone;
a pharmaceutically acceptable salt thereof.

8. A pharmaceutical composition comprising at least one compound of claim 1 and at least one pharmaceutically acceptable carrier or excipient.

9. A method of improving cognitive functioning, comprising administering an effective amount of a compound of claim 1 to a human in need thereof wherein the compound allosterically modulates mGlu5.

10. The method according to claim 9, wherein the human suffers from cognitive dysfunction.

11. The method of claim 10, wherein the cognitive dysfunction presents in connection with a disease or disorder selected from the group consisting of psychosis, schizophrenia, a disease involving a psychotic symptom, schizophreniform disorder, schizoaffective disorder, delusional disorder, brief psychotic disorder, shared psychotic disorder, substance-induced psychotic disorder, an affective disorder, ADHD, or a combination thereof.

12. The method according to claim 11, wherein the affective disorder is depression, mania, or bipolar disorder.

13. The method according to claim 11, wherein the disease or disorder is schizophrenia.

14. The method according to claim 11, wherein the disease or disorder is ADHD.

15. The method according to claim 11, wherein the method further comprises reducing a cognitive symptom in a schizophrenic patient or ADHD patient.

16. A method of treating a disease or disorder, comprising administering an effective amount of a compound of claim 1 to a human in need thereof, wherein the disease or disorder is schizophrenia, cognition, cognitive impairment associated with schizophrenia (CIAS), psychosis, depression, mania, bipolar disorder, ADHD, or a combination thereof wherein the compound allosterically modulates mGlu5.

* * * * *